US011147650B2

(12) United States Patent
Armour et al.

(10) Patent No.: US 11,147,650 B2
(45) Date of Patent: *Oct. 19, 2021

(54) STERILE SITE APPARATUS, SYSTEM, AND METHOD OF USING THE SAME

(71) Applicant: Armour Technologies, Inc., Swarthmore, PA (US)

(72) Inventors: Andrew W. Armour, Swarthmore, PA (US); Kevin McGough, Wallingford, PA (US); William Gallo, Newtown Square, PA (US)

(73) Assignee: Armour Technologies, Inc., Swarthmore, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/379,975

(22) Filed: Apr. 10, 2019

(65) Prior Publication Data

US 2019/0262097 A1    Aug. 29, 2019

Related U.S. Application Data

(60) Continuation of application No. 15/443,860, filed on Feb. 27, 2017, now Pat. No. 10,299,882, which is a
(Continued)

(51) Int. Cl.
*A61L 2/10* (2006.01)
*A61B 90/40* (2016.01)
(Continued)

(52) U.S. Cl.
CPC .......... *A61B 90/40* (2016.02); *A61B 17/0293* (2013.01); *A61B 90/06* (2016.02);
(Continued)

(58) Field of Classification Search
CPC ................ A61B 19/38; A61B 17/0293; A61B 2019/385; A61L 2202/12; A61L 2202/24;
(Continued)

(56) References Cited

U.S. PATENT DOCUMENTS 5,015,243 A    5/1991    Schifano
5,037,395 A    8/1991    Spencer
(Continued)

OTHER PUBLICATIONS

Arnold et al., "Use of Negative Air Ionization for Reducing Microbial Contamination on Stainless Surfaces", Journal of Applied Poultry Research, vol. 11, Poultry Science Association, 2002—pp. 179-186.
(Continued)

*Primary Examiner* — Wyatt A Stoffa
(74) *Attorney, Agent, or Firm* — RatnerPrestia

(57) ABSTRACT

Apparatus, system, and methods are provided for reducing infectious agents at a sterile site by preventing infectious agents from coming into contact with the sterile site. A barrier is produced for infectious agents that may come in proximity or otherwise communicate with the site. The apparatus is configured to create a void-free barrier in which infectious agents are reduced with minimal exposure of potentially harmful effects of the barrier to the sterile site, objects, or users of the apparatus.

5 Claims, 48 Drawing Sheets

Related U.S. Application Data division of application No. 14/384,557, filed as application No. PCT/US2013/030815 on Mar. 13, 2013, now Pat. No. 9,615,884.

(60) Provisional application No. 61/610,840, filed on Mar. 14, 2012.

(51) Int. Cl.

| | | |
|---|---|---|
| A61L 2/02 | (2006.01) | |
| A61L 2/08 | (2006.01) | |
| A61B 17/02 | (2006.01) | |
| A61L 2/03 | (2006.01) | |
| A61B 90/00 | (2016.01) | |
| A61L 2/06 | (2006.01) | |
| A61L 2/14 | (2006.01) | |
| A61B 17/00 | (2006.01) | |

(52) U.S. Cl.
CPC ........ *A61L 2/02* (2013.01); *A61L 2/03* (2013.01); *A61L 2/06* (2013.01); *A61L 2/08* (2013.01); *A61L 2/10* (2013.01); *A61L 2/14* (2013.01); *A61B 2017/00022* (2013.01); *A61B 2090/401* (2016.02); *A61L 2202/12* (2013.01); *A61L 2202/24* (2013.01)

(58) Field of Classification Search
CPC ..... A61L 2/02; A61L 2/03; A61L 2/08; A61L 2/10
See application file for complete search history.

(56) References Cited

U.S. PATENT DOCUMENTS

| | | | |
|---|---|---|---|
| 5,154,165 A | 10/1992 | Elliott et al. | |
| 6,254,625 B1 | 7/2001 | Rosenthal et al. | |
| 6,283,986 B1 | 9/2001 | Johnson | |
| 6,494,858 B1* | 12/2002 | van der Linden | A61B 90/40 604/23 |
| 6,513,529 B1 | 2/2003 | Kamen | |
| 6,810,288 B2* | 10/2004 | Joshi | A61M 35/30 607/50 |
| 8,142,713 B2 | 3/2012 | Gordon | |
| 8,318,090 B2* | 11/2012 | Gordon | A61L 2/10 422/22 |
| 9,545,463 B2* | 1/2017 | Blott | A61M 27/00 |
| 9,615,884 B2* | 4/2017 | Armour | A61L 2/03 |
| 9,950,100 B2* | 4/2018 | Blott | A61F 13/00068 |
| 10,039,868 B2* | 8/2018 | Blott | A61M 1/85 |
| 10,207,035 B2* | 2/2019 | Weston | A61F 13/0216 |
| 10,299,882 B2* | 5/2019 | Armour | A61B 17/0293 |
| 2003/0155524 A1* | 8/2003 | McDonald | C02F 1/325 250/435 |
| 2004/0175290 A1* | 9/2004 | Scheir | A23L 3/28 422/24 |
| 2006/0293630 A1* | 12/2006 | Manna | A61B 17/3431 604/327 |
| 2007/0119461 A1* | 5/2007 | Biancucci | A61B 17/12172 128/846 |
| 2007/0176117 A1 | 8/2007 | Redmond et al. | |
| 2007/0213645 A1 | 9/2007 | Zumeris et al. | |
| 2007/0276191 A1* | 11/2007 | Selover | A61B 17/3421 600/245 |
| 2008/0017564 A1 | 1/2008 | Hammond | |
| 2008/0159908 A1* | 7/2008 | Redmond | A61L 2/10 422/24 |
| 2008/0161749 A1* | 7/2008 | Houghton-Ward | A61M 13/00 604/23 |
| 2009/0054853 A1* | 2/2009 | Huyser | A61B 17/02 604/264 |
| 2009/0143718 A1 | 6/2009 | Jiang et al. | |
| 2009/0257910 A1* | 10/2009 | Segal | A61L 2/10 422/22 |
| 2010/0064456 A1* | 3/2010 | Ferlic | A61M 39/20 15/104.94 |
| 2010/0222852 A1 | 9/2010 | Vasily et al. | |
| 2010/0234794 A1 | 9/2010 | Weadock et al. | |
| 2010/0266446 A1 | 10/2010 | Constantacos | |
| 2010/0268249 A1 | 10/2010 | Stuart | |
| 2010/0280436 A1 | 11/2010 | Self et al. | |
| 2011/0015575 A1* | 1/2011 | Perez | A61B 17/3401 604/164.01 |
| 2011/0021879 A1* | 1/2011 | Hart | A61B 17/0293 600/207 |
| 2011/0079732 A1* | 4/2011 | Kreitenberg | A63B 47/04 250/455.11 |
| 2011/0178510 A1* | 7/2011 | Cumbie | A61L 2/10 606/3 |
| 2011/0290257 A1* | 12/2011 | Hillis | A61B 90/40 128/847 |
| 2012/0056102 A1* | 3/2012 | Stanley | A61L 2/10 250/455.11 |
| 2012/0248332 A1* | 10/2012 | Kreitenberg | A63B 47/04 250/455.11 |
| 2012/0277662 A1* | 11/2012 | Golkowski | A61L 2/00 604/24 |
| 2012/0321509 A1* | 12/2012 | Bak | A61M 39/16 422/24 |
| 2013/0099081 A1* | 4/2013 | Agbodoe | F16M 11/40 248/276.1 |
| 2013/0217975 A1* | 8/2013 | Selover | A61B 1/3135 600/245 |
| 2013/0284183 A1* | 10/2013 | Hillis | A61M 35/30 128/847 |
| 2014/0163326 A1* | 6/2014 | Forsell | A61B 90/40 600/207 |
| 2016/0287348 A1* | 10/2016 | Vayser | A61B 1/0661 |

OTHER PUBLICATIONS

Centers for Disease Control, Types of Healthcare-associated Infections, http://www.cdc.gov/HAI/infectionTypes.html, 2019—3 pages.
Escombe et al., "Upper-Room Ultraviolet Light and Negative Air Ionization to Prevent Tuberculosis Transmission", PLoS Medicine (Public Library of Science), vol. 6, Issue 3, Mar. 2009—12 pages.
Farrell et al., "Investigation of Critical Inter-related Factors Affecting the Efficacy of Pulsed Light for Inactivating Clinically Relevant Bacterial Pathogens", Journal of Applied Microbiology, 106, 2010—pp. 1494-1508.
Food and Drug Administration, "Kinetics of Microbial Inactivation for Alternative Food Processing Technologies Pulsed Light Technology", http://www.fda.gov/Food/ScienceResearch/ResearchAreas/SafePraticesforFoodProcesses/ucm103058.htm, 2000, 108 pages.
Heinlin et al., "Plasma Medicine: Possible Applications in Dermatology", JDDG, 2010, 8-9 pages.
International Preliminary Report on Patentability and Written Opinion for International Application No. PCT/US2013/030815, dated Sep. 16, 2014—10 pages.
International Search Report for International Application No. PCT/US2013/030815, dated Jul. 18, 2013—5 Pages.
Lamont et al., "Pulsed UV-light Inactivation of Poliovirus and Adenovirus", Letters in Applied Microbiology 45, 2007—pp. 564-567.
Moraru et al., "Effect of Spectral Range in Surface Inactivation of Listeria Innocua Using Broad Spectrum Pulsed Light", Journal of Food Protection, vol. 70, No. 4, 2007—pp. 909-916.
Slaybaugh, R., "Sterilization: Gas Plasma, Steam, and Washer-decontamination", http://infectioncontroltoday.com, Virgo Publishing, Jun. 2000—12 pages.
Ueda et al., "Simultaneous Treatment of Washing, Disinfection and Sterilization Using Ultrasonic Levitation, Silver Electrolysis and Ozone Oxidation", Biocontrol Science, 2009, vol. 14, No. 1—pp. 1-12.
Uslan, D., "Overview of Infections of Cardiac Rhythm Management Devices", EP Lab Digest, Supplement to May 2009—12 pages.

(56) References Cited

OTHER PUBLICATIONS

Vaze et al., "Inactivation of Bacteria in Flight by Direct Exposure to Northermal Plasma", IEEE Transactions on Plasma Science, vol. 36, No. 11, Nov. 2010—pp. 3234-3240.
World Health Organization, Practical Guidelines for Infection Control in Health Care Facilities, SEARO Regional Publication, No. 41, 2004—110 pages.

* cited by examiner

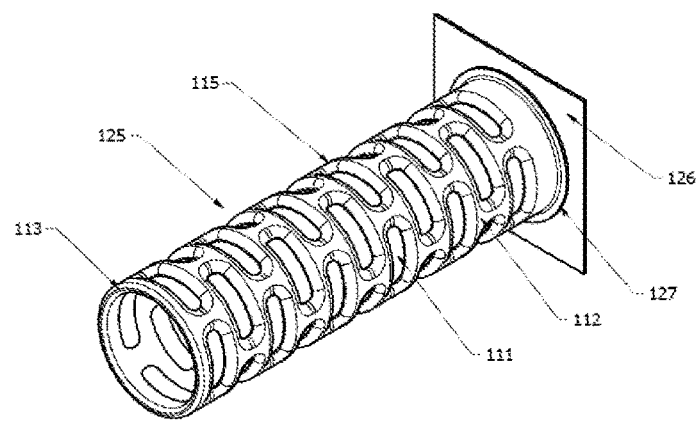
FIG. 16
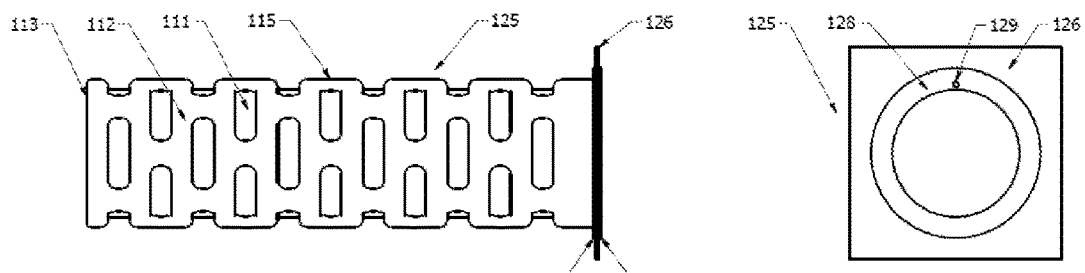
FIG. 17
FIG. 18
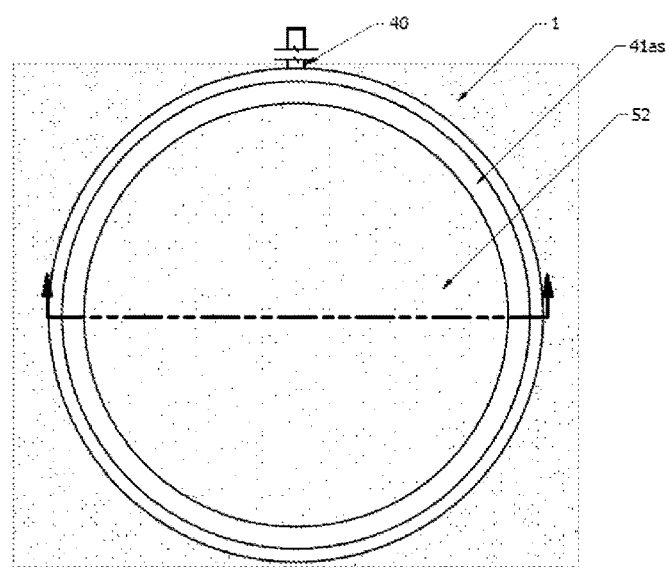
FIG. 19
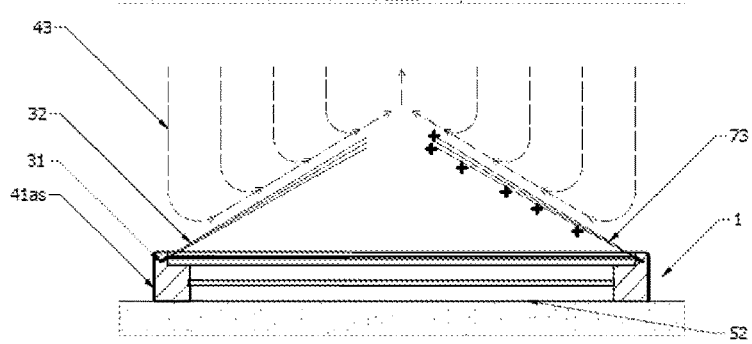
FIG. 20

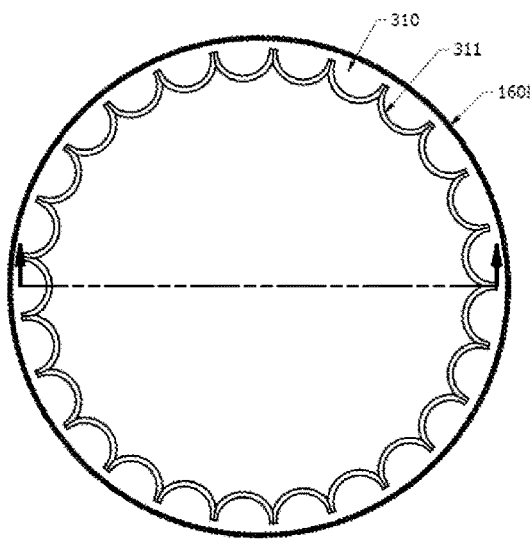
FIG. 113
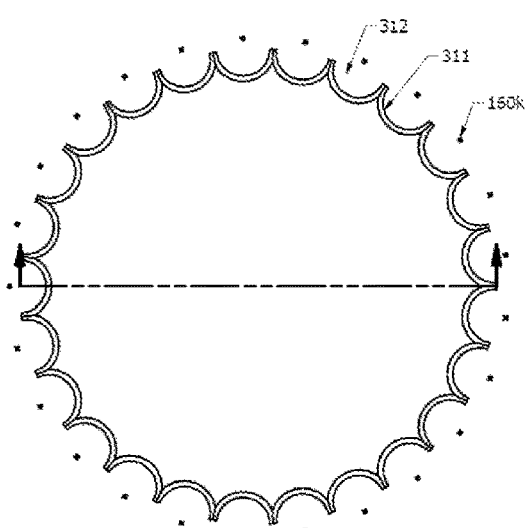
FIG. 115
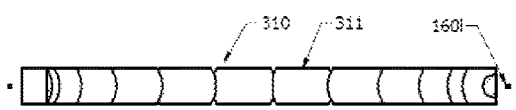
FIG. 114
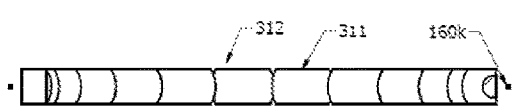
FIG. 116
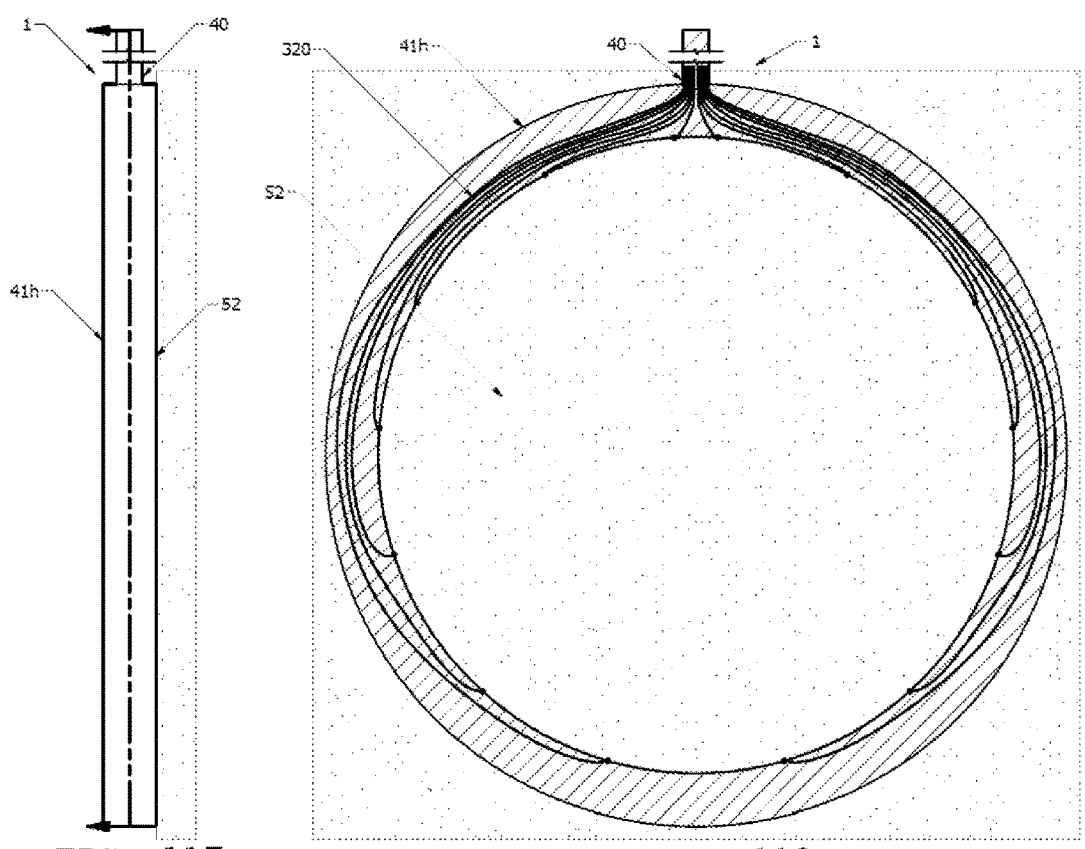
FIG. 117
FIG. 118

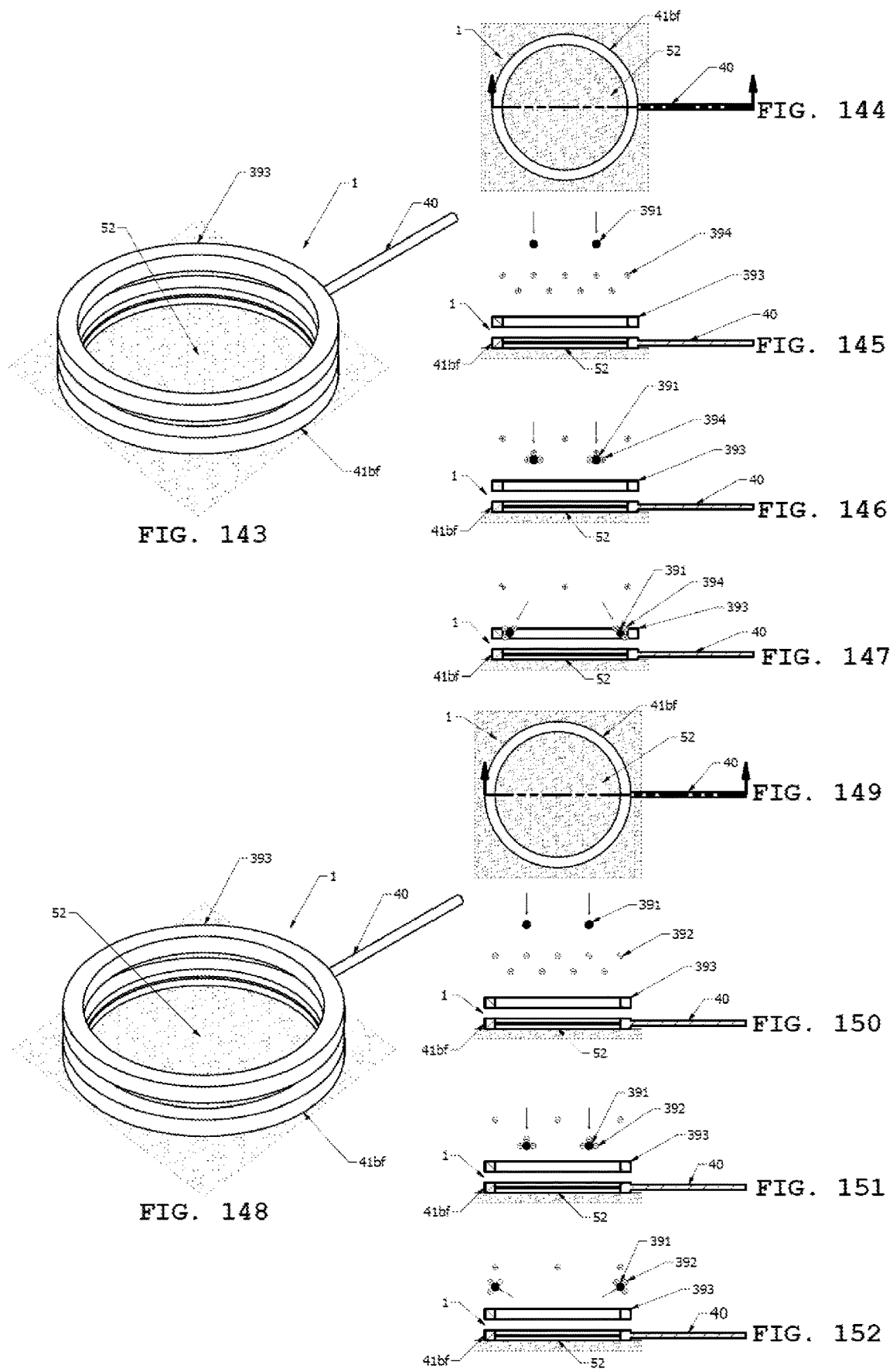

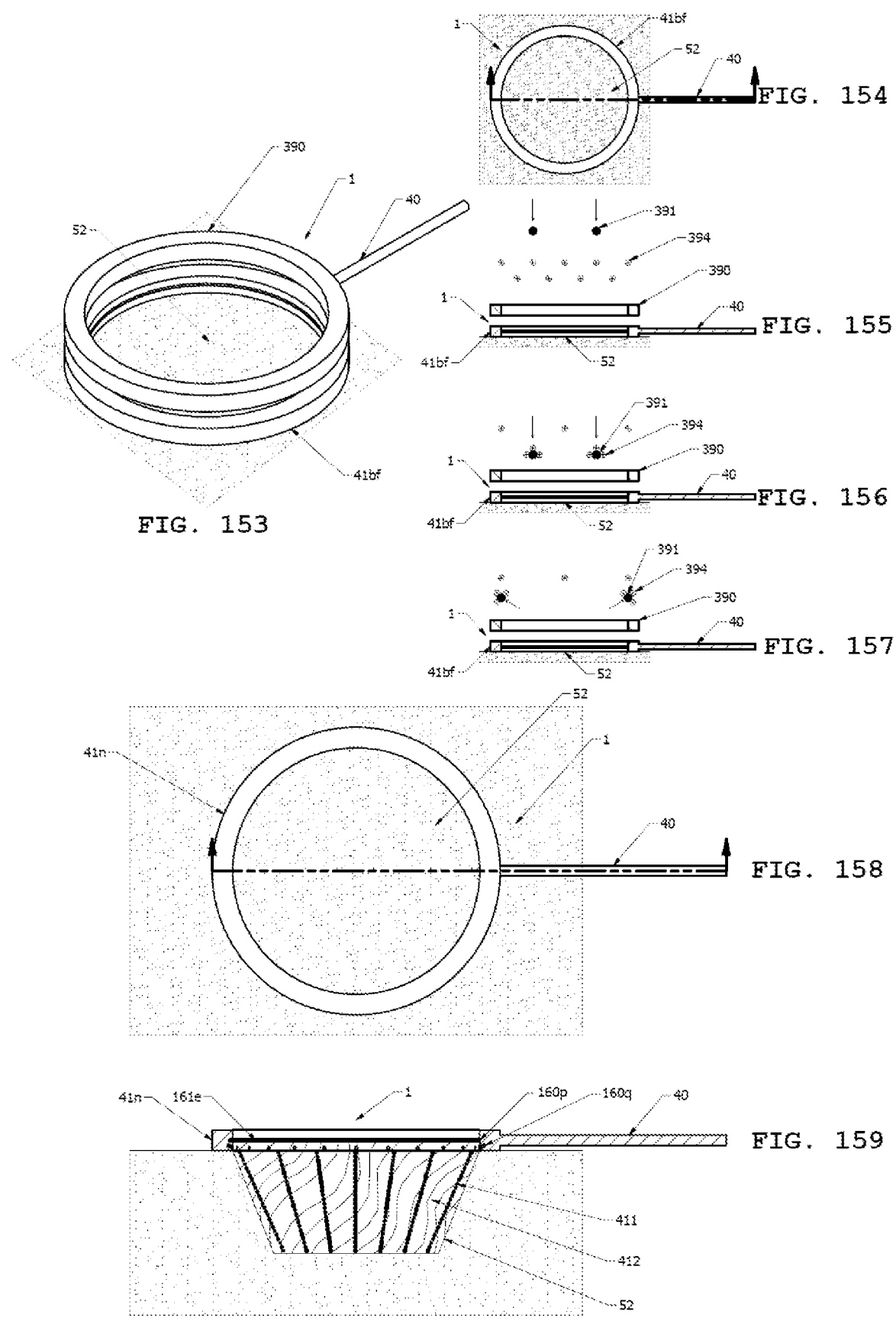

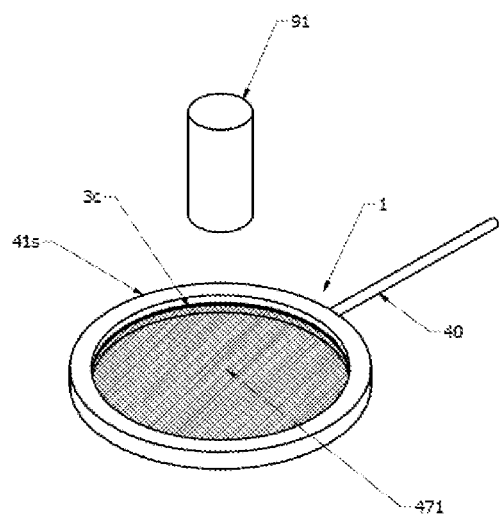
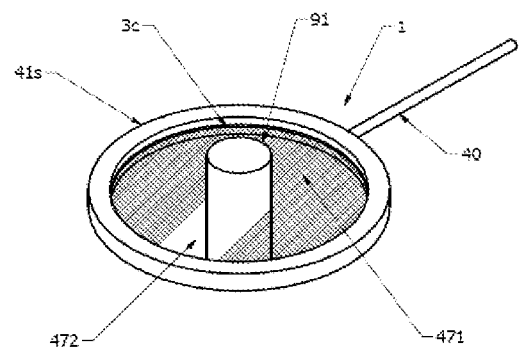
FIG. 171    FIG. 172
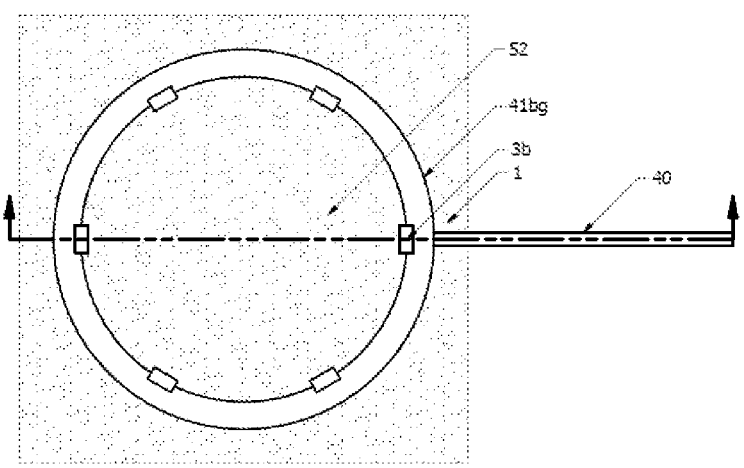
FIG. 173
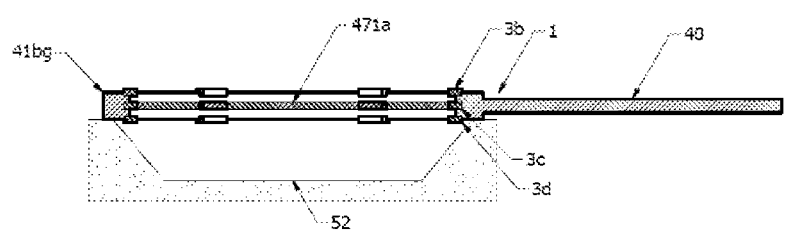
FIG. 174

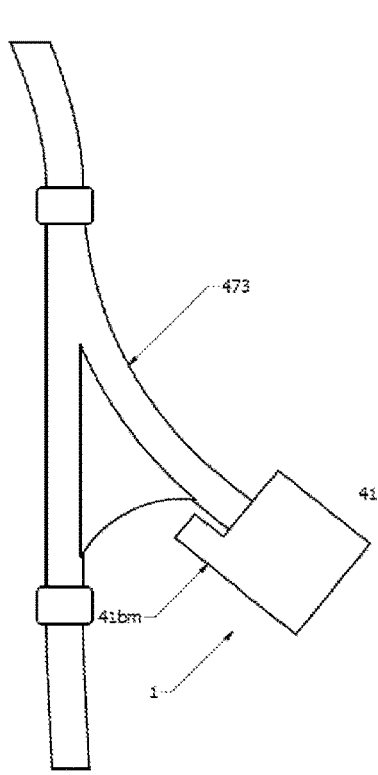
FIG. 211
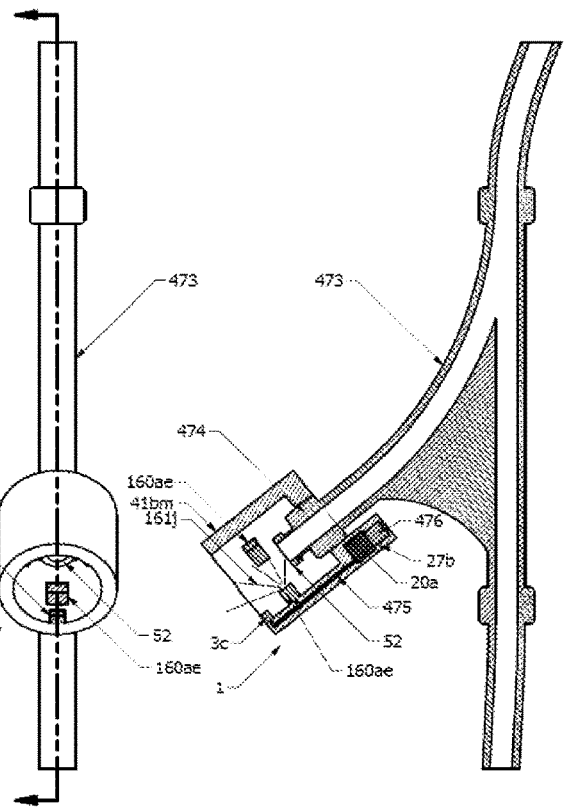
FIG. 212
FIG. 213
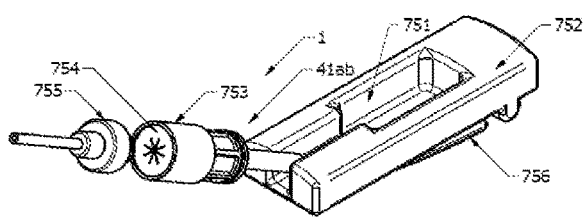
FIG. 214
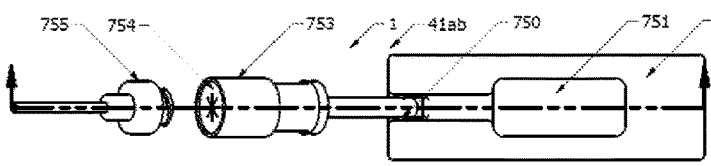
FIG. 215
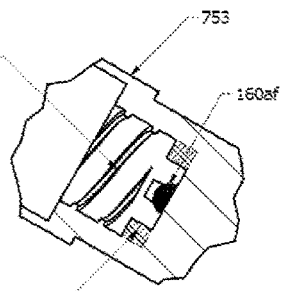
FIG. 217
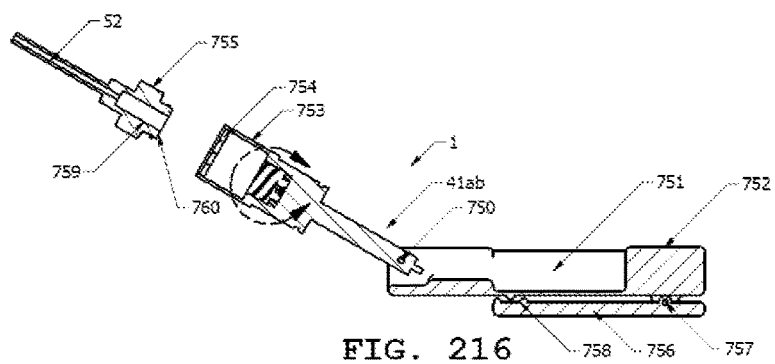
FIG. 216

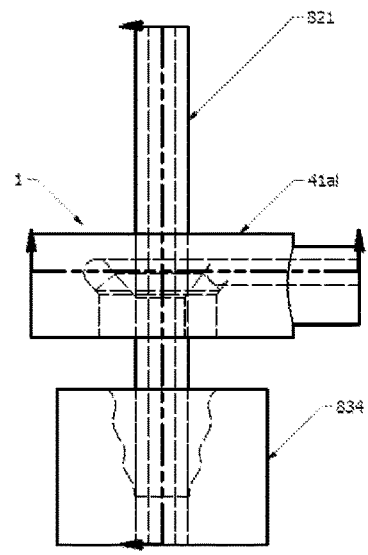
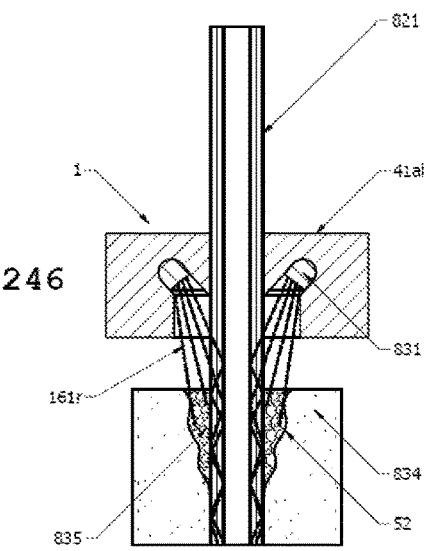
FIG. 246
FIG. 248
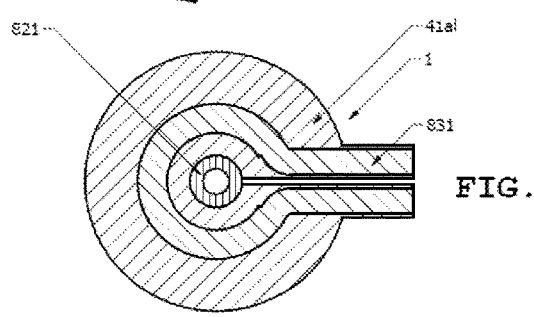
FIG. 247
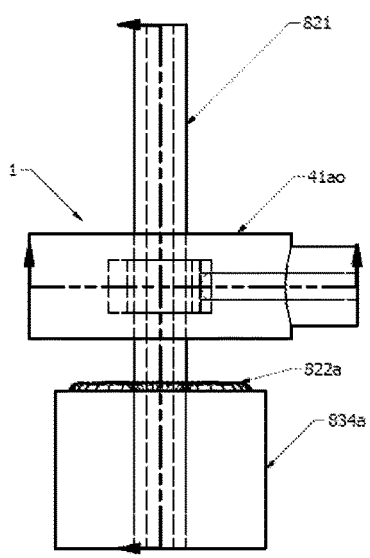
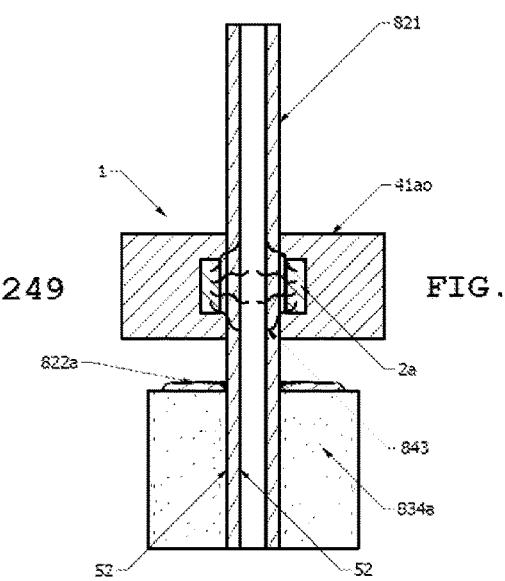
FIG. 249
FIG. 251
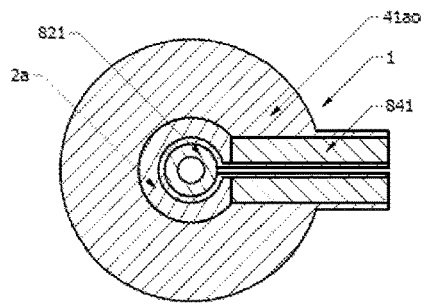
FIG. 250

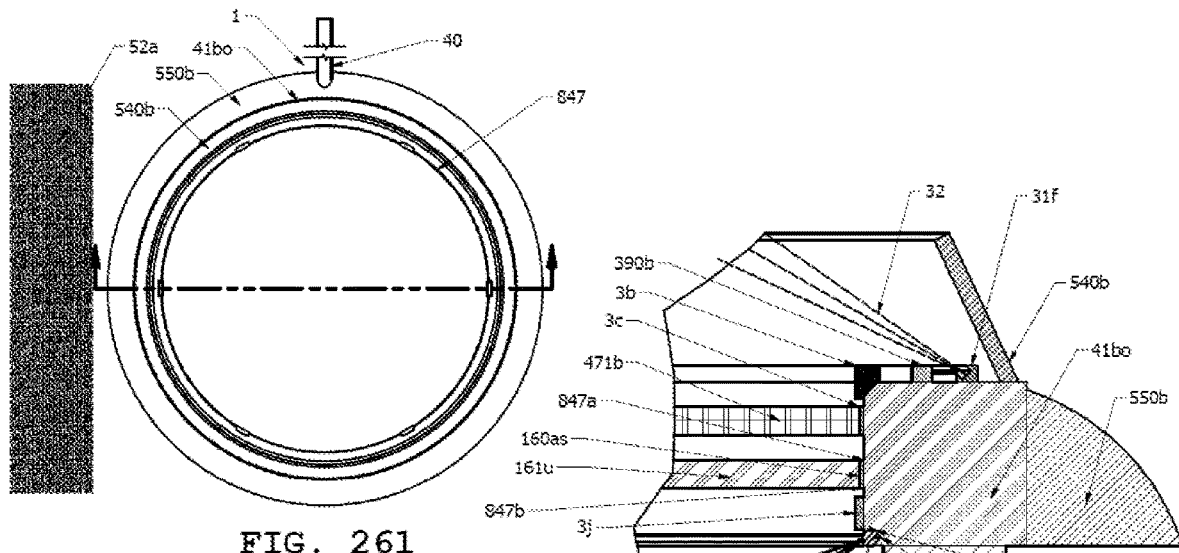
FIG. 261
FIG. 262
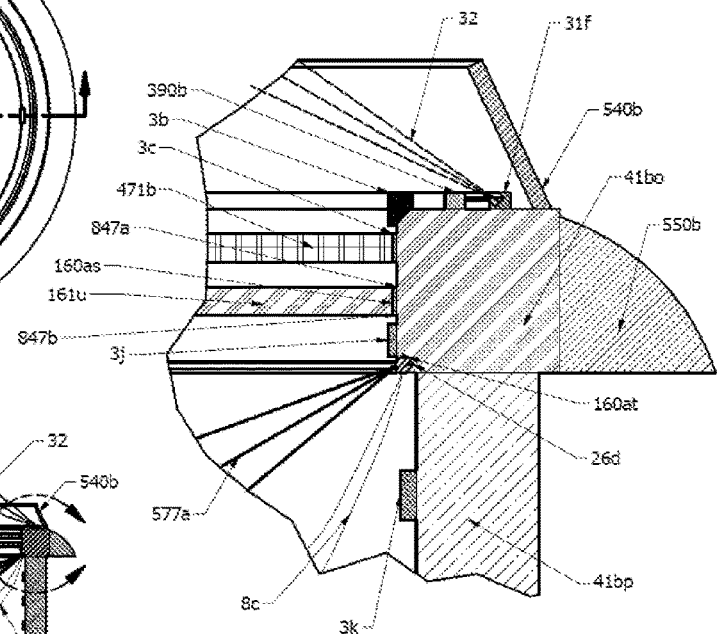
FIG. 263
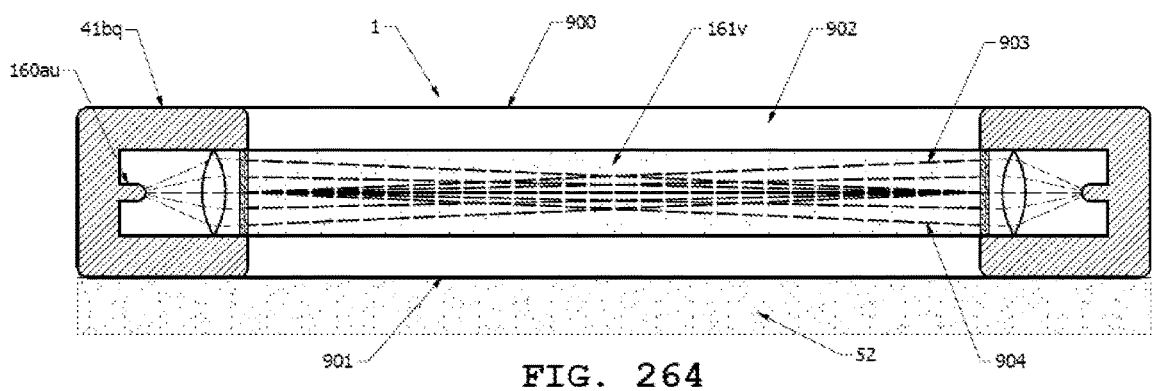
FIG. 264

STERILE SITE APPARATUS, SYSTEM, AND METHOD OF USING THE SAME

CROSS REFERENCE TO RELATED APPLICATION

This application is a Continuation Application of application Ser. No. 15/443,860, filed Feb. 27, 2017, which is a Divisional Application of application Ser. No. 14/384,557, which is the U.S. National Phase application of PCT International Application No. PCT/US2013/030815, filed Mar. 13, 2013, and claims priority to provisional application Ser. No. 61/610,840, filed Mar. 14, 2012, each of which applications is incorporated herein by reference in their entireties and for all purposes.

FIELD OF THE INVENTION

This invention relates generally to an apparatus, system, and method for the reduction of infectious agents at a sterile site, and more specifically to apparatuses, systems, and methods which create a barrier in order to inhibit sterile site contamination.

BACKGROUND OF THE INVENTION

Healthcare associated infections (HAIs) result in a significant cause of morbidity and mortality in the United States. In 2002, the estimated number of HAIs in U.S. hospitals, adjusted to include federal facilities, was approximately 1.7 million. The overall annual direct medical costs of HAI to U.S. hospitals ranges from $28.4 to $33.8 billion.

The most significant types of HAIs are central line-associated bloodstream infection (CLABSI), Clistridium difficile Infection (CDI, C. diff), Surgical Site Infection (SSI), Catheter-associated urinary tract infection (CAUTI), and Ventilator-associated pneumonia (VAP) which combined account for roughly two thirds of all HAIs in the US. The Centers for Disease Control and Prevention (CDC) provide substantial information and resources in characterizing these and other infections. This information may be found at http://www.cdc.gov/HAI/infectionTypes.html and is incorporated into the background by reference.

In general, HAIs arise from patient- and procedure-specific risk factors. Host-specific factors include patient co-morbidities such as hemodialysis, diabetes, or age. Such inherent risk factors are not easily modifiable, with little opportunity for intervention to reduce infection risks. See, Uslan, Daniel Z. Overview of Infections of Cardiac Rhythm Management Devices. EP Lab Digest, Supplement to May 2009. Procedure-associated risks correlate with a high rate of surgical site infection (SSI) and catheter related infections due to factors such as inpatient or outpatient treatment, length of procedure time, and venue of surgical theatre (operating room or catheterization lab). In addition, there are also infection risks related to the use of biotechnology, in which the patient is susceptible to exposure from diagnostic equipment (endoscope/laparoscope) and implants (hip prosthesis, cardiac rhythm management devices/CRMDs), including both autograft and allograft transplants.

All surgical procedures involve a small but serious risk of infection. However, infections involving CRMDs are specifically difficult to resolve due to the presence of prosthetic material within the body. CRMD infections result in a substantial cost to the healthcare system because the implanted hardware must be extracted and replaced. See, Reynolds, Matthew R. The Health Economic Consequences of Cardiac Rhythm Device Infections. EP Lab Digest, Supplement to May 2009. Reducing or preventing HAI's are a function of reducing infectious agents colonizing in an area that can result in an infection to the body.

Adherence to the principles of sterile technique is crucially important in achieving asepsis in the operating room complex. Prior to reprocessing to achieve disinfection or sterility, any instrument or equipment must be properly cleaned using the following: a detergent or enzymatic cleaner, an ultrasonic cleaner, or an automated washer. Disinfection involves the physical or chemical cleaning which renders an object or surface free from dangerous microbial life, allowing it to be safely handled. Sterilization is the process of eradicating all evidence of live micro-organisms, including spores. The integrity of the surgical site is preserved by keeping the surgical team gowned and gloved, with the use of sterile items confined to the level of table height within the sterile field, which is created as close as possible to the time of use. During a surgical intervention, sterile persons must touch only sterile items; they must also remain within the sterile area and avoid reaching over an unsterile area.

Despite compliance to rigorous infection control protocols, micro-organisms with nosocomial infection potential are still present in the hospital environment: *Clostridium Difficile*, Methicillin-Resistant *Staphylococcus Aureus, Staphylococci, Enterococci, Pseudomonas, Streptococci*, and Vancomycin-Resistant *Enterococcus*. See, Malan, Kim. Registered Nurses' Knowledge of Infection Control and Sterile Technique Principles in the Operating Room Complex of Private Hospitals. Nelson Mandela Metropolitan University. 2009. This may be explained by a 2009 study which evaluated sanitation procedures in operating rooms; it established that after cleaning, the post sanitation bacterial load resumed an increase in levels of total microbial count, depending on the material of the surface and its horizontal or vertical disposition. See, Fabretti, Alessia, PhD, et al. Experimental Evaluation of the Efficacy of Sanitation Procedures in Operating Rooms. Association for Professionals in Infection Control and Epidemiology, Inc. 2009.

Due to the resurgence of micro-organisms which contribute to SSI, different apparatuses and methods have been developed to enhance sanitation levels in the operating complex. Instruments which cannot be sterilized must be disinfected using thermal pasteurization or chemical inactivation. Pasteurization is not compatible with all instruments, as it requires a high tolerance for heat and moisture processing. The practice of chemical disinfection also encounters some limitations; only instrument-grade disinfectants are suitable for use with medical instruments and equipment. Glutaraldehyde is most effective for inactivating all microbial pathogens except where there is a large presence of bacterial spores, but it must be used under strictly controlled conditions in a safe working environment. See, World Health Organization. Practical Guidelines for Infection Control in Health Care Facilities. *SEARO Regional Publication* No. 41. 2004. The CDC has published a comprehensive reference entitled Guideline for Disinfection and Sterilization in Healthcare Facilities, 2008 which is included in its entirety by reference herein.

Medical devices which penetrate sterile body sites must be sterilized through either physical or chemical methods to eliminate all micro-organisms. The most common physical method for sterilization involves using heat to oxidize the proteins in microbes. However, the dry heat which is produced by incineration devices such as the Bunsen burner or the hot-air oven take several hours to achieve sterilization.

Moist heat can also destroy micro-organisms using boiling water, pasteurization, autoclaving, or tyndallization. While these techniques are able to kill microbes by denaturing their proteins, they also require many hours to eliminate bacterial spores.

A few physical methods which control the growth and presence of micro-organisms do not involve heat. Filtration is a process by which liquids or gases are passed through a series of pores small enough to trap the micro-organisms. The filtration medium may be comprised of nitrocellulose membranes or diatomaceous earth. Drying is a process which eradicates microbes by removing water from their cells. Another technique for drying involves lyophilization, which quick freezes liquids and then subjects them to evacuation. While cold temperatures can slow down bacterial growth, freezing temperatures kill many micro-organisms by forming ice crystals. These various methods all require an investment of time to perform some repetitive cycling of the process while the microbes are eradicated. See, Alcamo, I. Edward, PhD. Cliffs Quick Review Microbiology. Wiley Publishing. 1996.

The use of radiation also provides a physical form of sterilization. Radiation can be emitted in different forms such as microwave, ultraviolet (UV) light, pulsed UV, broad spectrum pulsed light (BSPL) electron beam, and pulsed electrical field (PEF). The direct effect of microwave on microbes is minimal; water molecules will vibrate at the microwave frequency, creating heat. This high temperature is the agent which atomizes the micro-organism and kills it, rather than the microwave itself. Though not a form of radiation, ultrasonic atomization is similar to microwave atomization in that a shock wave is used to induce the expansion of water droplets, which would then atomize any bioaerosols in the airstream.

A common form of radiation involves the use of UV light emitted from a mercury lamp, which is directed as a single photon that can penetrate a micro-organism and disassociate its DNA. Shortwave ultraviolet light, or germicidal UV-C, can kill bacteria at a wavelength between 200-280 nm. It is commonly employed at 254 nm for air, water, and surface disinfection, but the lethal wavelength to inactivate micro-organisms varies with the kind of bacteria, spores, viruses, mold, yeast, and algae, as well as their exposure time to that specific intensity. See, Andersen, B. M., MD, PhD, et al. Comparison of UV C Light and Chemicals for Disinfection of Surfaces in Hospital Isolation Units. *Infection Control and Hospital Epidemiology*. July 2006. Higher wavelengths penetrate the contaminated surface more thoroughly, but more intense radiation produces more heat, which may not be suitable for all sterilization applications.

As a source of UV radiation, an alternative to continuous mercury lamps is the pulsed xenon arc or xenon flashlamp. Compared to continuous wave sources such as mercury lamps, the pulsed xenon flashlamp is more efficient in its conversion of electrical energy to light energy, while its output of light intensity in the critical 200-300 nm wavelength region is substantially greater. See, Lamont, Y. et al. Pulsed UV-light inactivation of poliovirus and adenovirus. *Letters in Applied Microbiology* 45, 2007, pages 564-567. This technology kills micro-organisms by emitting very brief pulses of an intense broadband emission spectrum which is rich in UV-C germicidal light. A continuous 10 W mercury lamp would have to be operated for 10 seconds to achieve the same sterility level as a 1 MW pulsed xenon lamp operated for just 100 μs. See, Farrell, H. P. et al. Investigation of critical inter-related factors affecting the efficacy of pulsed light for inactivating clinically relevant bacterial pathogens. *Journal of Applied Microbiology* 106, 2010, pages 1494-1508. In 1996, the Food and Drug Administration approved the use of pulsed light technology for microbial inactivation for alternative food processing technology under the condition that xenon flashlamps are used as the pulse light source and the cumulative treatment does not exceed 12 J/$cm^2$. See, Woodling, Sarah and Carmen Moraru. Effect of Spectral Range in Surface Inactivation of *Listeria Innocua* Using Broad-Spectrum Pulsed Light. *Journal of Food Protection*. Vol 70, No. 4, 2007, pages 909-916. Pulsed light radiation involves the use of intense and short duration of broad-spectrum "white light," which includes wavelengths in the ultraviolet, through the visible, to the near infrared region. In one commercial application acknowledged by the FDA, the material to be disinfected is exposed to at least 1 pulse of light having a range of energy density between 0.01 to 50 J/$cm^2$ at the surface. Each pulse of light is typically comprised of 1 to 20 flashes per second. The wavelength is distributed so that at least 70% of the electromagnetic energy is within the broad spectrum range of 170 to 2600 nm. Broad spectrum pulsed light (BSPL) can be delivered at an intensity which is 20,000 times greater than sunlight at the earth's surface, though the intense flashes of light may be less than 1 millisecond in duration. Because several pulses can be generated per second, BSPL can perform sterilization at a faster rate than other conventional processes for physical sterilization, and its efficacy has been tested against a broad range of micro-organisms, including bacteria, spores, fungi, viruses, and protozoa. See, Food and Drug Administration. Kinetics of Microbial Inactivation for Alternative Food Processing Technologies—Pulsed Light Technology. http://www.fda.gov/Food/ScienceResearch/ResearchAreas/SafePracticesforFoodProcess es/ucm103058.htm.

Another alternative source of UV radiation is the light emitting diode (LED), though until recently, LED's lacked the efficiency and longevity to be effective for sterilization. Recent developments from companies like UV Craftory Co (Aichi, Japan), crystal IS (Green Island, N.Y.), and Sensor Electronic Technology, Inc. (Columbia, S.C.) have enabled UV LED technology to be more practical for commercial applications. The benefits are low heat generation, low power consumption, instant on and off control, and the ability to produce narrow wavelength distributions in the UV-A, UV-B, and UV-C spectrums. A narrow wavelength distribution in the UVC spectrum is especially useful when there is concern for the safety of the radiation in contact with the user or sterile site.

Yet another alternative source of UV radiation is a UV laser, where coherent UV radiation is produced by a laser diode, an excimer laser, or any other viable means of producing UV radiation that has limited diffraction and whose phase is relatively correlated along the beam. The advantage to using UV-C to disinfect surfaces is that it requires a relatively short exposure time without necessary manual labor. UV-C also has little impact on the environment; it leaves no residues and does not produce drug-resistant micro-organisms. However, UV-C may cause some degradation over time on various materials including plastics and rubbers. It also has the disadvantage of possessing a low penetrating effect (1-2 mm), so measures must be taken to reduce any shadowing in the surgical field.

Ultraviolet Dosage Required
For 99.9% Destruction of Various Organisms
($\mu$W-s/cm$^2$ at 254 nanometer)

| Bacteria | |
|---|---|
| Bacillus anthracis | 8,700 |
| B. enteritidis | 7,600 |
| B. Megatherium sp. (vegatative) | 2,500 |
| B. Megatherium sp. (spores) | 52,000 |
| B. paratyphosus | 6,100 |
| B. subtilis (vegatative) | 11,000 |
| B. subtilis (spores) | 58,000 |
| Clostridium tetani | 22,000 |
| Corynebacterium diphtheria | 6,500 |
| Eberthella typhosa | 4,100 |
| Escherichia coli | 7,000 |
| Leptospira interrogans | 6,000 |
| Micrococcus candidus | 12,300 |
| Micrococcus sphaeroides | 15,400 |
| Mycobacterium tuberculosis | 10,000 |
| Neisseria catarrhalis | 8,500 |
| Phytomonas tumefaciens | 8,500 |
| Proteus vulgaris | 6,600 |
| Pseudomonas aeruginosa | 10,500 |
| Pseudomonas fluorescens | 6,600 |
| Salmonella enteritidis | 7,600 |
| Salmonella paratyphi | 6,100 |
| Salmonella typhimurium | 15,200 |
| Salmonella typhosa (Typhoid) | 6,000 |
| Sarcina lutea | 26,400 |
| Serratia marcescens | 6,200 |
| Shigella dysenteriae (Dysentery) | 4,200 |
| Shigella paradysenteriae | 3,400 |
| Spirillum rubrum | 6,160 |
| Staphylococcus albus | 5,720 |
| Staphylococcus aurens | 6,600 |
| Streptococcus hemolyticus | 5,500 |
| Streptococcus lactis | 8,800 |
| Streptococcus viridans | 3,800 |
| Vibrio cholerae | 6,500 |
| Mold Spores | |
| Aspergillus flavus | 99,000 |
| Aspergillus glaucus | 88,000 |
| Aspergillus niger | 330,000 |
| Mucor racemosus A | 35,200 |
| Mucor racemosus B | 35,200 |
| Oospora lactis | 11,000 |
| Penicillium digitatum | 88,000 |
| Penicillium expansum | 22,000 |
| Penicillium roqueforti | 26,400 |
| Rhizopus nigricans | 220,000 |
| Algae/Protozoa | |
| Chlorella vulgaris (algae) | 22,000 |
| Nematode eggs | 92,000 |
| Paramecium | 200,000 |
| Virus | |
| Bacteriophage (E. coli) | 6,600 |
| Hepatitis virus | 8,000 |
| Influenza virus | 6,600 |
| Polio virus | 6,000 |
| Rotavirus | 24,000 |
| Tobacco mosaic | 440,000 |
| Yeast | |
| Baker's yeast | 8,800 |
| Brewer's yeast | 6,600 |
| Common yeast cake | 13,200 |
| Saccharomyces cerevisiae | 13,200 |
| Saccharomyces ellipsoideus | 13,200 |
| Saccharomyces sp. | 17,600 |

Another application of radiation as a physical form of sterilization involves the use of pulsed electrical field (PEF), which is produced when high-voltage electrodes are charged and discharged in fractions of a second. PEF has been used to induce microbial inactivation by creating a disruption of cell membranes in micro-organisms. This process emits an intense electrical field which exceeds the cell's critical transmembrane potential. The efficacy of PEF for use in sterilization is affected by many factors such as the intensity of the electric field, the number of pulses, the pulse duration, the processing temperature, the type of organism, the electrical conductivity, and the pH of the medium or contact surface. See, Wesierska, Ewelina and Tadeusz Trziszka. Evaluation of the use of pulsed electrical field as a factor with antimicrobial activity. *Journal of Food Engineering* 78. pp. 1320-1325. 2007. The shape of the wave pulse is also an important variant; electric field pulses may be applied in several forms: exponential decays, square waves, oscillatory, bipolar, or instant reverse charges. For microbial inactivity, oscillatory pulses are the least efficient, while square wave pulses are more lethal and energy efficient than exponential decaying pulses. Bipolar pulses are more destructive to micro-organisms than monopolar pulses because a PEF causes charged molecules to move within their cell membranes. A reverse orientation in the polarity of the field causes the molecules to change directions, so that the alternating bipolar pulses create stresses in the cell membrane which contribute to its electrical disintegration. The instant reverse charge is a pulse which is partially positive at the moment of initiation but then becomes partially negative directly afterward. An increase in the electrical conductivity of the treated medium will decrease both the positive and the negative intervals of the pulse, producing an increase in the overall peak voltage ratio. Compared to other pulse waveforms, the instant reverse charge can be 5× more efficient for inactivating micro-organisms.

Cold atmospheric plasma (CAP) has also been used successfully for sterilization without damaging healthy tissue. Numerous components of the plasma including reactive oxygen or nitrogen species, charged particles, electric fields, and UV radiation are involved in these effects. Both physical mechanisms caused by reactive species, free radicals, and UV photons, as well as biological mechanisms are thought to be responsible for the inactivation of bacteria. See, Heinlin, Julia, et al. Plasma medicine: possible applications in dermatology. JDDG; 2010 8, page 1. CAP also has the benefit of stimulating wound healing, and has been used successfully in reducing the time for surgical wounds to heal while minimizing scarring.

Chemical methods for controlling microbial growth involve the use of phenol, halogens such as iodine and chlorine, alcohols, heavy metals, aldehydes, ethylene oxide, and oxidizing agents such as nitric oxide, nitrogen dioxide, hydrogen peroxide, benzoyl peroxide, and ozone. Due to their ease of use, chemicals have been vastly employed for sterilization. However, they may result in adverse effects by altering the nature of treated surfaces or by propagating odorous reactions or biohazardous substances. See, Mori, Mirei, et al. Development of a new water sterilization device with a 365 nm UV-LED. *Medical and Biological Engineering and Computing*. 2007.

Antimicrobial drugs are chemicals which kill microorganisms or inhibit their growth. By damaging the plasma membrane or interfering with DNA replication and transcription, by disrupting the synthesis of nucleic acids, proteins, or metabolic products, these drugs destroy pathogens through cell lysis. The disadvantage to using antimicrobial agents is that these drugs attack not only the infectious organisms, but the indigenous flora as well, compromising the host's normal defensive capacity. Broad spectrum antimicrobials target pathogenic organisms as well as microorganisms in the host. However, in some instances, a competing micro-organism may develop resistance against the antimicrobial drug, resulting in its overgrowth. See, Research and Education Association. Microbiology Super Review. REA. 2006.

Recent developments in technology to prevent SSI have resulted in a combination of physical and chemical sterilization techniques. This may have been motivated by the emergence of more sophisticated medical instruments and devices which are sensitive to heat and moisture, and thus inspired the creation of low temperature alternatives to steam and dry heat sterilization processes. Ethylene oxide (EtO), which was introduced in the early 1950s, has been the standard among hospitals for low temperature sterilization. Though it is a very effective microbiocidal agent, EtO is an odorless, colorless gas which can become toxic if handled improperly. It also requires a cycle time of 8-12 hours. No other suitable alternative was available until paracetic acid was introduced in 1988. However, instruments sterilized with paracetic acid must be used immediately, creating a dependence on "just-in-time processing." See, Ackert-Burr, Cheri, RN, MSN. Low Temperature Sterilization: Are You In The Know? Perioperative *Nursing Clinics* 5. pages 281-290. 2010. The use of ozone gas and hydrogen peroxide gas plasma for low temperature sterilization provides a quick cycling time without the dangers of toxic residuals. A recent study also demonstrated that in-flight bacteria inactivation may be achieved using ozone and nonthermal plasma, which is derived from a dielectric barrier grating discharge. See, Vaze, Nachiket D. et al. Inactivation of Bacteria in Flight by Direct Exposure to Nonthermal Plasma. *IEEE Transactions on Plasma Science*, Vol. 38, No. 11. November 2010.

Ozone is a naturally occurring elemental form of oxygen. It is formed naturally in the environment or artificially with an ozone generator. In the atmosphere, ozone is produced in nature by UV light from the sun or high-voltage electric discharges from lightening. Ozone can also be artificially induced by passing an electric field through a curtain of oxygen gas. See, Broder, Bryant C. and Jason Simon. Understanding Ozone. *Materials Management in Health Care*. September 2004. Ozone can also be produced by passing air or oxygen gas through UV light at approximately 185 nm wavelength, though to a significantly lower effect than with an electric field or corona discharge. The use of ozone sterilization technology was approved by the FDA in 2003. In its application for low-temperature sterilization, ozone is produced using medical-grade oxygen which is stimulated by electricity in a deep vacuum within a sterilization chamber. This reaction causes the ozone molecule to revert back to its diatomic state by releasing an extra oxygen atom which attaches to micro-organisms and oxidizes proteins and enzymes which result in the death of the organic matter. Since ozone can be converted back into oxygen and water vapor, which can be safely vented, this method provides a sound and economical sterilization process. One novel approach to sterilization technology employs ultrasonic cavitation augmented by injected ozone of high concentration. By varying the temperature of the water bath and the concentration of ozone subjected to a continuous or periodic ultrasound source, it is possible to increase the effectiveness of this application for reducing microbiological pollution. See, Krasnyj, V. V. et al. Sterilization of Microorganisms by Ozone and Ultrasound. *PLASMA* 2007, edited by H. J. Hartfuss et al. American Institute of Physics. 2008. Another original application of ozone in a sterilization process uses ultrasonic levitation energy and ozone bubbles to remove particles from soiled materials, which are then treated with silver electrolysis to kill microbes. Microorganisms have a bi-phospholipid layer which can only function properly in a specific conformation maintained by the disulfide bond —S—S—. Silver ions or atoms produced by silver electrolysis disrupt the bond between —S—S— and —SAg, interfering with the conformation, which then inhibit the respiration or nutrition of aerobic organisms, and thereby produce microbial inactivity. See, Ueda, Toyotoshi, et al. Simultaneous Treatment of Washing, Disinfection and Sterilization Using Ultrasonic Levitation, Silver Electrolysis and Ozone Oxidation. *Biocontrol Science*, Vol. 14, No. 1, pages 1-12. 2009. Ozonated water is created by either injecting ozone gas into water, or by exposing oxygenated water to UV light at approximately 185 nm wavelength. Ozone in water as dilute as 1 ug/ml is anti-microbial, and can be used to sterilize. Plasma-activated water (PAW) is a plasmachemical solution obtained by the activation of water with electric discharges such as cold atmospheric plasma (CAP). PAW has been shown to significantly reduce microbial populations and even overcome the antibiotic resistance of bacteria when used in combination with antibiotics.

Using chemical compounds produced by the immune system, such as superoxide and hypochlorous acid, can prove to be useful because of their effectiveness and known compatibility with biological processes. Superoxide is a compound that contains the highly reactive oxygen radical $O_2^-$ and is used for oxygen-dependent killing mechanisms of microorganisms in the immune system. Hypochlorous acid is an acid and an oxidizer that can be created by the immune system with the chemical formulation HClO. Hypochlorous acid and its sodium hypochlorite NaClO and calcium hypochlorite $Ca(ClO)_2$ variations are used as effective disinfectants.

Hydrogen peroxide gas plasma also offers a fast, nontoxic alternative to EtO sterilization. One commercial application vaporizes an aqueous solution of hydrogen peroxide in a deep vacuum chamber. Once the gaseous hydrogen peroxide is diffused throughout the load, the chamber pressure is reduced and this produces the low-temperature gas plasma. Radiation energy in the range of radio frequency (RF) wavelength is applied to the chamber using an RF amplifier, and this induces a plasma state which produces reactive species that inactivate microbes. Once the high-energy species stop reacting, they recombine to form harmless water vapor, oxygen, and other nontoxic byproducts. See, Slaybaugh, RaeAnn. Sterilization: Gas Plasma, Steam, and Washer-Decontamination. http://infectioncontroltoday.com. Virgo Publishing. Jun. 1, 2000.

Possibly the simplest sterilization technique is to remove all micro-organisms from a fluid. Various fluid filtration methods have been utilized with varying degrees of filtration. A High Efficiency Particulate Air (HEPA) filter is generally defined as being capable of removing 99.97% of all particulates greater than 0.3 microns. More sophisticated filters such as Ultra Low Penetration Air (ULPA) filters are capable of removing 99.999% of all particulates and microorganisms of the most penetrating particle size at a specified air velocity. Super ULPA filters are capable of removing 99.9999% of all particulates and microorganisms on the same basis as the ULPA filters. Multi-stage sterile gas filters designed for filtering compressed or pressurized gases are capable of filtering 99.999+% at 0.01 microns (Balston Filters, Haverhill, Mass.). The smallest know living bacteria have a size of approximately 200 nm (0.2 microns), where the smallest known virus has a size of approximately 12 nm (0.012 microns), so it is important to select an appropriately rated filter to adequately remove bacteria and viruses from the media.

An alternative method for removing micro-organisms from a fluid involves the use of negative air ionization. This approach uses an electrostatic space charge system (ESCS) to create negatively charged airborne particles which may be collected onto special grounded collector plates or screens. The ESCS was observed to reduce biofilms on stainless steel surfaces by transferring a strong negative electrostatic charge to bacterial cells on exposed areas. See, Arnold, J. and B. W. Mitchell. Use of Negative Air Ionization for Reducing Microbial Contamination on Stainless Steel Surfaces. *Journal of Applied Poultry Research*, Vol. 11, pages 179-186. Poultry Science Association. 2002. One disadvantage to using negative air ionization involves the accumulation of potentially infectious particles onto adjacent surfaces or grounded parts of the ionizer, creating a "black-wall effect" observed on the discolored walls of the ionizer chamber. This problem may be alleviated, however, using localized grounded collecting plates.

Another potential downside in using ionizers is their ability to produce static charge which may interfere with medical equipment, though this exposure is minimal beyond a distance of 1 meter from the ionizer. See, Escombe, A. Roderick et al. Upper-Room Ultraviolet Light and Negative Air Ionization to Prevent Tuberculosis Transmission. *PLoS Medicine* (Public Library of Science). Vol. 6, Issue 3, March 2009.

Attempts have been made and disclosed to reduce HAI's by applying many of the aforementioned sterilization techniques to sterile sites. For example U.S. Pat. No. 6,283,986 relates to the method of treating wounds with UV radiation. U.S. Patent Publication No. 2010/0234794 relates to a system and method for reducing surgical site infection by delivering air to the surgical site and incorporating antimicrobial agents and optionally UV or blue light.

U.S. Patent Publication No. 2008/0161749 relates to a portable infection control device that creates an environment around an open wound containing sterile gas.

U.S. Patent Publication No. 2010/0280436 relates to an apparatus and method for reducing contamination of surgical sites by providing a laminar flow of sterile gas across the surgical site in order to prevent ambient airborne particles from entering the site.

U.S. Patent Publication No. 2009/0054853 relates to a system that forms a sterile gas barrier to prevent airborne contaminant from reaching the site, and where light is emitted to activate a therapeutic agent in the gas.

U.S. Pat. No. 6,513,529 relates to the method for excluding infectious agents from the site of an incision by repelling the electrostatically charged infectious agents.

U.S. Patent Publication No. 1991/5037395 relates to a system used to heat a medical device to an elevated temperature where bacteria cannot survive.

U.S. Pat. No. 5,037,395 relates to a catheter for suppressing tunnel infection by raising the temperature.

U.S. Patent Publication No. 2009/0143718 relates to a plasma treatment probe, which applies non-thermal plasma to a patient's body to treat a region.

U.S. Patent Publication No. 2008/0017564 relates to an apparatus used to remove particulates from a flowing fluid using magnetic attraction and repulsion.

U.S. Patent Publication No. 2010/0268249 relates to a system used to create a sterile barrier while still permitting the use of medical instruments on the surgical site.

U.S. Patent Publication No. 2004/6733435 relates a system and method used to treat an infection and other conditions of a lesion with a magnetic field.

U.S. Pat. No. 5,154,165 relates a device and method used to reduce infection in a patient's body by generating an electric field.

U.S. Pat. No. 6,254,625 relates a device used to reduce infection by sanitizing hands.

U.S. Patent Application No. 2010/0222852 relates an apparatus and method used to reduce infection by decolonizing microbes on the surfaces of the skin and in body cavities.

U.S. Patent Application No. 2010/0266446 relates an apparatus used to reduce infection by sanitizing the hands and forearms.

U.S. Pat. No. 8,318,090 relates a system and method used to reduce infection by sanitizing the hands.

U.S. Pat. No. 6,254,625 relates an apparatus and method used to reduce infection by sanitizing the hands.

U.S. Pat. No. 8,142,713 relates a system and method used to reduce infection by sanitizing the hands.

Accordingly, each of the aforementioned inventions has limitations and there is still a need for novel apparatuses, systems, and methods for reducing healthcare acquired infections by preventing infectious agents at the sterile site.

SUMMARY OF THE INVENTION

This invention provides an apparatus configured to reduce infectious agents at a sterile site in order to reduce the incidence of a healthcare associated infections and disease. Therefore, an apparatus, system, and method are disclosed that utilize one or more of the aforementioned methods of preventing infectious agents from coming in contact with the sterile site while protecting the sterile site and the user from the potential negative effects of these methods.

In one aspect, the invention provides an apparatus for creating an infectious agent barrier for a sterile site. The apparatus has a housing that defines an opening for access of an object to the sterile site and at least one emitter of electromagnetic radiation coupled to the housing. The emitter is positioned to direct electromagnetic radiation into the opening defined by the housing and is configured to create a field of electromagnetic radiation across the opening that is substantially free of voids, so when an object passes through the opening, the outer perimeter of the object intersects the field. The apparatus can have at least three emitting points. The apparatus can have a housing that completely surrounds the sterile site with no interruptions. The apparatus of claim can have a housing that is configured as a surgical retractor. The housing can be configured to create the opening by holding the skin and tissue. The apparatus can have electromagnetic radiation that is ultra violet radiation with a wavelength between 200 and 280 nm. The electromagnetic radiation can be ultraviolet radiation that has a mean wavelength of 260 nm+/−10 nm. The electromagnetic radiation can be ultraviolet radiation that has a minimum energy level of 6000 microwatts per second per square centimeter. The ultra violet radiation can be produced by light emitting diodes. The apparatus can have electromagnetic radiation field that is coherent. The coherent electromagnetic radiation field can be defined as a plane. The apparatus can have electromagnetic radiation that is an electric field. The electromagnetic radiation can be an electric field that is alternating. The electromagnetic radiation can be an electric field that is high frequency. The electromagnetic radiation can be an electric field that has a frequency between 5 Mhz and 20 Mhz. The electromagnetic radiation can be an electric field that has a frequency of 10 Mhz+/−2 Mhz. The apparatus can have a housing that is shielded. The apparatus can have an electromagnetic radiation field that is activated by a sensor. The electromagnetic radiation can have a sensor that is activated when an object in proximity to the sterile site is sensed. The electromagnetic radiation can have a sensor that is activated based on a condition change at the sterile site. The electromagnetic radiation can have a sensor that is activated when an object intersects the opening in the sterile site. The apparatus can be configured where the opening is a lumen. The apparatus can be configured where the sterile site is a surgical site. The apparatus can be configured where the surgical site is a surgical incision. The apparatus can be configured where the surgical incision is for placement of a CIED. The apparatus can be configured where the sterile site is a sterile field. The apparatus can be configured where the sterile site is a hood. The apparatus can be configured where the sterile site is a wound. The apparatus can be configured where the sterile site is a catheter. The sterile site can be configured where the catheter is a central line, dialysis, PICC, port, foley, ventilator, pacing lead, or feeding tube. The apparatus can be configured where the sterile site is a luer. The sterile site can be configured where the luer is a swabbable luer. The apparatus can be configured where the sterile site is a fitting. The apparatus can be configured where the sterile site is a hub. The apparatus can be configured where the sterile site is a tubing line. The apparatus can be configured where the EMR is plasma. The apparatus can be configured where the EMR is an electron beam. The apparatus can be configured where the object includes one or more of an instrument, a device, and an appendage of a medical professional.

In another aspect the invention provides a sterile site in a living body that has an inner and outer diameter, and a longitudinal length. The invention also has an apparatus for creating an infectious agent barrier for a length of the sterile site, the apparatus has a housing with a width and has an opening partially surrounding the sterile site. The housing has at least one emitter of energy coupled to the housing, and the emitter is positioned to direct energy into the opening defined by the housing and is configured to create a field of energy around the sterile site that is substantially free of voids and has a length longer than its width, so that a portion of the inner and outer diameter and length of the sterile site intersects the field. The apparatus can be configured where the energy is in the form of heat. The energy can be configured where the heat is generated by an exothermic reaction. The apparatus can be configured where the energy is an electric field. The apparatus can be configured where the energy is a combination of heat and an electric field. The apparatus can be configured where the energy is electromagnetic radiation. The energy can be electromagnetic radiation that is ultraviolet light. The apparatus can be configured where the sterile site is a catheter. The sterile site can be a catheter that is a central line, dialysis, PICC, port, foley, ventilator, pacing lead, or feeding tube.

In yet another aspect, the invention provides an apparatus for creating an infectious agent barrier for a sterile site. The apparatus has a housing with an inner perimeter surface and an outer perimeter surface. The inner perimeter surface has an opening for access of an object to the sterile site. The outer perimeter surface creates a barrier for the sterile site. There is at least one emitter of energy coupled to the housing, and the emitter is positioned to direct energy into the barrier defined by the housing and is configured to create a field of energy around the barrier that is substantially free of voids, so that an infectious agent in proximity to the barrier intersects the field. The apparatus can be configured where the housing's inner perimeter surface is substantially convex. The apparatus can be configured where the housing's outer perimeter surface is substantially concave. The apparatus can be configured as a surgical wound retractor. The housing can be configured where the surgical wound retractor is malleable. The apparatus can be configured where the energy is in the form of heat. The energy can be heat that is generated by an exothermic reaction. The apparatus can be configured where the energy is an electric field. The apparatus can be configured where the energy is a combination of heat and an electric field. The apparatus can be configured where the energy is electromagnetic radiation. The apparatus can have a housing that contains a heat conductive material. The apparatus can have a housing that contains an antimicrobial coating. The apparatus can be configured where the energy is an electric charge. The energy can be an electric charge that is a positive charge. The energy can be an electric charge that is a negative charge. The apparatus can be configured where the energy is pressurized gas. The energy can be pressurized gas that is sterile air. The energy can be pressurized gas that is $CO_2$. The apparatus can be configured where the housing is elastic and configured to close the opening into the sterile site.

In still yet another aspect, the invention provides a system for creating an infectious agent barrier for a sterile site. The system has a luer activated port in fluid communication with a living body and has an internal surface and external luer thread. The system also includes a sterile site apparatus that has a housing configured to mate with the external luer thread of the luer activated port. The housing has at least one emitter of electromagnetic radiation and one sensor coupled to the housing, so that the sterile site apparatus can create a field of electromagnetic radiation that is substantially free of voids over the internal surface and external luer threads of the luer activated port when the sensor detects that the sterile site apparatus is mated to the luer activated port. The system can be configured where the electromagnetic radiation is ultra violet radiation with a wavelength between 200 and 280 nm. The electromagnetic radiation can be ultraviolet radiation that has a mean wavelength of 260 nm+/−10 nm. The electromagnetic radiation can be ultraviolet radiation that has a minimum energy level of 6000 microwatts per second per square centimeter. The ultra violet radiation can be produced by light emitting diodes.

A system is also provided for creating an infectious agent barrier for a sterile site, the system comprising a surgical retractor in contact with a living body having an internal and external surface; and a sterile site apparatus having a housing configured to mate with the internal surface of the surgical retractor, the housing having at least one emitter of energy coupled to the housing; whereby the sterile site apparatus creates a field of energy that is substantially free of voids over the internal and external surfaces of the surgical retractor. The system can be configured where the energy is in the form of heat. The energy can be heat that is generated by an exothermic reaction.

In still yet another aspect, the invention provides a system for creating an infectious agent barrier for a sterile site. The system has a surgical retractor in contact with a living body that has an internal and external surface. The system also includes a sterile site apparatus that has a housing configured to mate with the internal surface of the surgical retractor. The housing has at least one emitter of energy coupled to the housing so that the sterile site apparatus can create a field of energy that is substantially free of voids over the internal and external surfaces of the surgical retractor. The system can be configured where the energy is in the form of heat. The energy can be heat that is generated by an exothermic reaction.

In still yet another aspect, the invention provides a method of creating an infectious agent barrier for a sterile site. The method includes coupling at least one emitter from a list of 1) electromagnetic radiation, 2) electrical field, and 3) heat to a housing that has an opening for access of an object to the sterile site. The method also includes positioning said emitter to direct the electromagnetic radiation, electrical field, or heat into the opening defined by the housing. The method further includes configuring the emitter to create a field of electromagnetic radiation, electrical field, or heat across the opening that is substantially free of voids. The method further includes passing an object through the opening, so that the outer perimeter of the object intersects the field. The method can include where the electromagnetic radiation is ultra violet radiation with a wavelength between 200 and 280 nm. The electromagnetic radiation can be ultraviolet radiation that has a mean wavelength of 260 nm+/−10 nm. The electromagnetic radiation can be ultraviolet radiation that has a minimum energy level of 6000 microwatts per second per square centimeter. The ultra violet radiation can be produced by light emitting diodes. The method can include where the electric charge is a negative charge. The method can further include where the electric charge is a positive charge. The method can further include where the pressurized gas is sterile air. The method can further include where the pressurized gas is CO2. The method can further include where the heat is generated by an exothermic reaction. The method can further include where the housing is configured as a surgical retractor According to another aspect of this invention, an apparatus is provided for creating an electromagnetic radiation barrier for a sterile site, whereby infectious agents are inhibited from entering the sterile site. The apparatus includes a housing defining an unobstructed passage configured to receive an object, the passage having a proximal inlet and a distal outlet; at least one emitter of electromagnetic radiation coupled to the housing, the at least one emitter being positioned to direct electromagnetic radiation into the passage defined by the housing and being configured to create a substantially void free barrier of electromagnetic radiation extending across the passage; the barrier of electromagnetic radiation having a proximal extent, a distal extent, and a depth defined by the distance between the proximal extent and the distal extent, whereby an outer perimeter of the object does not intersect the barrier when the entire object is proximal to the proximal inlet of the passage or distal to the distal outlet of the passage and intersects the barrier when the object passes through the proximal inlet to the distal outlet; the barrier creating a substantially void free intersection of electromagnetic radiation with the object perimeter corresponding to the depth of the barrier as the object passes between the proximal inlet and distal outlet of the passage. According to still another aspect of the invention, a sterile site apparatus is provided for creating an electromagnetic radiation barrier, whereby infectious agents are inhibited from entering the sterile site. The apparatus includes a housing defining an unobstructed proximal opening configured to receive an object and an unobstructed distal opening configured to receive an object; at least one emitter of electromagnetic radiation coupled to the housing, the at least one emitter being positioned to direct electromagnetic radiation into a passage extending between the proximal and distal openings defined by the housing and being configured to create a substantially void free barrier of electromagnetic radiation extending across the passage; means for limiting proximal and distal extents of the barrier of electromagnetic radiation to remain within the passage between the proximal and distal openings defined by the housing whereby an outer perimeter of the object does not intersect the barrier when the entire object is proximal to the proximal opening or distal to the distal opening; and the barrier creating a substantially void free intersection of electromagnetic radiation with the object perimeter as the object passes through the passage between the proximal and distal openings defined by the housing of the sterile site apparatus. According to another aspect of the invention, a system is provided for inhibiting infectious agents on an object from entering a sterile site. The system includes a barrier generation means for generating a substantially void free barrier that inhibits the infectious agents from entering the sterile site by intersecting a perimeter of the object and remaining substantially void free upon the intersection of the barrier with the perimeter of the object; a sensor positioned to sense at least one of infectious agents, the object, ambient surroundings of the sterile site, and the barrier generated by the barrier generation means; and a control system coupled to the barrier generation means and to the sensor, the control system being configured to receive conditions sensed by the sensor and to activate the barrier generation means to generate the barrier.

A method for inhibiting infectious agents on an object from entering a sterile site is provided according to yet another aspect of the invention. The method includes positioning a barrier generation means for generating a substantially void free barrier such that the barrier inhibits the infectious agents from entering the sterile site by intersecting a perimeter of the object and remains substantially void free upon the intersection of the barrier with the perimeter of the object; sensing at least one of infectious agents, the object, ambient surroundings of the sterile site, and the barrier generated by the barrier generation means; and activating the barrier generation means to generate the barrier in response to conditions sensed by the sensor.

The disclosure and its various embodiments can now be better understood by turning to the following detailed description of the embodiments which are presented as illustrated examples of aspects of the invention. It is expressly understood that the claims are not limited by the illustrated embodiments described below.

BRIEF DESCRIPTION OF THE DRAWINGS

The apparatuses and their advantages will be understood more fully from the following description of the figures where:

FIG. 16 is a pictorial view illustration of the inflated vacuum tube with semi-rigid insertion card.

FIG. 17 is a side view illustration of the inflated vacuum tube with semi-rigid insertion card.

FIG. 18 is a rear view illustration of the inflated vacuum tube with semi-rigid insertion card.

FIG. 19 is a top view illustration of an embodiment of a sterile site apparatus positioned above the sterile site.

FIG. 20 is a cross-sectional view illustration of the sterile site apparatus of FIG. 19 while its gas release openings release gas mixtures to displace infectious agent containing air.

FIG. 113 is a top view illustration of an embodiment of a line source multiple partial-toroid plano-convex lens apparatus, which uses a line source EMR emitter and multiple partial-toroid plano-convex lens to create an EMR barrier.

FIG. 114 is a cross-sectional view illustration of the line source multiple partial-toroid plano-convex lens apparatus of FIG. 113.

FIG. 115 is a top view illustration of an embodiment of a point source multiple partial-toroid plano-convex lens apparatus, which uses point source EMR emitters and multiple partial-toroid plano-convex lens to create an EMR barrier.

FIG. 116 is a cross-sectional view illustration of the point source multiple partial-toroid plano-convex lens apparatus of FIG. 115.

FIG. 117 is a side view illustration of an embodiment of a sterile site apparatus.

FIG. 118 is a cross-sectional view illustration of the sterile site apparatus of FIG. 117 to show the distribution of fiber optics throughout the housing.

FIG. 119 is a side view illustration of an embodiment of a sterile site apparatus.

FIG. 120 is a cross-sectional view illustration of the sterile site apparatus of FIG. 119 to show the distribution of internal EMR emitters inside the housing.

FIG. 121 is a top view illustration of an embodiment of a sterile site apparatus.

FIG. 122 is a cross-sectional view illustration of the sterile site apparatus of FIG. 121.

FIG. 123 is an enlarged view illustration of the sterile site apparatus of FIG. 122 to show how the desired wavelengths of EMR can be transmitted through a medium and towards the sterile site by using reflective surfaces.

FIG. 124 is a pictorial view illustration of an embodiment of a sterile site apparatus highlighting its ability to be molded into a desired shape.

FIG. 125 is a top view illustration of the sterile site apparatus of FIG. 124 while it emits an EMR barrier composed of the desired wavelengths of EMR.

FIG. 126 is a pictorial view illustration of the sterile site apparatus and its internal features.

FIG. 127 is an enlarged view illustration of the sterile site apparatus of FIG. 126 highlighting its internal features.

FIG. 128 is a pictorial view illustration of an embodiment of a sterile site apparatus with housing links connected to each other to form a flexible linked structure for the housing.

FIG. 129 is a top view illustration of the sterile site apparatus of FIG. 128 with the addition of the EMR barrier being emitted.

FIG. 130 is a pictorial view illustration of an embodiment of a sterile site apparatus with a cooling unit and a single EMR emitter located up against the housing.

Figure 131:
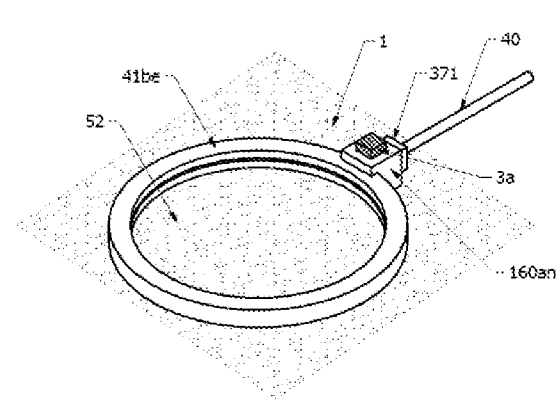

FIG. 131 is a pictorial view illustration of an embodiment of a sterile site apparatus with a cooling unit, an object sensor and a single EMR emitter located up against the housing.

Figure 132:
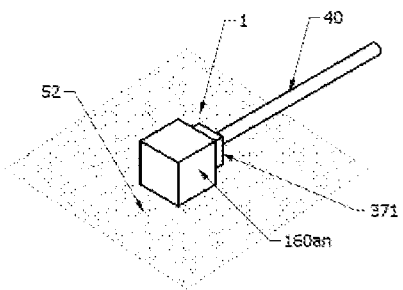

FIG. 132 is a pictorial view illustration of an embodiment of a sterile site apparatus with a cooling unit and a single EMR emitter, but without the housing.

Figure 133:
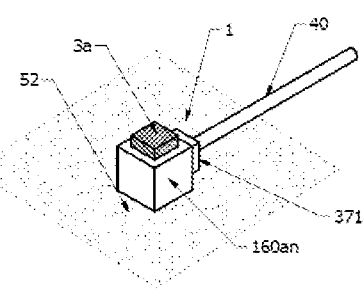

FIG. 133 is a pictorial view illustration of an embodiment of a sterile site apparatus with a cooling unit, and object sensor and a single EMR emitter, but without the housing.

Figure 134:
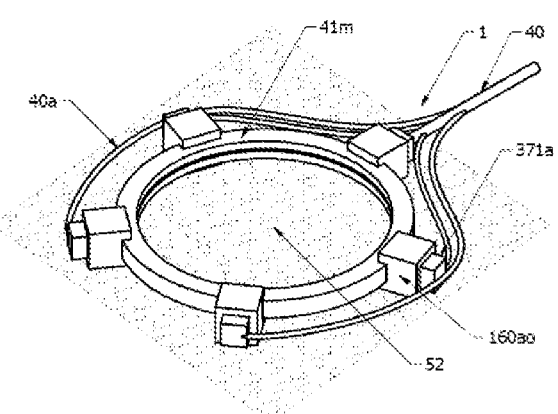

FIG. 134 is a pictorial view illustration of an embodiment of a sterile site apparatus with multiple cooling units and EMR emitters located up against the housing.

Figure 135:
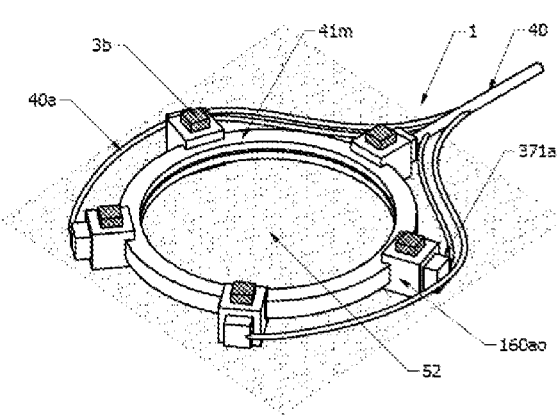

FIG. 135 is a pictorial view illustration of an embodiment of a sterile site apparatus with multiple cooling units, object sensors and EMR emitters located up against the housing.

Figure 136:
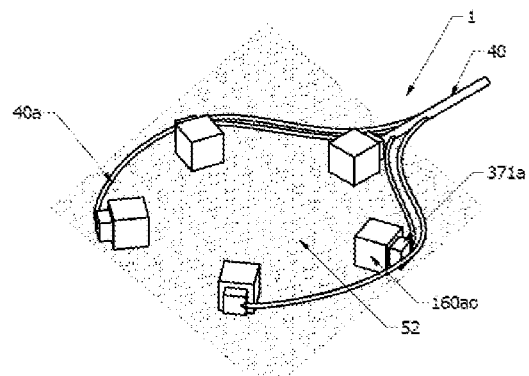

FIG. 136 is a pictorial view illustration of an embodiment of a sterile site apparatus with multiple cooling units and EMR emitters, but without the housing.

Figure 137:
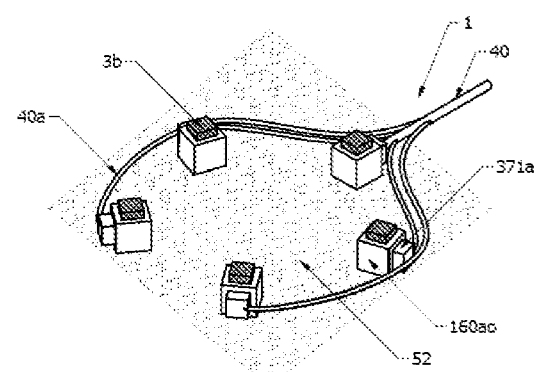

FIG. 137 is a pictorial view illustration of an embodiment of a sterile site apparatus with multiple cooling units, object sensors, and EMR emitters, but without the housing.

Figure 138:
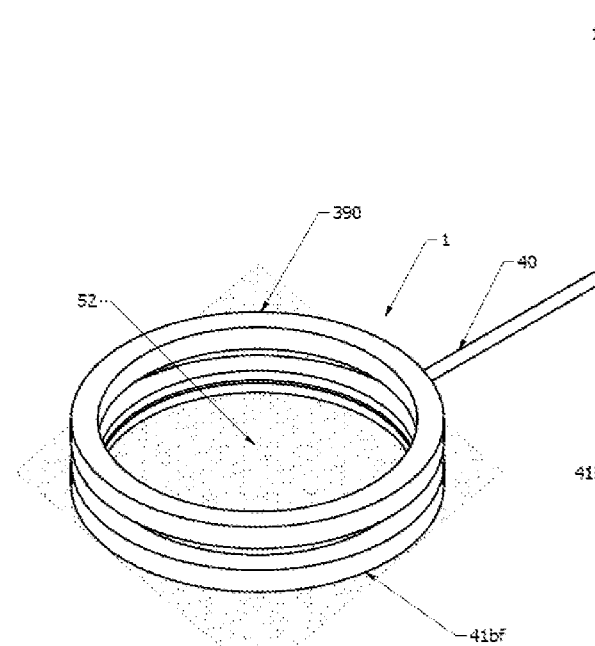

FIG. 138 is a pictorial view illustration of an embodiment of a sterile site apparatus with a positively charged electrode to attract negatively charged infectious agents.

Figure 139:
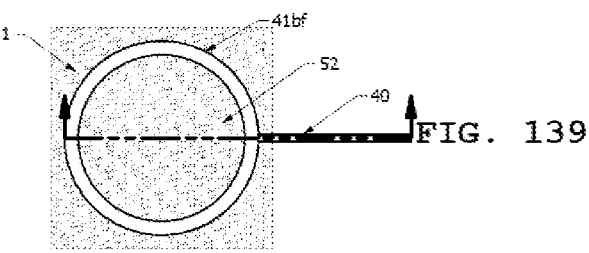

FIG. 139 is a top view illustration of the sterile site apparatus of FIG. 138.

Figure 140:
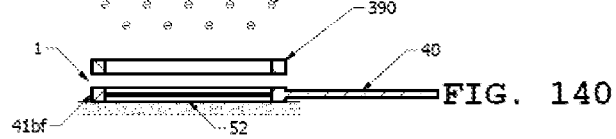

FIG. 140 is a cross-sectional view illustration of the sterile site apparatus of FIG. 139 with the addition of electrons and falling infectious agents.

Figure 141:
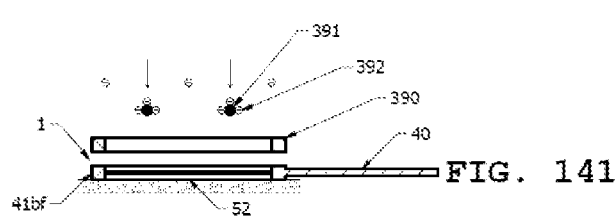

FIG. 141 is a cross-sectional view illustration of the sterile site apparatus of FIG. 139 once the infectious agents have become attached to the electrons.

Figure 142:
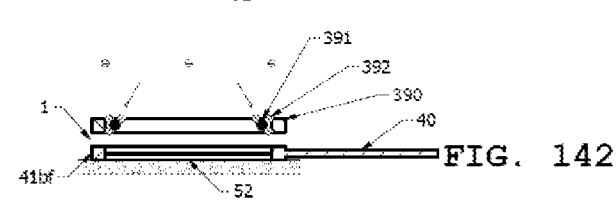

FIG. 142 is a cross-sectional view illustration of the sterile site apparatus of FIG. 139 once the negatively charged infectious agents have become attached to the positively charged electrode.

FIG. 143 is a pictorial view illustration of an embodiment of a sterile site apparatus with a negatively charged electrode to attract positively charged infectious agents.

FIG. 144 is a top view illustration of the sterile site apparatus of FIG. 143.

FIG. 145 is a cross-sectional view illustration of the sterile site apparatus of FIG. 144 with the addition of protons and falling infectious agents.

FIG. 146 is a cross-sectional view illustration of the sterile site apparatus of FIG. 144 once the infectious agents have become attached to the protons.

FIG. 147 is a cross-sectional view illustration of the sterile site apparatus of FIG. 144 once the positively charged infectious agents have become attached to the negatively charged electrode.

FIG. 148 is a pictorial view illustration of an embodiment of a sterile site apparatus with a negatively charged electrode to repel negatively charged infectious agents.

FIG. 149 is a top view illustration of the sterile site apparatus of FIG. 148.

FIG. 150 is a cross-sectional view illustration of the sterile site apparatus of FIG. 149 with the addition of electrons and falling infectious agents.

FIG. 151 is a cross-sectional view illustration of the sterile site apparatus of FIG. 149 once the infectious agents have become attached to the electrons.

FIG. 152 is a cross-sectional view illustration of the sterile site apparatus of FIG. 149 once the negatively charged infectious agents have been repelled by the negatively charged electrode.

FIG. 153 is a pictorial view illustration of an embodiment of a sterile site apparatus with a positively charged electrode to repel positively charged infectious agents.

FIG. 154 is a top view illustration of the sterile site apparatus of FIG. 153.

FIG. 155 is a cross-sectional view illustration of the sterile site apparatus of FIG. 154 with the addition of protons and falling infectious agents.

FIG. 156 is a cross-sectional view illustration of the sterile site apparatus of FIG. 154 once the infectious agents have become attached to the protons.

FIG. 157 is a cross-sectional view illustration of the sterile site apparatus of FIG. 154 once the positively charged infectious agents have been repelled by the positively charged electrode.

FIG. 158 is a top view illustration of an embodiment of a sterile site apparatus positioned over the sterile site.

FIG. 159 is a cross-sectional view illustration of the sterile site apparatus of FIG. 158 with the addition of ozone-generating EMR being emitted into the sterile site to create ozone gas, which is reverted back to oxygen gas as it leaves the sterile site due to contact with the EMR barrier.

Figure 160:
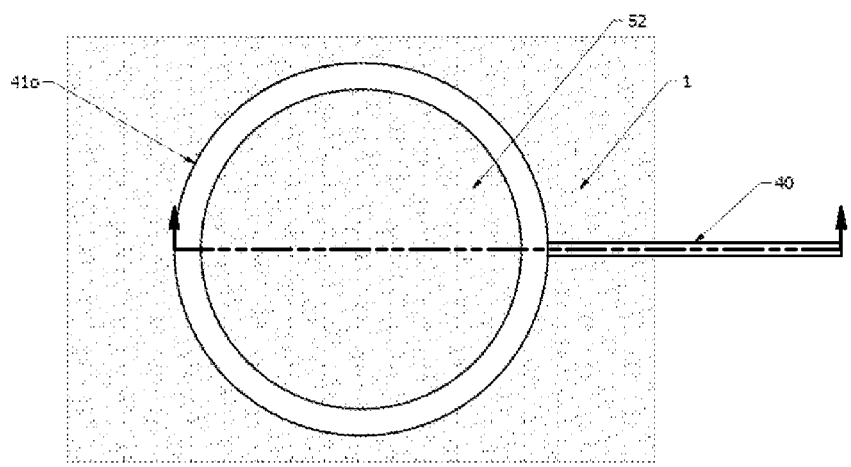

FIG. 160 is a top view illustration of an embodiment of a sterile site apparatus positioned over the sterile site.

Figure 161:
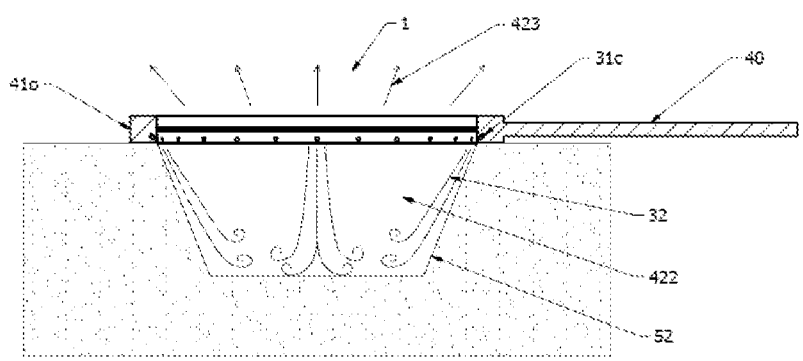

FIG. 161 is a cross-sectional view illustration of the sterile site apparatus of FIG. 160 with the addition of sterile gas being pumped into the sterile site to create a positive pressure region.

FIG. 162 is a top view illustration of an embodiment of a sterile site apparatus positioned over the sterile site.

FIG. 163 is a cross-sectional view illustration of the sterile site apparatus of FIG. 162 with the addition of ozone gas being pumped into the sterile site, where the ozone gas is reverted back to oxygen gas as it leaves the sterile site due to contact with the EMR barrier.

FIG. 164 is a top view illustration of an embodiment of a sterile site apparatus positioned over the sterile site.

FIG. 165 is a cross-sectional view illustration of the sterile site apparatus of FIG. 164 with the addition of fluids being pumped into or near the sterile site to form a disinfecting fluid barrier, a cloud over the sterile site apparatus and sterile site, or a cloud between the sterile site apparatus and sterile site.

FIG. 166 is a top view illustration of an embodiment of a sterile site apparatus positioned over the sterile site.

FIG. 167 is a cross-sectional view illustration of the sterile site apparatus of FIG. 166 with the addition of ozone-generating EMR being pulsed in the sterile site.

FIG. 168 is a cross-sectional view illustration of the sterile site apparatus of FIG. 166 with the addition of ozone gas that was created by ozone-generating EMR of FIG. 167.

FIG. 169 is a cross-sectional view illustration of the sterile site apparatus of FIG. 166 with the addition of ozone-eliminating EMR being pulsed in the ozone-filled region of the sterile site.

FIG. 170 is a cross-sectional view illustration of the sterile site apparatus of FIG. 166 with the sterile site containing only sterilized ambient gases.

FIG. 171 is a pictorial view illustration of an embodiment of a sterile site apparatus, its unbroken detecting region of the object sensor, and an object.

FIG. 172 is a pictorial view illustration of the sterile site apparatus of FIG. 171 after an object has disrupted the detecting region.

FIG. 173 is a top view illustration of an embodiment of a sterile site apparatus positioned over the sterile site.

FIG. 174 is a cross-sectional view illustration of the sterile site apparatus of FIG. 173 highlighting the various object and sterile site sensors.

FIG. 175 is a pictorial view illustration of an embodiment of a visible light detection system when no visible light is blocked from entering the transmission structure.

FIG. 176 is a pictorial view illustration of the visible light detection system when some visible light is blocked from entering the transmission structure by an object creating a shadow as the object travels near the sterile site.

FIG. 177 is a pictorial view illustration of the visible light detection and EMR emission system when no visible light is blocked from entering the transmission structure.

FIG. 178 is a pictorial view illustration of the visible light detection and EMR emission system when some visible light is blocked from entering the transmission structure by an object creating a shadow as the object travels near the sterile site, which causes the creation of an EMR barrier.

FIG. 179 is a pictorial view illustration of an embodiment of a sterile site apparatus highlighting its internal features.

FIG. 180 is an enlarged view of the sterile site apparatus of FIG. 179 highlighting its internal features.

FIG. 181 is a top view illustration of an embodiment of a sterile site apparatus positioned over the sterile site.

FIG. 182 is a cross-sectional view illustration of the sterile site apparatus of FIG. 181 displaying the location of the region of negative pressure and suction gasket used for attachment near the sterile site.

FIG. 183 is an enlarged view illustration of the sterile site apparatus of FIG. 182 highlighting the region of negative pressure and suction gasket.

Figure 184:
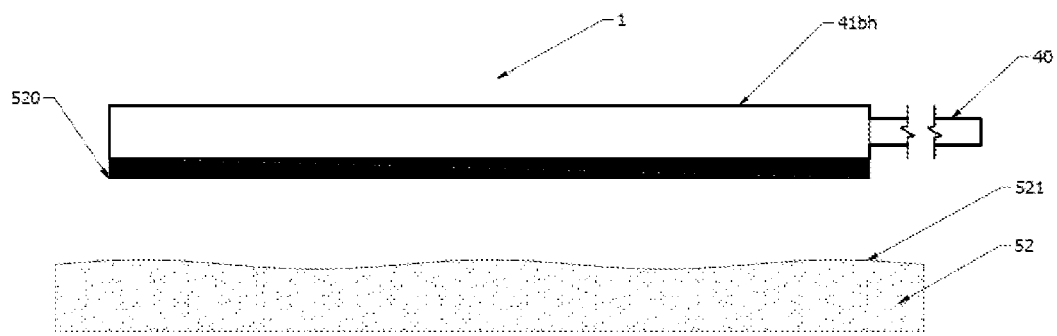

FIG. 184 is a side view illustration of an embodiment of a sterile site apparatus with a conformable gasket before it is placed near the sterile site.

Figure 185:
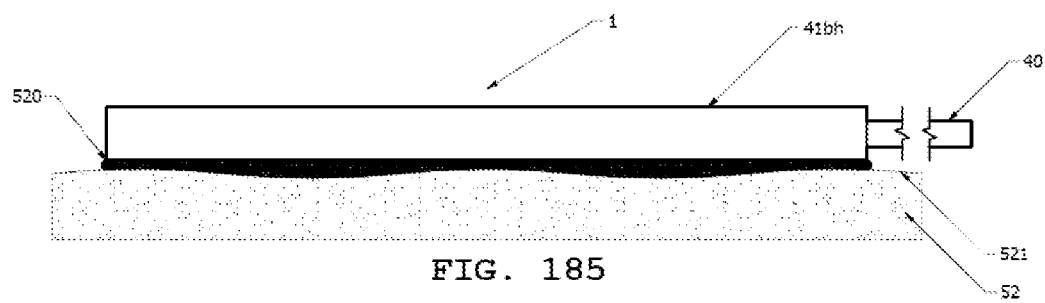

FIG. 185 is a side view illustration of the sterile site apparatus of FIG. 184 after the sterile site apparatus has been lowered and the conformable gasket has created a seal between the sterile site apparatus and area near the sterile site.

Figure 186:
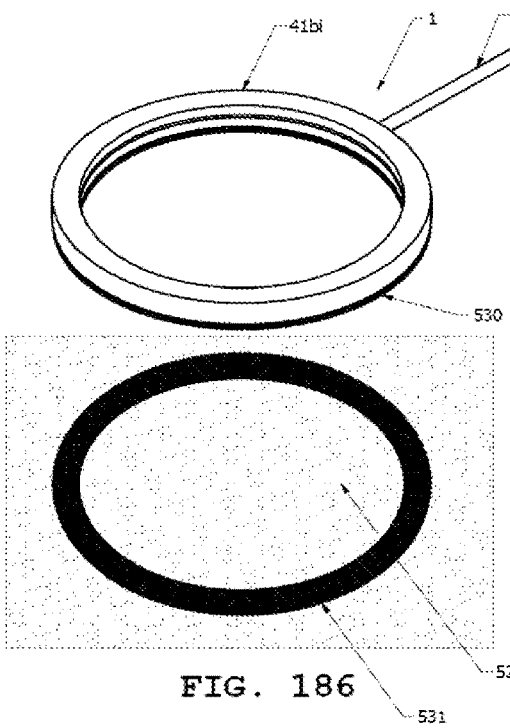

FIG. 186 is a pictorial view illustration of an embodiment of a sterile site apparatus and its magnetic strip before being lowered on the oppositely charged magnetic strip surrounding the sterile site.

Figure 187:
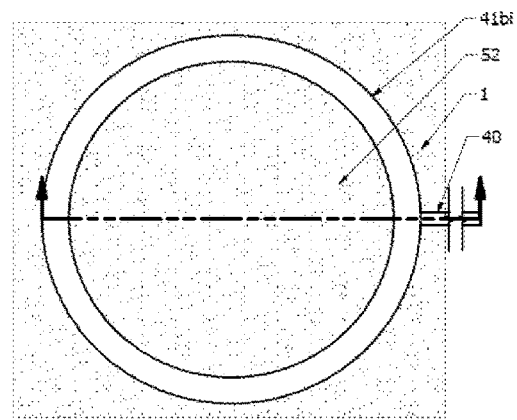

FIG. 187 is a top view illustration of the sterile site apparatus of FIG. 186.

Figure 188:
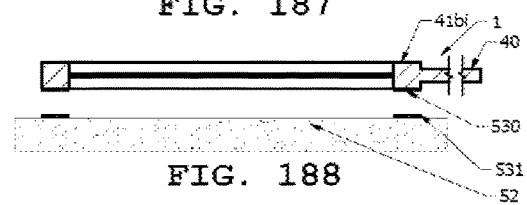

FIG. 188 is a cross-sectional view illustration of the sterile site apparatus of FIG. 187.

Figure 189:
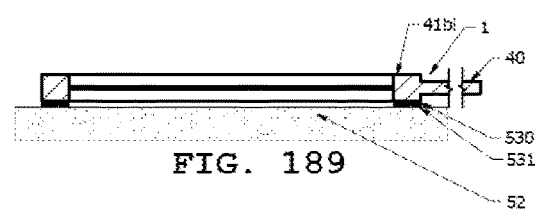

FIG. 189 is a cross-sectional view illustration of the sterile site apparatus of FIG. 187 after it has been lowered and the magnetic strips have engaged.

Figure 190:
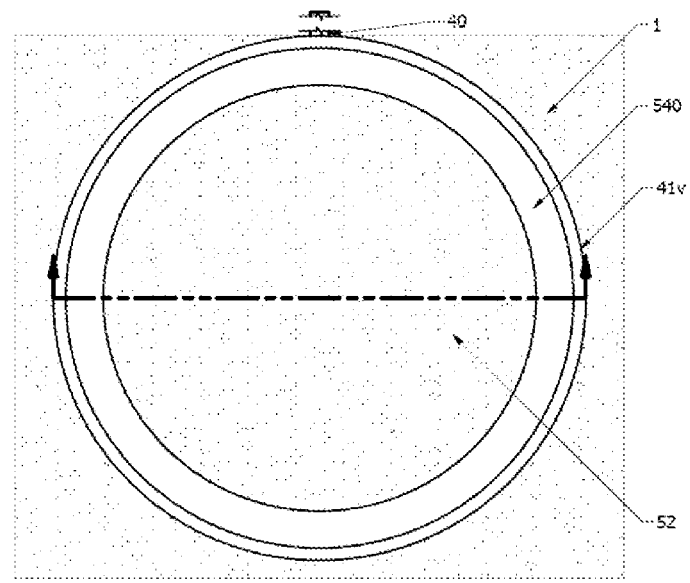

FIG. 190 is a top view illustration of an embodiment of a sterile site apparatus and its shield.

Figure 191:
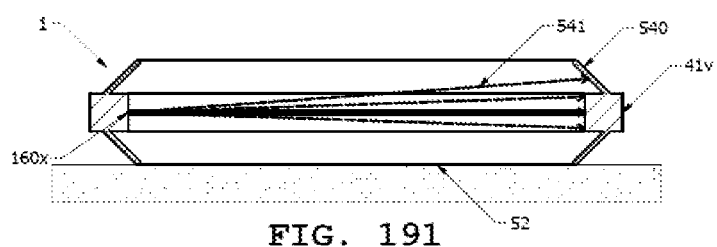

FIG. 191 is a cross-sectional view illustration of the sterile site apparatus of FIG. 190 and highlights the ability of the shield to protect against EMR released at a potentially harmful trajectory.

Figure 192:
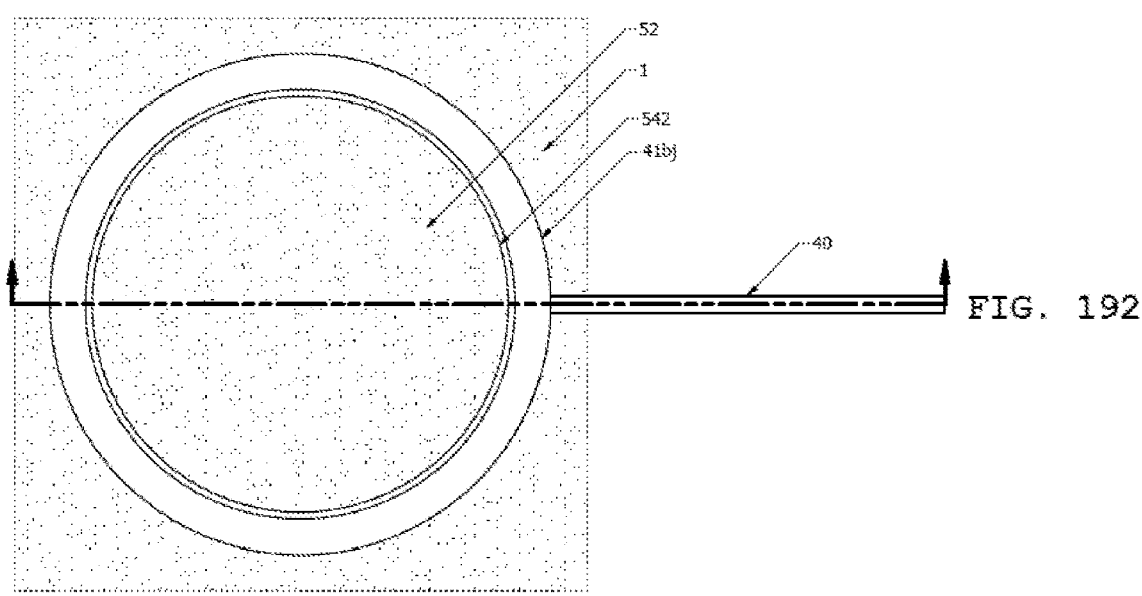

FIG. 192 is a top view illustration of an embodiment of a sterile site apparatus positioned over the sterile site.

Figure 193:
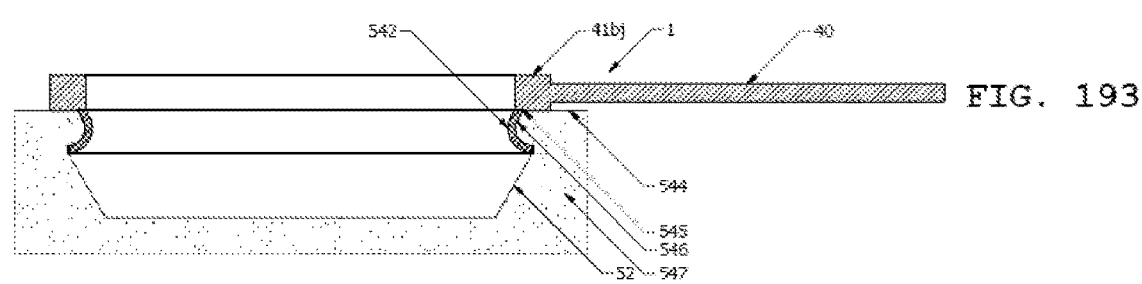

FIG. 193 is a cross-sectional view illustration of the sterile site apparatus of FIG. 192 highlighting the ability of the retracting feature to hold back human tissue and isolate infectious agents on the exterior surface of human tissue.

Figure 194:
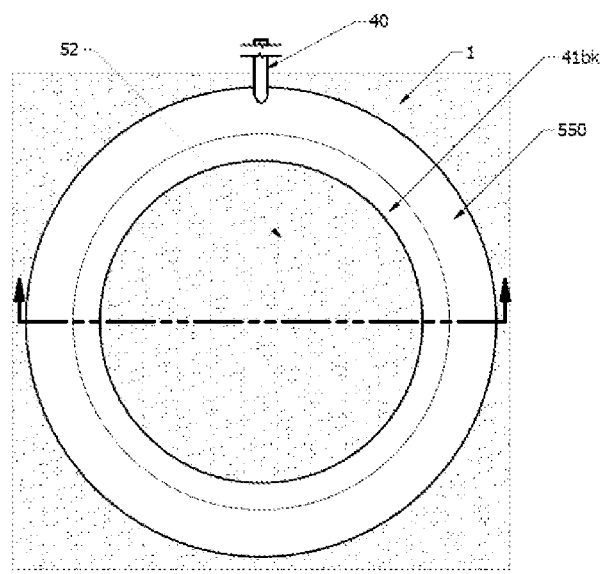

FIG. 194 is a top view illustration of an embodiment of a sterile site apparatus and its ergonomic attachment.

Figure 195:
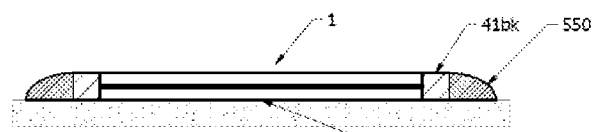

FIG. 195 is a cross-sectional view illustration of the sterile site apparatus and its ergonomic attachment of FIG. 194.

Figure 196:
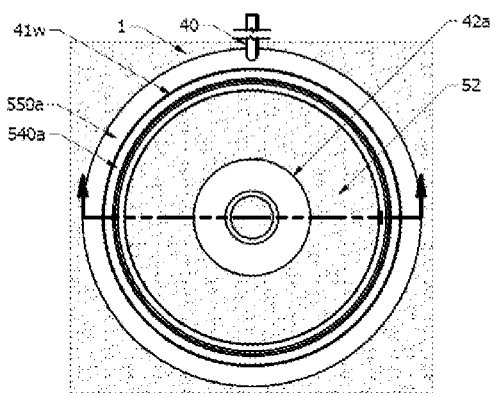

FIG. 196 is a top view illustration of an embodiment of a sterile site apparatus highlighting its various features.

Figure 197:
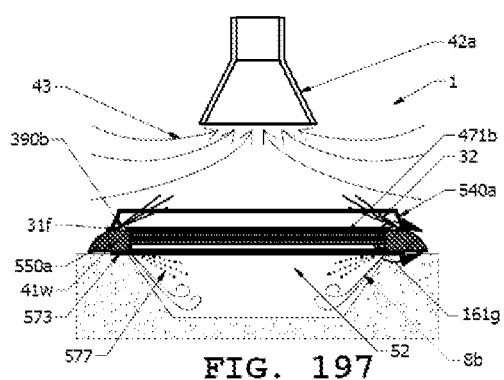

FIG. 197 is a cross-sectional view illustration of the sterile site apparatus of FIG. 196 highlighting its various features.

Figure 198:
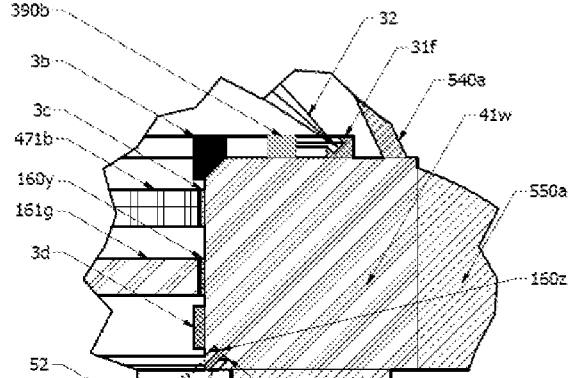

FIG. 198 is an enlarged view illustration of the sterile site apparatus of FIG. 197 highlighting its various features.

Figure 199:
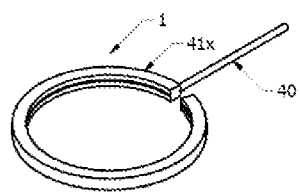

FIG. 199 is a pictorial view illustration of an embodiment of a sterile site apparatus before a sterile sleeve is slid onto the sterile site apparatus.

Figure 200:
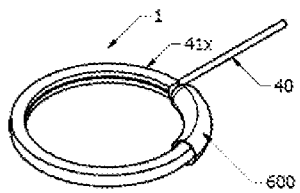

FIG. 200 is a pictorial view illustration of the sterile site apparatus of FIG. 199 with the addition of the sterile sleeve initially being slid onto the housing of the sterile site apparatus.

Figure 201:
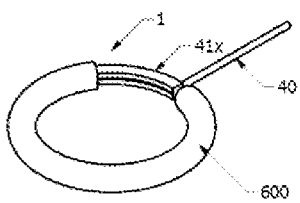

FIG. 201 is a pictorial view illustration of the sterile site apparatus of FIG. 200 with the sterile sleeve continuing to be slid onto the housing of the sterile site apparatus.

Figure 202:
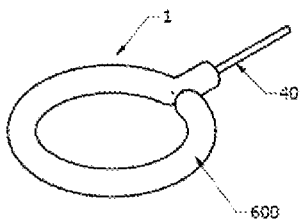

FIG. 202 is a pictorial view illustration of the sterile site apparatus of FIG. 201 with the sterile sleeve continuing to be slid onto the supply cord of the sterile site apparatus.

Figure 203:
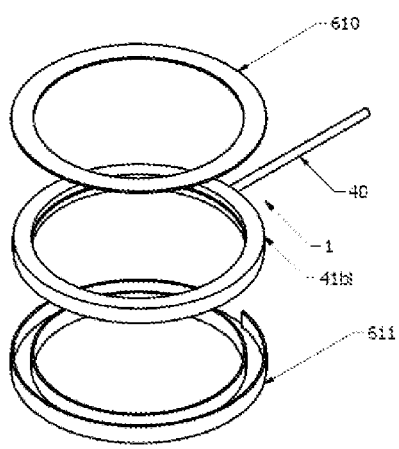

FIG. 203 is a pictorial view illustration of an embodiment of a sterile site apparatus before it is enclosed in the two sterile, rigid components.

Figure 204:
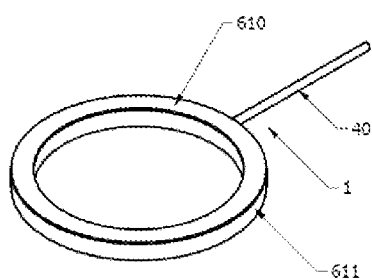

FIG. 204 is a pictorial view illustration of the sterile site apparatus of FIG. 203 after it is enclosed in the two sterile, rigid components.

Figure 205:
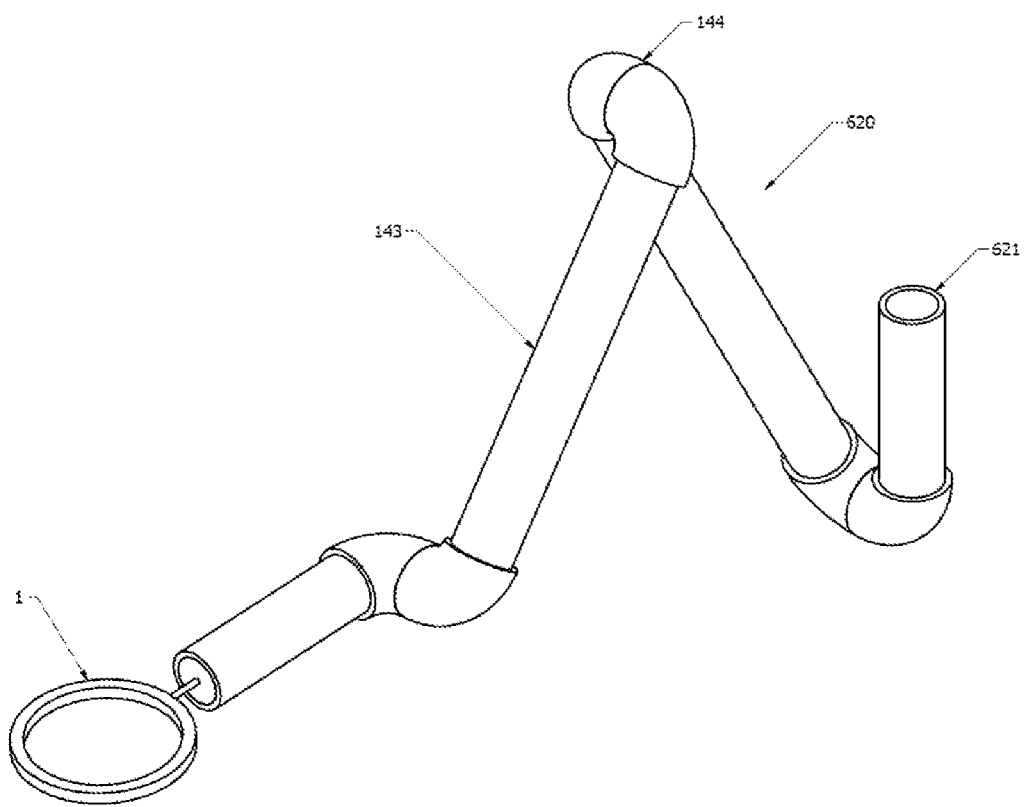

FIG. 205 is a pictorial view illustration of an embodiment of a movable arm with hollow, rigid members attached to movable joints, which allow for the desired positioning of the sterile site apparatus above the sterile site.

Figure 206:
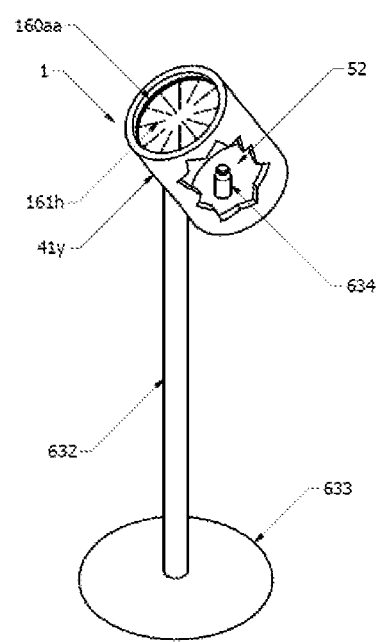

FIG. 206 is a pictorial view illustration of an embodiment of a sterile site apparatus used to disinfect an object before it can come in contact with a sterile site or to maintain the sterility of an object once it has entered an enclosure.

Figure 207:
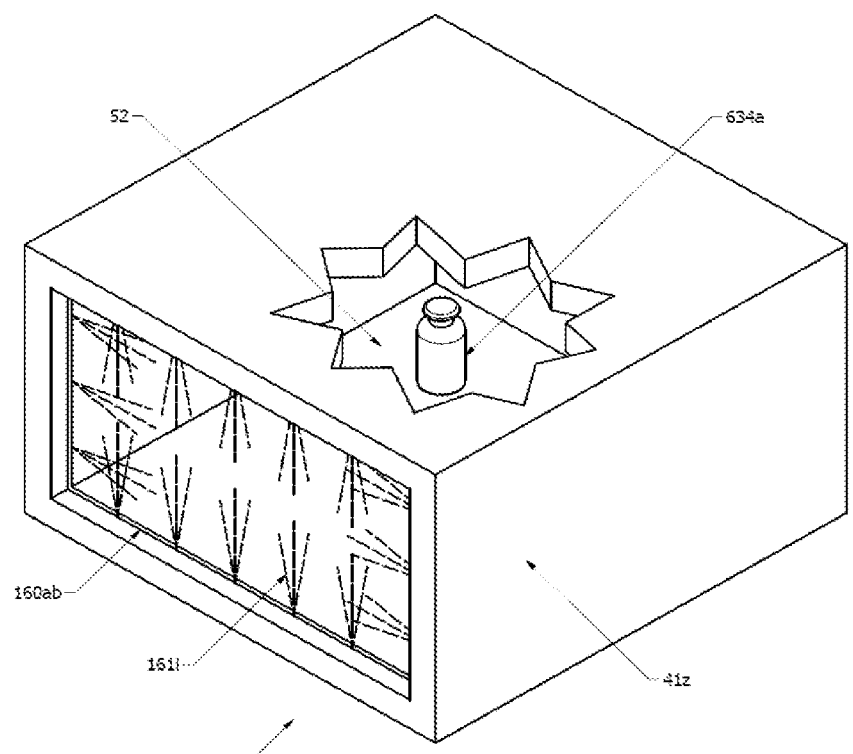

FIG. 207 is a pictorial view illustration of an embodiment of a sterile site apparatus used to disinfect an object before it can come in contact with a sterile site or to maintain the sterility of an object once it has entered an enclosure.

Figure 208:
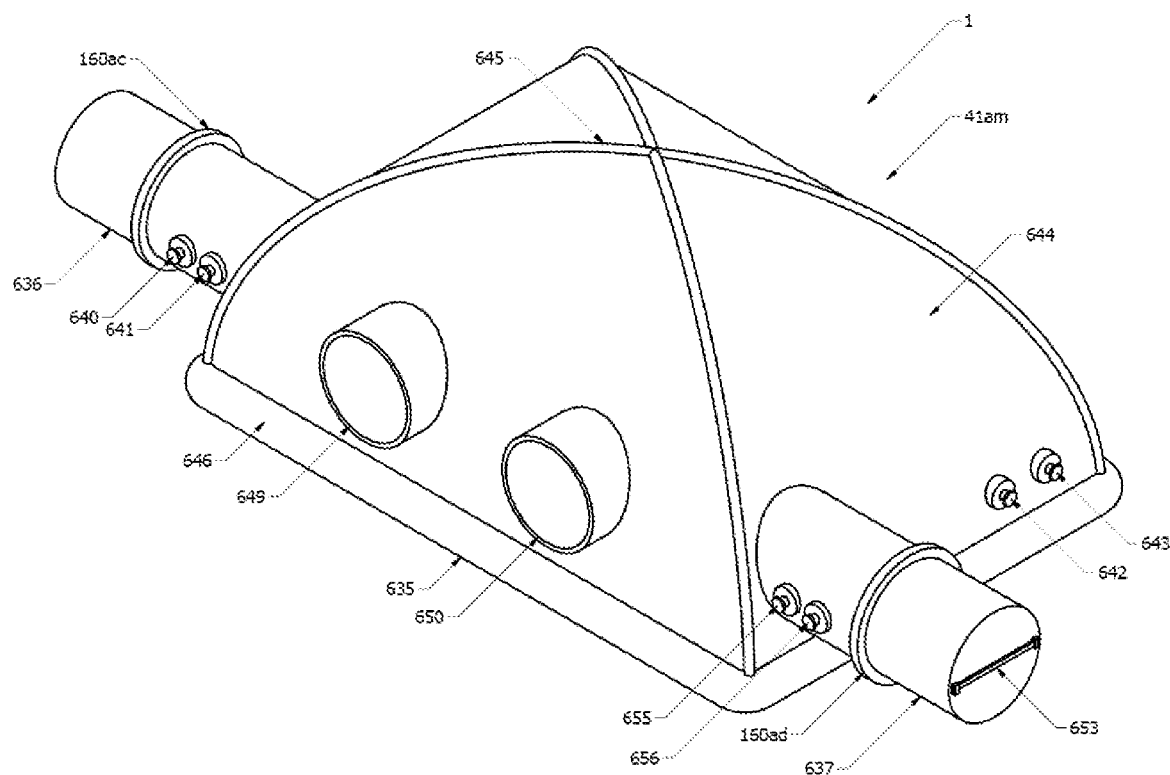

FIG. 208 is a pictorial view illustration of an embodiment of a sterile site apparatus and its associated enclosures, which isolate an object from the user and infectious agents in the ambient surroundings.

Figure 209:
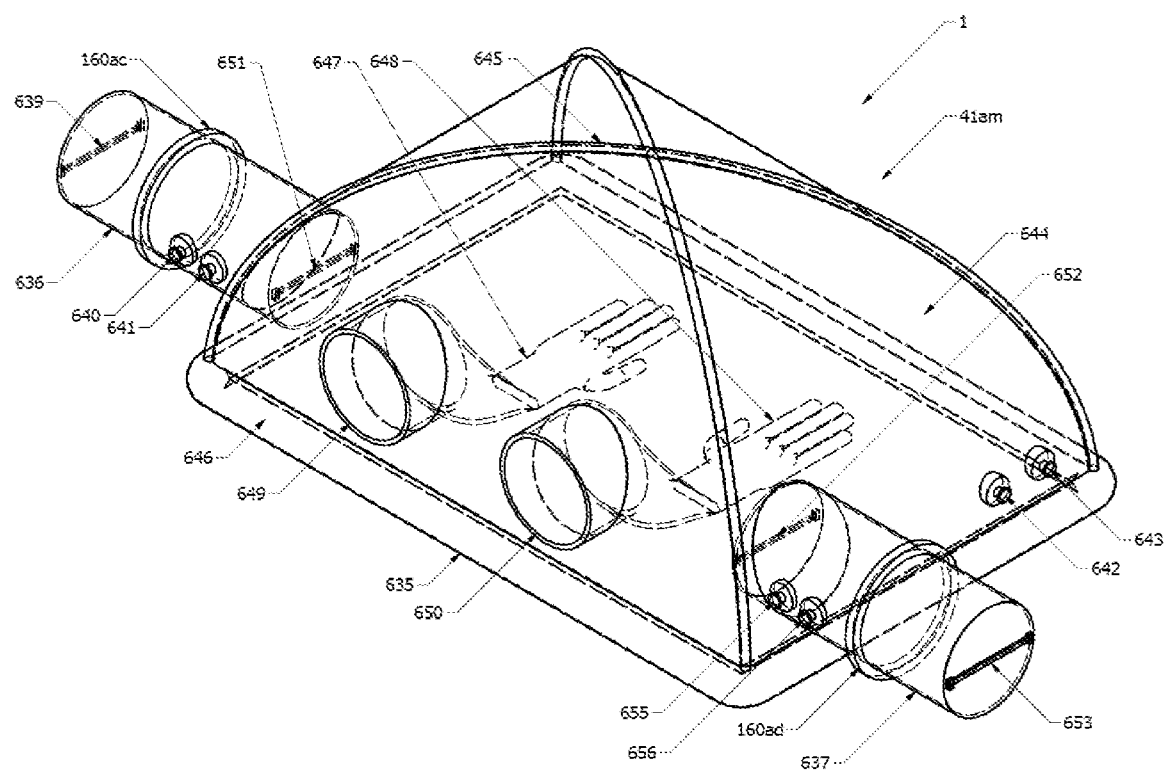

FIG. 209 is a pictorial view illustration with hidden lines of the sterile site apparatus and its associated enclosures, which isolate an object from the user and infectious agents in the ambient surroundings.

Figure 210:
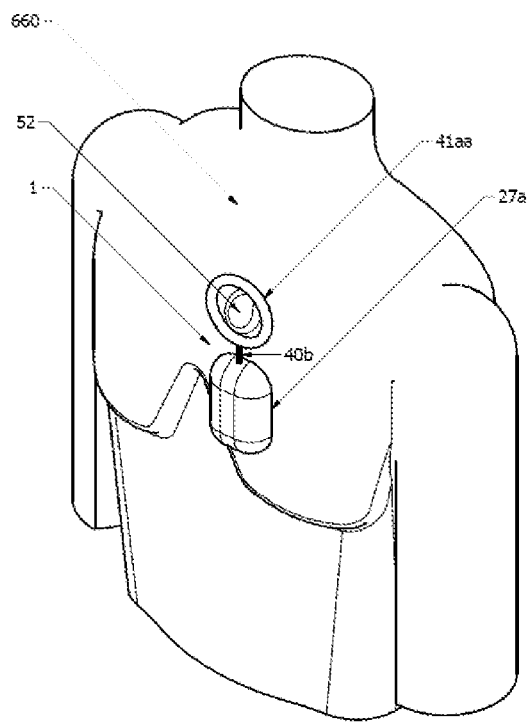

FIG. 210 is a pictorial view illustration of an embodiment of a sterile site apparatus attached to a patient and use during day-to-day activities to monitor conditions of the sterile site.

FIG. 211 is a side view illustration of an embodiment of a sterile site apparatus attached to an intravenous device to disinfect the intravenous device or objects that will administer fluids or drugs into the intravenous line.

FIG. 212 is a front view illustration of the sterile site apparatus and intravenous device of FIG. 211.

FIG. 213 is a cross-sectional view illustration of the sterile site apparatus and intravenous device of FIG. 212 highlighting the internal features of the sterile site apparatus.

FIG. 214 is a pictorial view illustration of an embodiment of a sterile site apparatus before it is engaged with an intravenous access device.

FIG. 215 is a top view illustration of the sterile site apparatus before it is engaged with an intravenous access device.

FIG. 216 is a cross-sectional view illustration of the sterile site apparatus and intravenous access device of FIG. 215.

FIG. 217 is an enlarged view illustration of the sterile site apparatus of FIG. 216.

Figure 218:
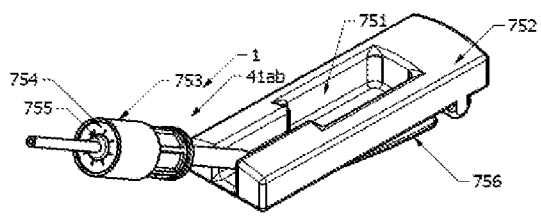

FIG. 218 is a pictorial view illustration of the sterile site apparatus after it is engaged with an intravenous access device.

Figure 219:
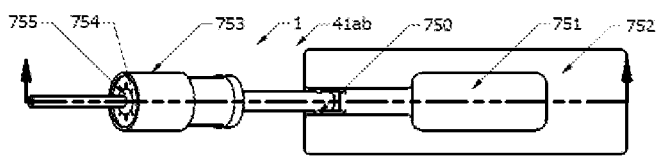

FIG. 219 is a top view illustration of the sterile site apparatus after it is engaged with an intravenous access device.

Figure 220:
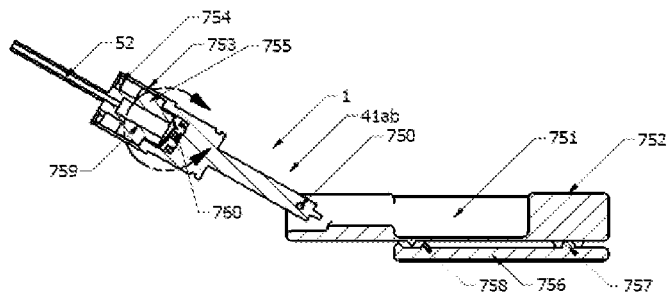

FIG. 220 is a cross-sectional view illustration of the sterile site apparatus and intravenous access device of FIG. 219.

Figure 221:
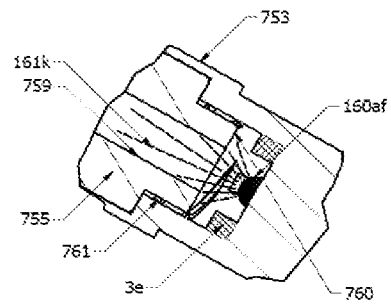

FIG. 221 is an enlarged view illustration of the sterile site apparatus of FIG. 220 highlighting the use of an EMR barrier to disinfect regions of the intravenous access device.

Figure 222:
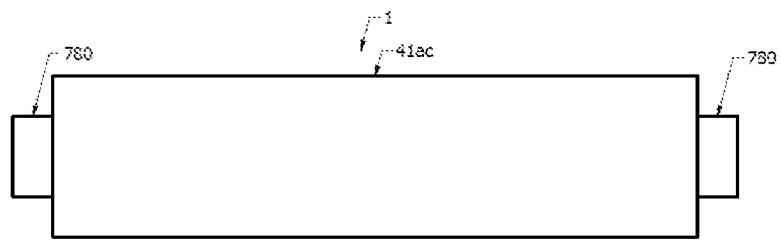

FIG. 222 is a front view illustration of an embodiment of a sterile site apparatus before it couples two tubular medical devices.

Figure 223:
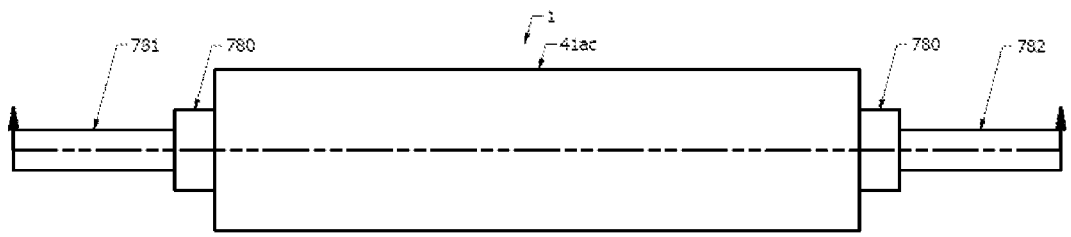

FIG. 223 is a top view illustration of the sterile site apparatus after it couples two tubular medical devices.

Figure 224:
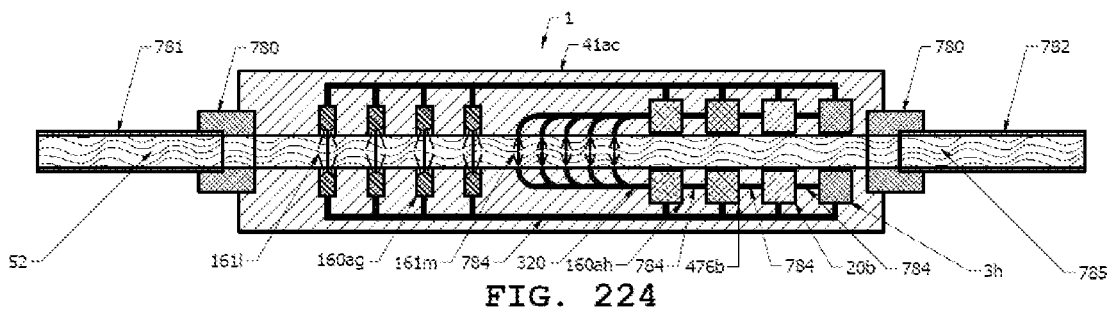

FIG. 224 is a cross-sectional view illustration of the sterile site apparatus of FIG. 223 highlighting its internal features.

Figure 225:
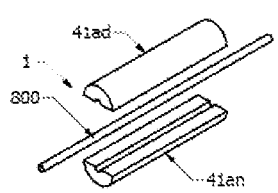

FIG. 225 is a pictorial view illustration of an embodiment of a sterile site apparatus before two pieces of the housing are assembled over a tubular medical device.

Figure 226:
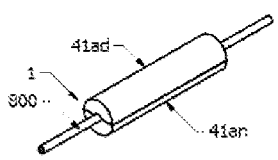

FIG. 226 is a pictorial view illustration of the sterile site apparatus after two pieces of the housing are assembled over a tubular medical device.

Figure 227:
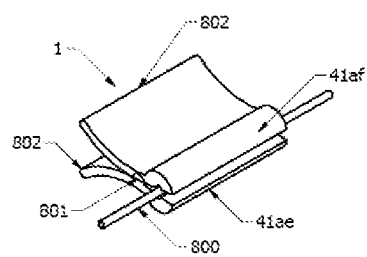

FIG. 227 is a pictorial view illustration of an embodiment of a sterile site apparatus before two pieces of the housing are clamped over a tubular medical device.

Figure 228:
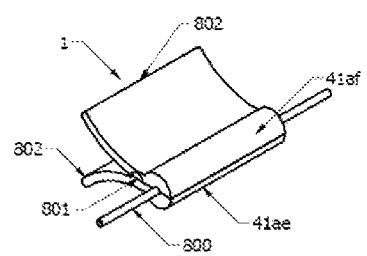

FIG. 228 is a pictorial view illustration of the sterile site apparatus after two pieces of the housing are clamped over a tubular medical device.

Figure 229:
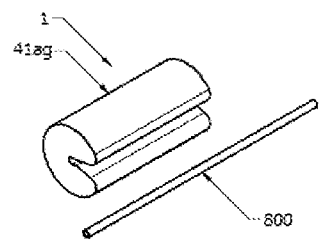

FIG. 229 is a pictorial view illustration of an embodiment of a sterile site apparatus before the housing is securely attached to a tubular medical device.

Figure 230:
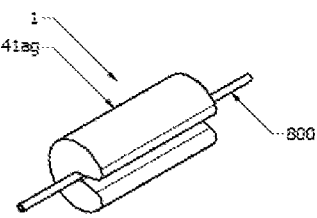

FIG. 230 is a pictorial view illustration of the sterile site apparatus after the housing is securely attached to a tubular medical device.

Figure 231:
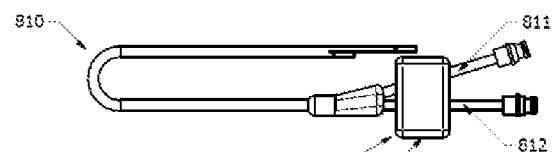

FIG. 231 is a top view illustration of an embodiment of a sterile site apparatus attached to two tubular medical device lines of the same multi-line tubular medical device.

Figure 232:
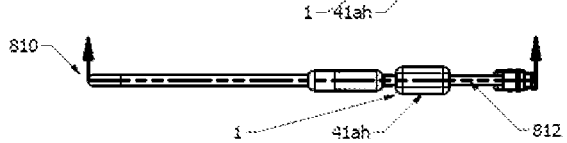

FIG. 232 is a front view illustration of the sterile site apparatus of FIG. 231.

Figure 233:
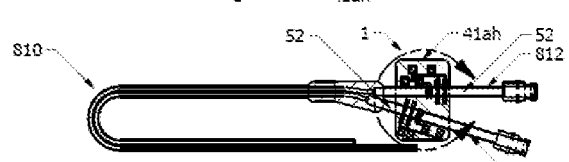

FIG. 233 is a cross-sectional view illustration of the sterile site apparatus of FIG. 232.

Figure 234:
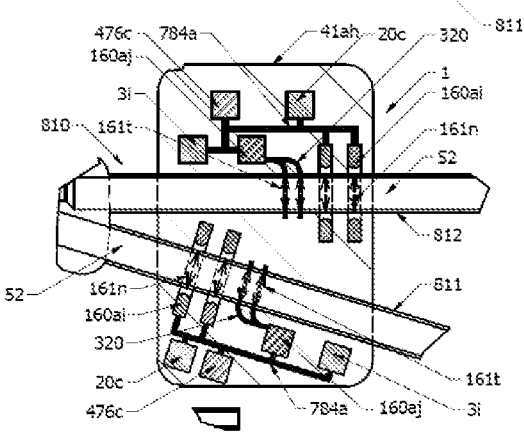

FIG. 234 is an enlarged view illustration of the sterile site apparatus of FIG. 233 highlighting its internal features.

Figure 235:
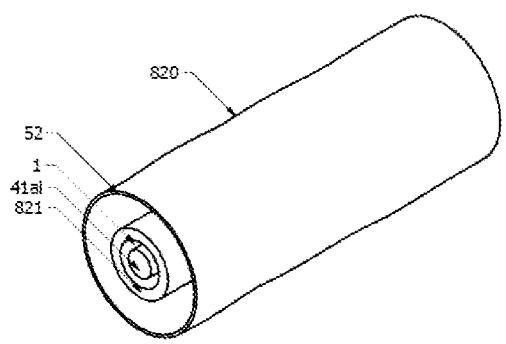

FIG. 235 is a pictorial view illustration of an embodiment of a sterile site apparatus and tubular medical device within the internal pathway of a patient.

Figure 236:
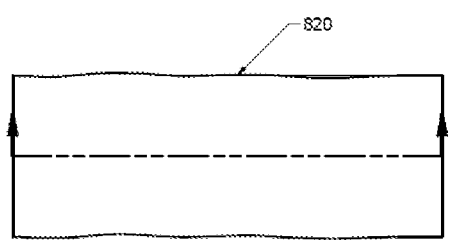

FIG. 236 is a side view illustration of the internal pathway of a patient.

Figure 237:
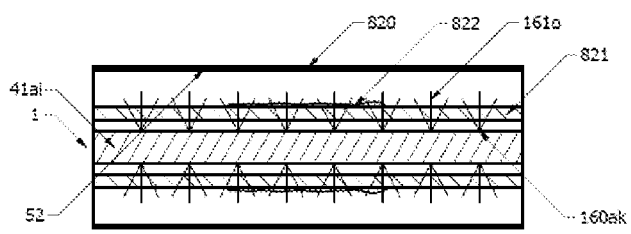

FIG. 237 is a cross-sectional view illustration of the sterile site apparatus and tubular medical device within the internal pathway of a patient of FIG. 236.

Figure 238:
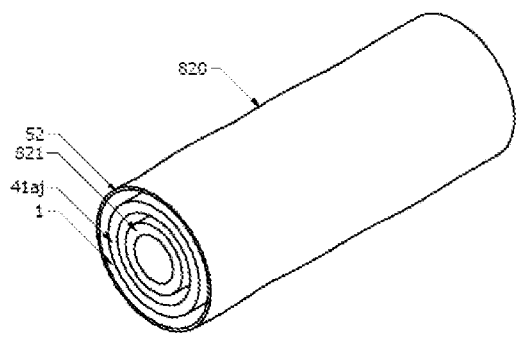

FIG. 238 is a pictorial view illustration of an embodiment of a sterile site apparatus and tubular medical device within the internal pathway of a patient.

Figure 239:
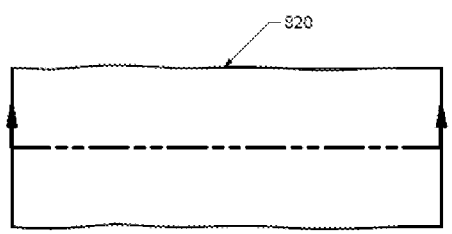

FIG. 239 is a side view illustration of the internal pathway of a patient.

Figure 240:
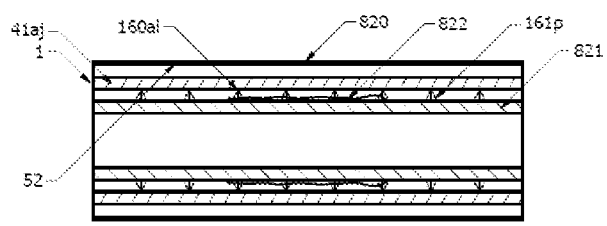

FIG. 240 is a cross-sectional view illustration of the sterile site apparatus and tubular medical device within the internal pathway of a patient of FIG. 239.

Figure 241:
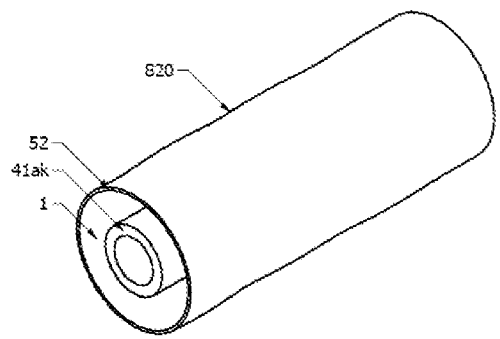

FIG. 241 is a pictorial view illustration of an embodiment of a sterile site apparatus within the internal pathway of a patient.

Figure 242:
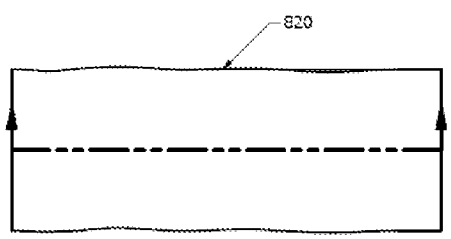

FIG. 242 is a side view illustration of the internal pathway of a patient.

Figure 243:
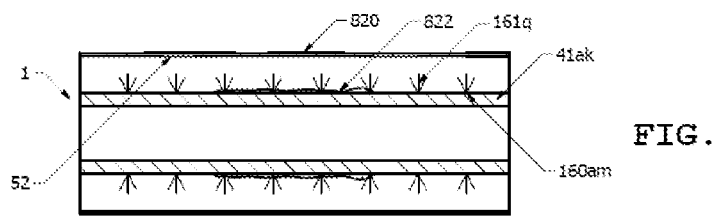

FIG. 243 is a cross-sectional view illustration of the sterile site apparatus within the internal pathway of a patient of FIG. 242.

Figure 244:
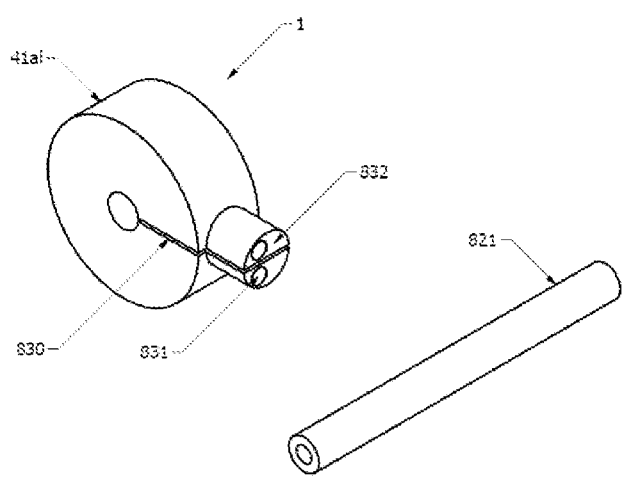

FIG. 244 is a pictorial view illustration of an embodiment of a sterile site apparatus before it is attached to a tubular medical device.

Figure 245:
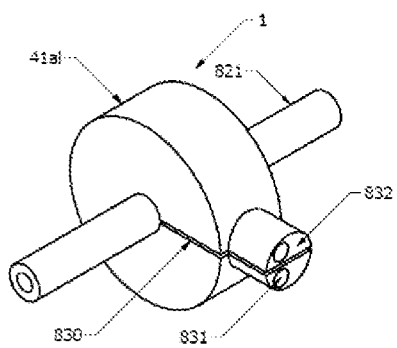

FIG. 245 is a pictorial view illustration of the sterile site apparatus after it is attached to a tubular medical device.

FIG. 246 is a front view illustration of the sterile site apparatus attached to a tubular medical device and placed in proximity to the patient.

FIG. 247 is a cross-sectional view illustration of the sterile site apparatus of FIG. 246 highlighting its internal feature including its transmission and emission medium.

FIG. 248 is a cross-sectional view illustration of the sterile site apparatus of FIG. 246 highlighting its internal features and ability to emit an EMR barrier into a tubular medical device and a contaminated region.

FIG. 249 is a front view illustration of an embodiment of a sterile site apparatus attached to a tubular medical device and placed in proximity to the patient.

FIG. 250 is a cross-sectional view illustration of the sterile site apparatus of FIG. 249 highlighting its internal features including its heating element.

FIG. 251 is a cross-sectional view illustration of the sterile site apparatus of FIG. 249 highlighting its internal features and ability heat the tubular medical device and proximal regions of the patient.

Figure 252:
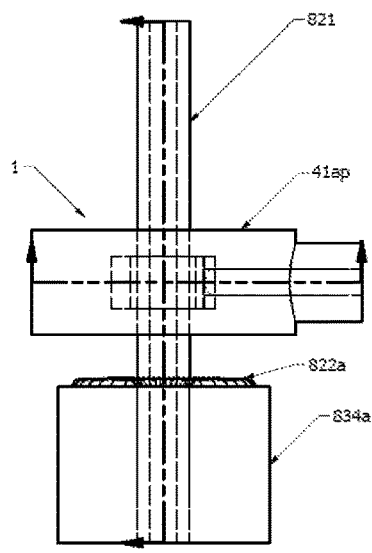

FIG. 252 is a front view illustration of an embodiment of a sterile site apparatus attached to a tubular medical device and placed in proximity to the patient.

Figure 253:
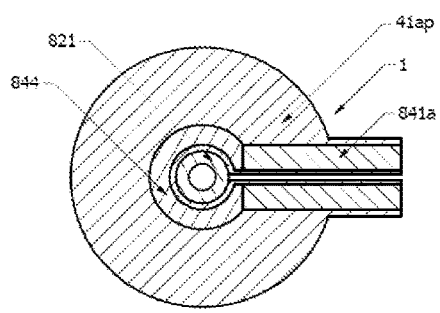

FIG. 253 is a cross-sectional view illustration of the sterile site apparatus of FIG. 252 highlighting its internal features including its electromagnetic field generator.

Figure 254:
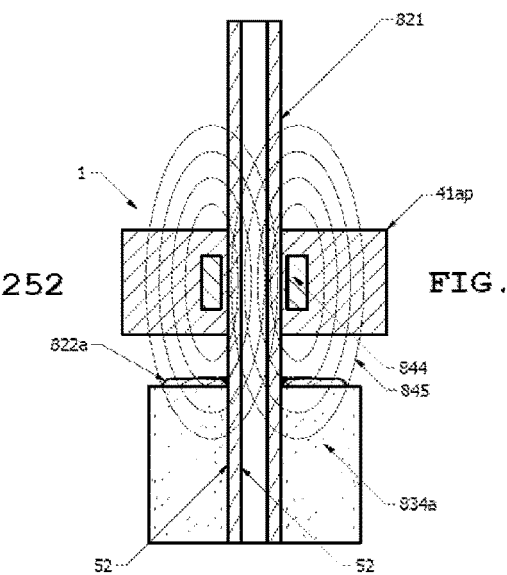

FIG. 254 is a cross-sectional view illustration of the sterile site apparatus of FIG. 252 highlighting its internal features and ability to create an electromagnetic field, which acts on the tubular medical device and proximal regions of the patient.

Figure 255:
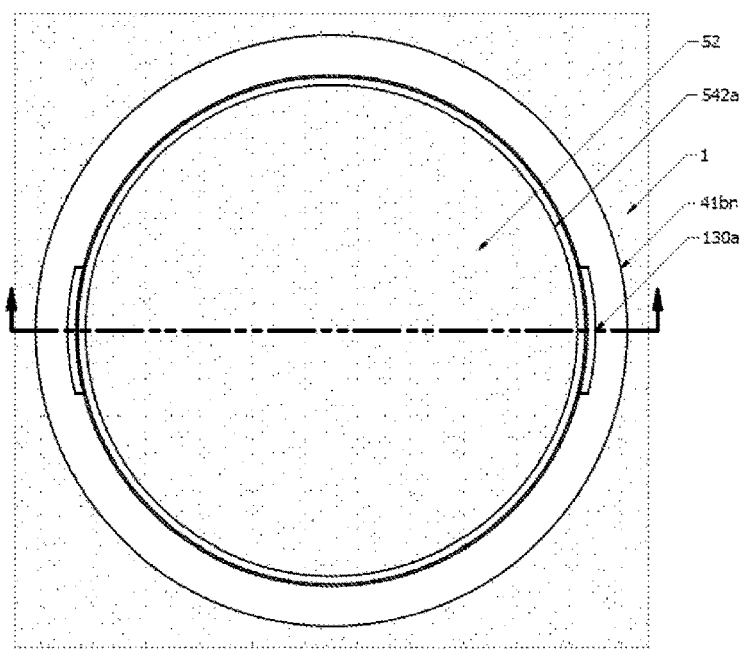

FIG. 255 is a top view illustration of an embodiment of a sterile site apparatus positioned over the sterile site.

Figure 256:
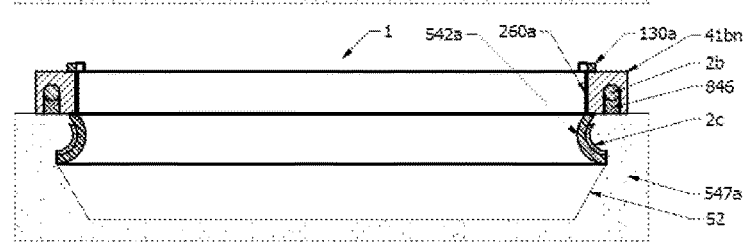

FIG. 256 is a cross-sectional view illustration of the sterile site apparatus of FIG. 252 highlighting its features including as retracting feature, heating elements, and coatings.

Figure 257:
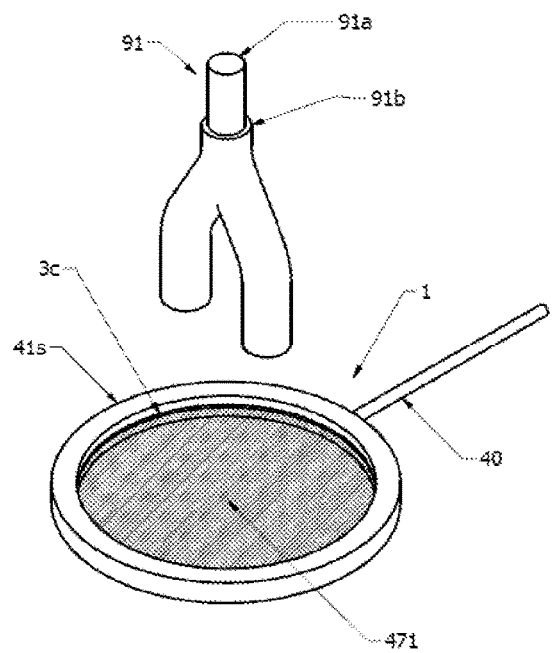

FIG. 257 is a pictorial view illustration of an embodiment of a sterile site apparatus, its unbroken detecting region of the object sensor, and an object.

Figure 258:
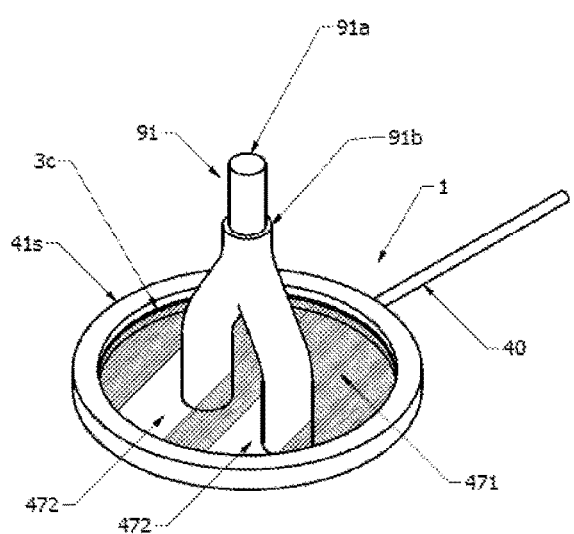

FIG. 258 is a pictorial view illustration of the sterile site apparatus of FIG. 257 after an object has disrupted the detecting region.

Figure 259:
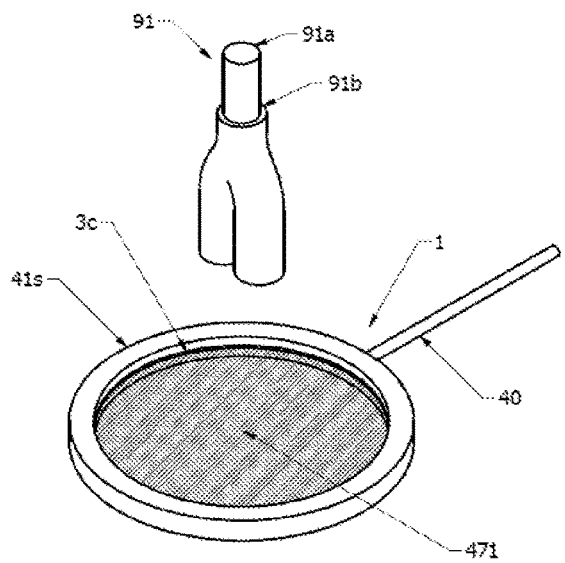

FIG. 259 is a pictorial view illustration of the sterile site apparatus, its unbroken detecting region of the object sensor, and an object.

Figure 260:
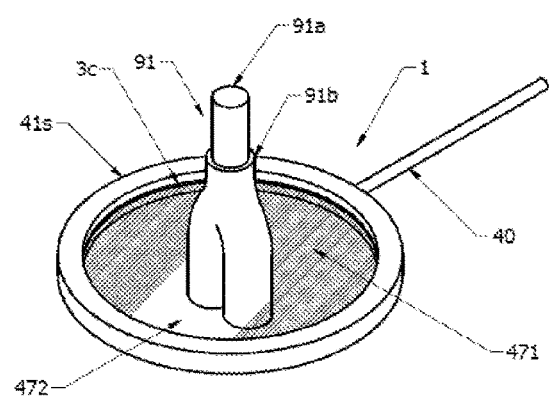

FIG. 260 is a pictorial view illustration of the sterile site apparatus of FIG. 259 after an object has disrupted the detecting region.

FIG. 261 is a top view illustration of an embodiment of a sterile site apparatus highlighting its various features.

FIG. 262 is a cross-sectional view illustration of the sterile site apparatus of FIG. 196 highlighting its various features.

FIG. 263 is an enlarged view illustration of the sterile site apparatus of FIG. 262 highlighting its various features.

Figure 77:
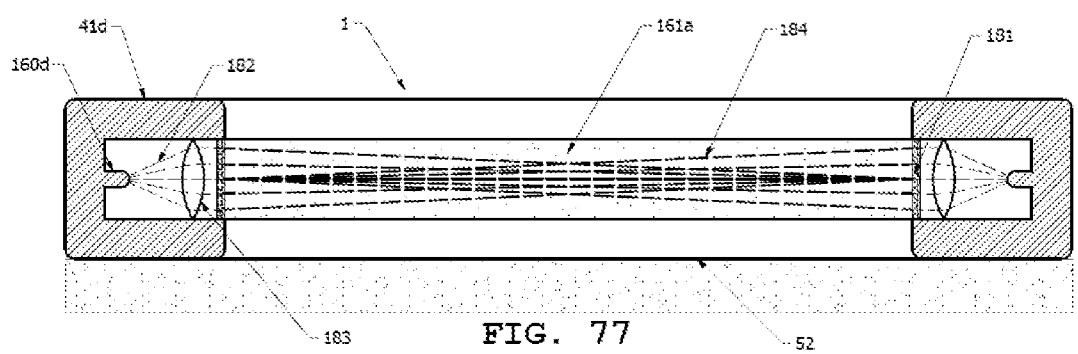
FIG. 77 is a cross-sectional view illustration of an embodiment of a sterile site apparatus to show that a coherent EMR barrier composed of convergent beams of EMR can be formed by using a lens in conjunction with EMR emitted from a point source EMR emitter.

FIG. 264 is a cross-sectional view illustration of the embodiment of the sterile site apparatus shown in FIG. 77 to illustrate selected features of the sterile site apparatus.

DETAILED DESCRIPTION OF THE INVENTION

Many alterations and modifications may be made to embodiments disclosed herein by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Figure 1:
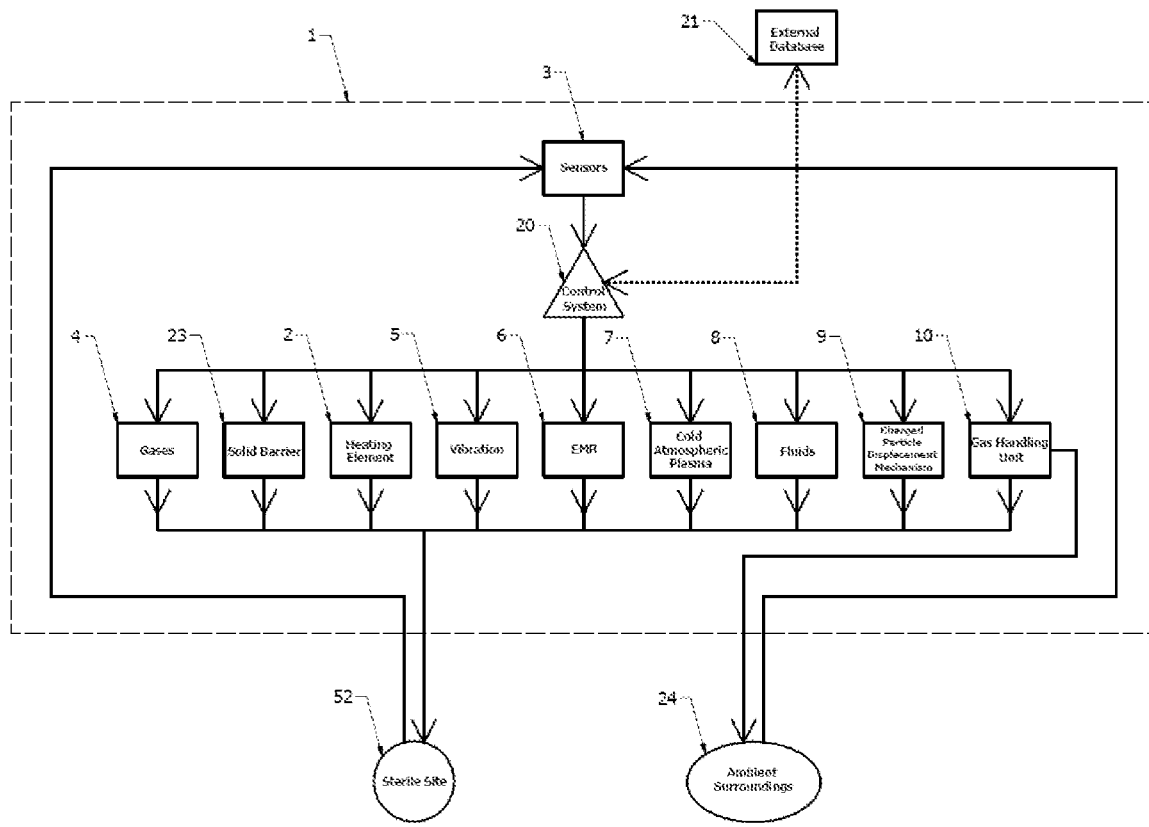
FIG. 1 is a diagram describing the features and systems used by an embodiment of a sterile site apparatus.

FIG. 1 illustrates a diagram for the various features and equipment used by the sterile site apparatus 1. A portion of the sterile site apparatus 1 will surround or partially surround the sterile site 52 and/or nearby regions. For the purposes of this invention, the sterile site 52 is any point, line, curve, area, surface, or volume where it is desirable to minimize the number, quantity, or amount of infectious agents. Examples of sterile sites 52 are a sterile field commonly used during a surgical or catheterization procedure where the surgical instruments or catheters are placed for use by the physician, or a surgical site which could be a wound, or surgical incision, or place where catheters, ports, or laparoscopic devices are inserted or implanted, or a laceration, epidermal trauma, pressure sore, or ulcer either external or internal to the body, or a portion of the body, bed, or room where the transfer of infectious agents could result in internal infection of the body, or the space within a hood or glove bag, the contents of a medicine bottle, or a catheter inner or outer surface such as a urinary catheter, or a catheter hub such as a central venous line, or port for chemotherapy, or a luer fitting, or a tubing line used for IV administration, or an endotracheal tube or tracheostomy tube or fitting. The intention of the sterile site apparatus 1 is to reduce or prevent infections or disease from originating at the sterile site 52. This entails reducing or preventing infectious agents from coming into contact with the sterile site 52, or rendering any infectious agents that enter the sterile site 52 ineffective at causing infection or disease.

For the purposes of this invention, infectious agent or infectious agents will mean any particle, particulate, or any single, multicell, or acellular organism or micro-organism, living or dead, including but not limited to bacteria, fungi, arcaea, spores, protozoa, protists, algae, plants, animals, plankton, planarian, helminthes, and infectious biological agents such as viruses, virions, viroids, plasmids, prions, or other autonomous or semi-autonomously replicating genome that is alone, or in combination with other infectious agents, airborne, in a gas, in or on a fluid, attached to an object such as a hand, forearm, body part, body article, surgical glove, instrument, catheter, fitting, or any other article that is able to cause infection or disease to a living body such as an animal or human.

FIG. 1 shows where the inputs and outputs of the various systems and features of the sterile site apparatus 1 can be directed. However, it should be noted that the sterile site apparatus 1 can include other features and systems than those shown in FIG. 1. While the sterile site apparatus 1 may use a variety of configurations, the configuration displayed in FIG. 1 shows the control system 20 receiving inputs from the sensors 3 and the external database 21. The control system 20 also sends information to the external database 21 before the control system 20 sends signals to other features and systems of the sterile site apparatus 1 including but not limited to gases 4, solid barrier 23, heating element 2, vibration 5, Electro Magnetic Radiation (EMR) 6, Cold Atmospheric Plasma (CAP) 7, fluids 8, charged particle displacement mechanism 9, and gas handling unit 10. The outputs from the features and systems of the sterile site apparatus 1 including but not limited to gases 4, solid barrier 23, heating element 2, vibration 5, Electro Magnetic Radiation (EMR) 6, Cold Atmospheric Plasma (CAP) 7, fluids 8, charged particle displacement mechanism 9, and gas handling unit 10 will be used for functions and applications involving the sterile site 52. The outputs from the gas handling unit 10 can also be used for functions and applications involving the ambient surroundings 24. For the purposes of this invention, ambient surroundings 24 will mean any point, line, curve, area, surface or volume that is not included part of the sterile site 52 that may or may not contain infectious agents. The sensors 3 will gather information on the sterile site 52, sterile site apparatus 1, infectious agents or objects near or in contact with the sterile site 52, regions near the sterile site 52 or sterile site apparatus 1, the ambient surroundings 24, and the current outputs of the features and systems of the sterile site apparatus 1. Information from the sensors 3 will then be sent to the control system 20. Greater detail on the functions and advantages of the features and systems of the sterile site apparatus 1 can be found below.

The heating element 2 will be used to heat air near the sterile site apparatus 1 or provide heating or a reduction of heat to or around the sterile site 52. Heated air will create an upward draft that is driven by density and/or pressure differences in the air. This upward draft of air is advantageous because it will carry falling infectious agents away from the sterile site 52. When the heating element 2 is used to heat or cool the sterile site apparatus 1 and associated objects, devices, or tissue around the sterile site 52, it minimizes infectious agents or their reproduction by creating a barrier of elevated or reduced temperature. The heating element 2 can create heat by any known means including but not limited to a resistance heater, radiofrequency heating, chemical heating by combustion or an exothermic reaction, and be transferred to the sterile site by means of conduction, convection, or radiance. It is also conceived that heating element can create a reduction in heat by any known means including but not limited to a thermoelectric device (Peltier effect), a heat sink, or an endothermic reaction and can be transferred to the sterile site by means of conduction, convection, or radiance. Gases 4 can be used by the sterile site apparatus 1 to serve a variety of functions including but not limited to disinfecting infectious agents, creating a barrier that infectious agents cannot pass through, or displacing infectious agents away from the sterile site 52. For example, ozone gas, which has applications as a disinfectant, can be pumped near the sterile site 52 to aid in the disinfection of infectious agents. Other gases that are bacteriostatic such as $CO_2$ or nitrous oxide can serve to minimize bacteria formation as well as the potential for air embolism. Bactericidal gases such as hypochlorous acid gas, hydrogen peroxide gas, and ozone can be quickly and efficiently neutralized with EMR so that they do not escape into the ambient surroundings 24. Wavelengths and frequencies of Electro Magnetic Radiation, EMR 6, will be used for a variety of purposes. One of the desired wavelength and frequency ranges, such as Ultraviolet (UV-C) light around 200-280 nm can be used to disinfect infectious agents near the sterile site 52. Another wavelength and frequency range, such as vacuum UV around 185 nm can be used to generate ozone gas near the sterile site 52. Other types of EMR 6 other than vacuum or UVC light can also be used such as UVB, UVA, blue light, microwave, broad spectrum pulsed light (BSPL), pulsed electrical field (PEF), alternating current electric field, direct current electric field, a high frequency electric field, x-ray, or infrared light as determined suitable for reducing infectious agents near the sterile site 52. Cold Atmospheric Plasma (CAP) 7 will also be used to create ozone gas and other conditions that will aid in disinfecting infectious agents. Fluids 8 can also be used to enhance the infection preventing effectiveness of the sterile site apparatus 1. The Fluids 8 include gases and gas mixtures, gas and liquid mixtures, liquids and liquid mixtures, gas and solid mixtures, and liquid and solid mixtures. Fluids 8 can be used by the sterile site apparatus 1 to serve a variety of functions including but not limited to disinfecting infectious agents, creating a barrier that infectious agents cannot pass through, or displacing infectious agents away from the sterile site 52. For example, fluids 8 can include humidified gas, ozonated water vapor, ozonated water, CAP activated water vapor, CAP activated water, surface disinfectants, antiseptics, antibiotics, antifungal agents, antiviral agents, preservatives, bacteriostatic agents, and bactericides. A charged particle displacement mechanism 9 will operate by charging incoming infectious agents either positively or negatively. A component that has the same or opposite charge of the infectious agents will then either attract the infectious agents to a receptor, or repel the infectious agents away from the sterile site 52. A gas handling unit 10 will be used to provide purified or sterile gas to the sterile site apparatus 1. Multiple purified or sterile gases can be released by the gas handling unit 10, however purified or sterile air is preferable due to its availability. A solid barrier 23 made of solid materials will be used to create a barrier to partially or completely cover the sterile site 52 in order to protect the sterile site 52 from the infectious agents. The solid barrier 23 will be designed so that it will cover the sterile site 52 in a manner that will not inhibit the user from performing a desired task. For example, it is conceivable that the solid barrier 23 will only be created when a medical device or a user's hand is not in contact with the sterile site 52. Vibration 5 will be used to for a variety of functions including but not limited to nebulizing disinfecting fluids, preventing development of biofilm on a surface, and preventing infectious agents from resting on the sterile site 52.

The various features and systems of the sterile site apparatus 1 will be activated or deactivated by the control system 20. The control system 20 will have the capability to incorporate sensors 3 and other systems which can detect when objects are near the sterile site 52, when there are changes in conditions at or near the sterile site 52 which warrants the systems to turn on or adjust such as when a physician or staff member is in the room where a medical procedure is being conducted so as to the levels/concentrations of EMR, fluid mixtures and gas mixtures being released by the sterile site apparatus 1. Detecting objects immediately near the sterile site 52 is beneficial because it may not be desirable to have certain features of the sterile site apparatus 1, such as emitting EMR, constantly activated. Controlling the activation of the features will be beneficial by prolonging the service life of the sterile site apparatus 1 and limiting the exposure of EMR to the patient and physician(s). Detecting physicians or staff members in the room where a medical procedure is going to be performed is beneficial because it can allow certain features, such as the gas handling unit 10, to be activated before a medical procedure is performed. This would allow the ambient surroundings 24 to be cleaned before a medical procedure is performed. Additional sensors, systems, and controls such as foot switches, voice, and remote activated control and any others besides those mentioned, can also be incorporated into the control system 20. The sensor 3 may be one or many and be the same or different from each other, it may be located close to the sterile site 52, be within the sterile site equipment 27, or be remotely located. The sensor 3 may be able to measure objects so as to determine size, shape, color, density, and other material and physical attributes. It is conceivable that the sensor 3 will be able to measure other properties of objects such as their position, position relative to another object so as to determine if objects are touching, velocity, chemistry, and temperature so as to be able to provide intelligent information to the control system 20, which will serve to activate or deactivate various features of the sterile site apparatus 1. Furthermore, the sensor 3 may be able to provide information about the condition of the sterile site apparatus 1 itself and its related outputs, such as pressures, concentrations, voltage, energy level, flow, temperature, orientation, and geometry. This ability to provide the control system 20 with feedback from sensors 3 is advantageous because it will provide input necessary to ensure that the sterile site apparatus 1 is performing as expected. The control system 20 will be technologically advanced so as to be able to make decisions from the inputs of the sensor 3 and combined with information provided from the external database 21 such as the internet, a database, or a live operator, be able to appropriately adjust the outputs of the sterile site apparatus 1. For example, ozone gas can be pumped near the sterile site 52 to aid in the disinfection of infectious agents for a controlled amount of time determined by the control system 20 when an object is sensed by the sensor 3. As another example, the sensor 3 may detect a rise in temperature at the sterile site 52, and initiate a timed beam of UV light to the site while outputting a warning signal to a cellular phone or other user interface that would alert the user of a new possible infectious condition.

Figure 2:
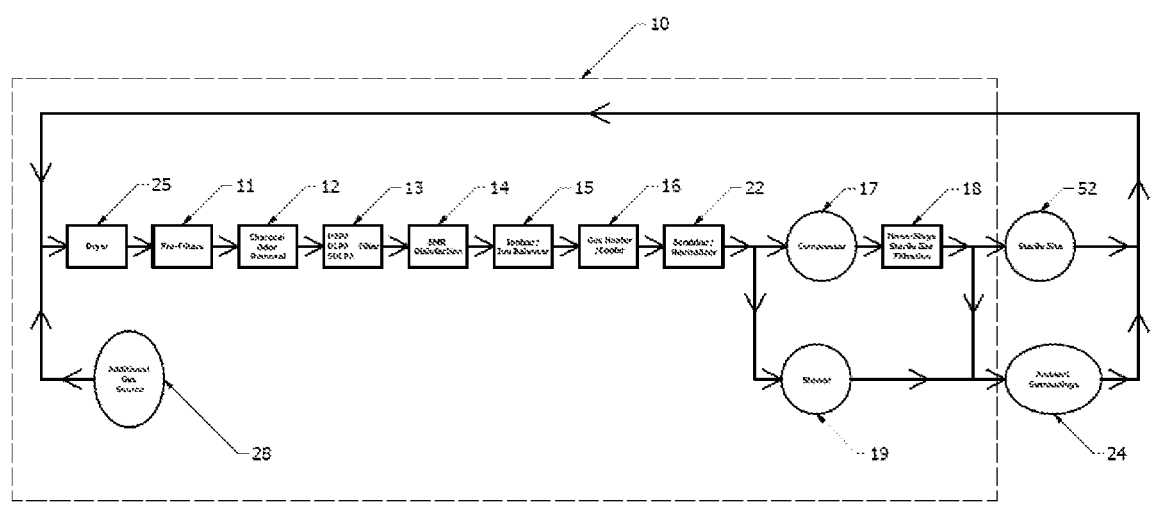
FIG. 2 is a diagram describing the features and systems of an embodiment of a gas handling unit.

FIG. 2 illustrates a flow chart describing the gas handling unit 10 features and systems used to process intake gas to yield sterile gas and/or purified gas. The intake gas will be drawn from the sterile site 52, ambient surroundings 24, and/or the additional gas source 28. The additional gas source 28 can provide a variety of gases including but not limited to $CO_2$, ozone gas, and inert gases. Sterile gas will be defined as gas being free of at least 99.99% of all infectious agents greater than 0.01 microns. Filtering out objects larger than 0.01 microns is desired because some of the smallest known infectious agents, such as the pelagibacter ubique and parvovirus, have their smallest dimensions (0.012 and 0.018 microns, respectively) greater than 0.01 microns. Purified gas will be defined as gas being free of at least 99.97% of all infectious agents greater than 0.3 microns. Sterile gas will be used for applications involving the sterile site 52 or the ambient surroundings 24. These applications will be discussed in further detail in other embodiment descriptions. Purified gas will be circulated back into the ambient surroundings 24 to enhance overall sanitation. The gas handling unit 10 will consist of a dryer 25, pre-filters 11, a charcoal odor removal system 12, a HEPA/ULPA/SULPA filter 13, an EMR disinfection system 14, an ionizer/ion balancer 15, a gas heater/cooler 16, a scrubber/neutralizer 22 and a gas blower 19 for creating purified gas. The gas handling unit 10 will consist of a dryer 25, pre-filters 11, a charcoal odor removal system 12, a HEPA/ULPA/SULPA filter 13, an EMR disinfection system 14, an ionizer/ion balancer 15, a gas heater/cooler 16, a scrubber/neutralizer 22, a compressor 17, and a three-stage sterile gas filtration system 18 for creating sterile gas.

The dryer 25 will remove moisture and humidity from the incoming gases. The pre-filters 11 will remove large infectious agents from the incoming gases. The charcoal odor removal system 12 will remove odors from the gases. The HEPA/ULPA/SULPA filter 13 will remove fine infectious agents from the incoming gases. A HEPA filter will be defined as being capable of removing 99.97% of all infectious agents greater than 0.3 microns. An ULPA filter will be defined as being capable of removing 99.999% of all infectious agents of the most penetrating particle size at a specified gas velocity. A SULPA filter will be defined as being capable of removing 99.9999% of all infectious agents of the most penetrating particle size at a specified gas velocity. The most penetrating particle size is defined as the approximate particle diameter when penetration through the filter is highest. The EMR disinfection system 14 will use specific wavelength(s) of EMR (typically UVC radiation in the range of 200-280 nm) to disinfect infectious agents in the gases. The ionizer/ion balancer 15 will create a desired ion balance in the gases to promote health benefits for the patient and physician(s) and to assist with the charged particle displacement mechanism. The gas heater/cooler 16 will heat or cool the gas to a temperature that is comfortable for the patient and physician(s). The scrubber/neutralizer 22 will reduce the concentration of potentially harmful gases and substances in the incoming gas. After passing through the dryer 25, pre-filters 11, charcoal odor removal system 12, HEPA/ULPA/SULPA filter 13, EMR disinfection system 14, ionizer/ion balancer 15, gas heater/cooler 16, and scrubber/neutralizer 22, sterile gas will be created by running gas through a compressor 17 followed by forcing the gas through a three-stage sterile gas filtration system 18. In the three-stage sterile gas filtration system 18, gas will be pushed through openings that decrease in size from one stage to the next. The size of the openings in the final stage will be sufficiently small to prevent infectious agents from passing through, which will yield sterile gas. After passing through the dryer 25, pre-filters 11, charcoal odor removal system 12, HEPA/ULPA/SULPA filter 13, EMR disinfection system 14, ionizer/ion balancer 15, gas heater/cooler 16, and scrubber/neutralizer 22, purified gas will be yielded by running gas through a blower 19 to propel the gas back into the ambient surroundings. The gas handling unit 10 will have the ability to create sterile gas and purified gas simultaneously or independently. It would also be advantageous for the gas handling unit 10 to incorporate sensors and systems to monitor the sterile site apparatus's 1 outputs, including but not limited to gas pressure, temperature and composition, and conditions, including but not limited to filter obstruction and scrubber effectiveness. This information gathered by sensors and systems can conceivably be used to notify the user or other individual of a need for maintenance or repair, such as replacing a filter or diagnosing the cause of a gas leak, by activating alarms or other features. It should be noted that additional components and systems, which are not shown in FIG. 2, can be incorporated into the gas handling unit 10. The components and systems of the gas handling unit 10 can be arranged in multiple combinations, arrangements, and orders and can be omitted in order to produce the most optimum configuration for a particular need.

One embodiment of the gas handling unit 10 utilizes a combination of $CO_2$ from the additional gas source 28, which is heated by the gas heater/cooler 16 to a temperature in the range of 105 degrees F. to 125 degrees F. and administered to the sterile site 52. This increased temperature heats the sterile site 52 above the normal body temperature which greatly reduces the growth of bacteria, and simultaneously stimulates increased blood flow thereby enhancing the body's own defenses for fighting bacteria. CO2 gas offers the advantage of being bacteriostatic and reducing the potential for air embolism if venous or arterial vessels have been accessed in the sterile site 52.

Figure 3:
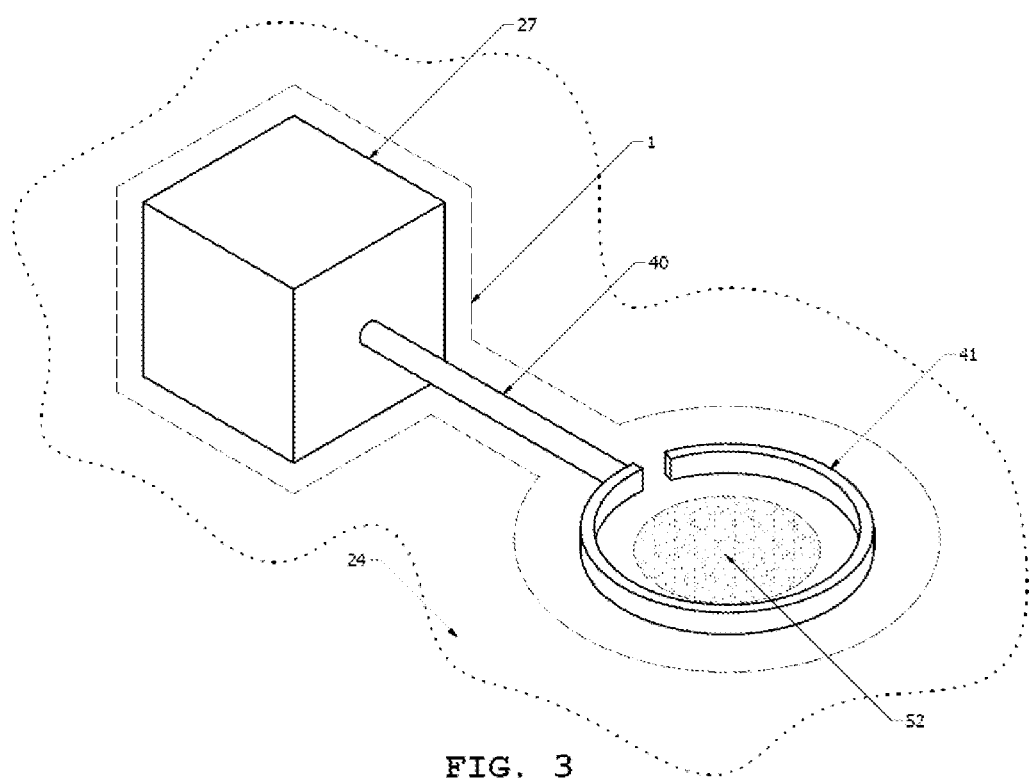
FIG. 3 is a pictorial view illustration of an embodiment of a sterile site apparatus.
Figure 4:
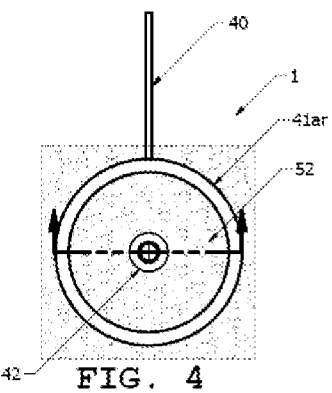
FIG. 4 is a top view illustration of an embodiment of a vacuum head positioned above the sterile site apparatus and sterile site.
Figure 6:
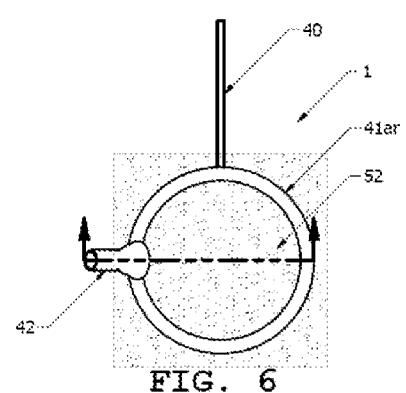
FIG. 6 is a top view illustration of the vacuum head positioned above and at an angle to the sterile site apparatus and sterile site.
Figure 5:
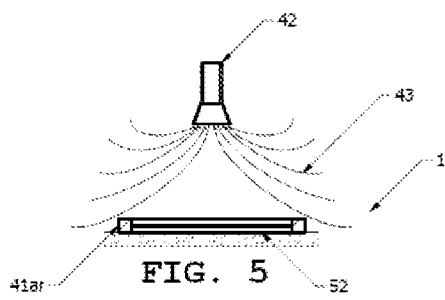
FIG. 5 is a cross-sectional view illustration of the vacuum head and sterile site apparatus of FIG. 4 while the vacuum head is removing infectious agent containing air surrounding the sterile site.
Figure 7:
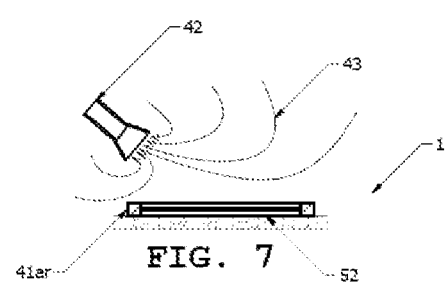
FIG. 7 is a cross-sectional view illustration of the vacuum head and sterile site apparatus of FIG. 6 while the vacuum head is removing infectious agent containing air surrounding the sterile site.
Figure 8:
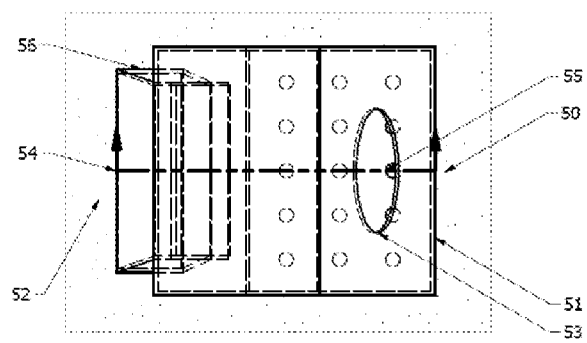
FIG. 8 is a top view illustration of an embodiment of a collapsible vacuum head attached near the sterile site using suction.
Figure 9:
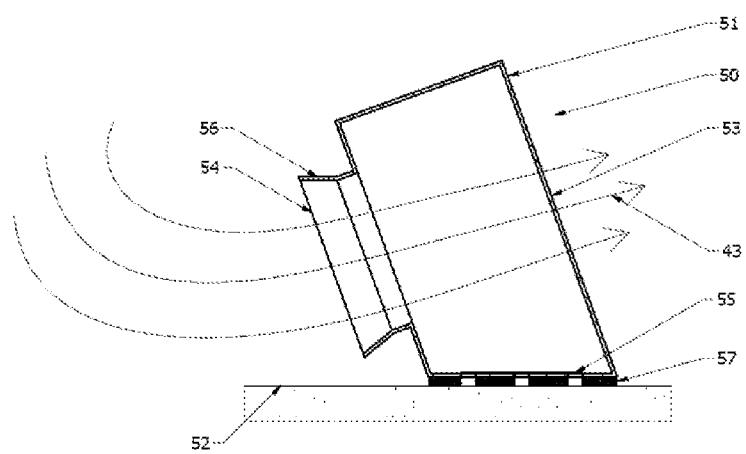
FIG. 9 is a cross-sectional view illustration of the collapsible vacuum head of FIG. 8 while it is removing infectious agent containing air surrounding the sterile site.

FIG. 3 illustrates a sterile site apparatus 1 to reduce the amount of infectious agents entering a sterile site 52. It should again be noted that although figures and discussions contained in this disclosure may show or specify a specific type of sterile site 52, such as a sterile field or surgical site, the sterile site apparatus 1, can be used for applications involving all types of sterile sites 52. In FIG. 3, the sterile site equipment 27 is connected to the housing 41 via the supply cord 40. The housing 41 can be a rigid, flexible, malleable, collapsible, or inflatable structure and can be composed of a single piece or multiple pieces. The housing 41 may also have any of a number of cross-sectional profiles. The housing 41 may or may not be fully enclosed, may or may not surround the sterile site 52, and may be made of one or a combination of multiple materials such as plastic, elastomer, rubber, fabric, fiber, glass, ceramic, metal or composite. The role of the housing 41 is to provide a structure to aid the sterile site apparatus 1 in performing its various functions. The housing 41 may be configured to surround or partially surround the sterile site 52, and may be attached to a surrounding area by means of adhesives, magnets, suction, grip pads, mechanical devices, or other known methods. The housing 41 may be configured to be located a distance away from the sterile site 52 to be more applicable for reducing infectious agents on objects that may later enter the sterile site 52. From the housing 41, the sterile gases, fluid mixtures, EMR, CAP and other features of the sterile site apparatus 1 will be utilized to displace the infectious agents away from the sterile site 52 or render the infectious agents unable to cause infection or disease. It should be noted that the sterile site apparatus 1 is surrounded by the ambient surroundings 24, which can contain infectious agents.

If infectious agents come into contact with objects in or entering the sterile site 52, it will be beneficial to disinfect the objects so that the infectious agents are unable to cause infection or disease. This disinfection may be accomplished by administering ozone gas, CAP, fluids, or the desired wavelength(s) of EMR. The role of the supply cord 40 is to provide the housing 41 or other part(s) of sterile site apparatus 1 with the necessary materials, gases, liquids, solids, mixtures, electrical power, EMR, CAP, and/or inputs and outputs needed to perform its variety of functions. It should be noted that although the supply cord 40 is shown in FIG. 3 to be connected to the sterile site equipment 27 and housing 41, the supply cord 40 can be connected to a variety of other components, sources, or systems in addition to, in combination with, or in place of the sterile site equipment 27, or not be required at all if the sources, systems, controls, and components are incorporated in, on, or attached to the housing 41. For the purposes of this invention disclosure, the remaining figures will not show the sterile site equipment 27 connected to the supply cord 40.

FIGS. 4-7 illustrate the gas handling unit's 10 (FIG. 2) ability to remove infectious agent containing air 43 away from the sterile site 52. The sterile site apparatus 1 consists of a supply cord 40 and housing 41ar. The vacuum head 42 is shown in FIGS. 4-7 to depict that it can be arranged in any number of orientations and placements with respect to the sterile site apparatus 1 and sterile site 52. Infectious agent containing air 43 will be pulled into the vacuum head 42 and sent to the gas handling unit via a connecting hose (not shown). It is also contemplated that compressed air from the gas handling unit 10 can be used to generate a vacuum effect by blowing into the vacuum head 42 and pulling the infectious agent containing air 43 with it. The advantage of blowing compressed air to create the negative pressure at the sterile site 52 is that the connecting hose (not shown) would have less of a tendency to collapse due to having a higher pressure than the surrounding ambient air. The gas handling unit and vacuum head 42 will be designed and positioned so that no infectious agents will be able to come into contact with the sterile site 52. The vacuum head 42 may be connected to the supply cord 40, housing 41ar, or be supported by another structure to allow the proper positioning in proximity to the sterile site 52. The vacuum head 42 can work alone or work in combination with other embodiments of the sterile site apparatus 1 as will be disclosed in this specification. It should also be noted that the vacuum head 42 can also be used to exhaust gases 4 (FIG. 1), CAP 7 (FIG. 1) gases, sterile or purified gas from the gas handling unit 10 (FIG. 1), and fluids 8 (FIG. 1) that may be present at or near the sterile site 52.

Figure 10:
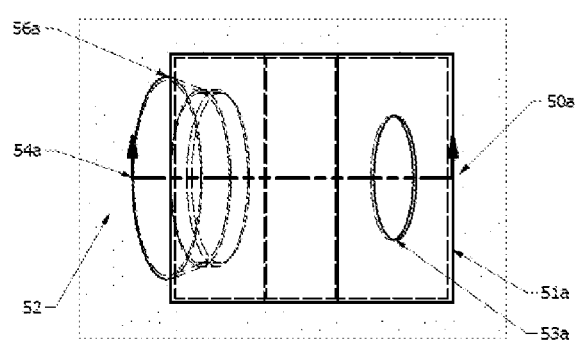
FIG. 10 is a top view illustration of the collapsible vacuum head attached near the sterile site using two grip pads.
Figure 11:
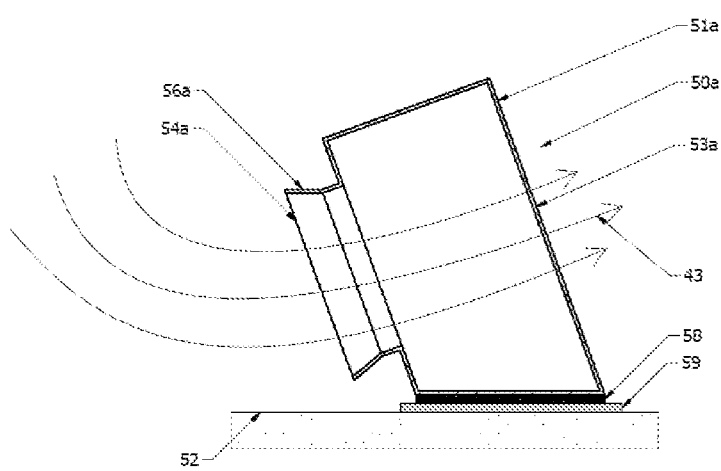
FIG. 11 is a cross-sectional view illustration of the collapsible vacuum head of FIG. 10 while it is removing infectious agent containing air surrounding the sterile site.
Figure 12:
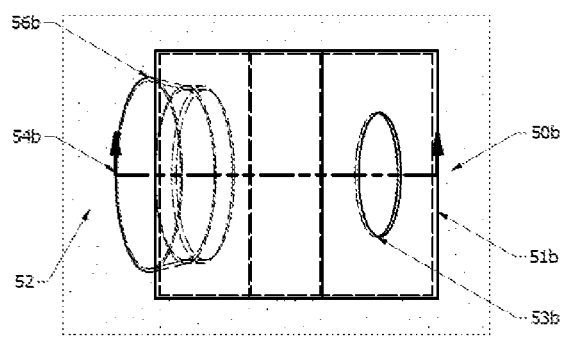
FIG. 12 is a top view illustration of the collapsible vacuum head attached near the sterile site using two oppositely charged magnetic pads.
Figure 13:
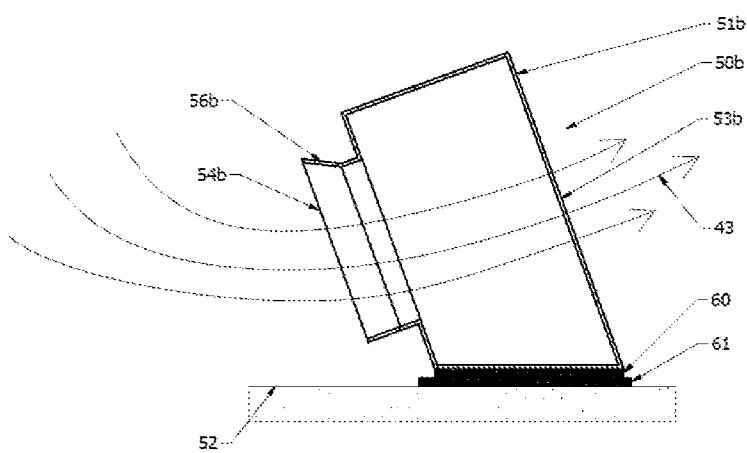
FIG. 13 is a cross-sectional view illustration of the collapsible vacuum head of FIG. 12 while it is removing infectious agent containing air surrounding the sterile site.

FIGS. 8-13 illustrate the gas handling unit's 10 (FIG. 2) ability to use a collapsible vacuum head 50, 50a, and 50b to remove infectious agent containing air 43 away from the sterile site 52 and its surrounding areas. The collapsible vacuum head 50, 50a, and 50b will be designed to be stored and shipped as a collapsed unit it will be used. Immediately before use, the collapsed unit can be folded to yield the collapsible vacuum head 50, 50a, and 50b seen in FIGS. 8-13. The infectious agent containing air 43 will flow through the inlet opening 54, 54a, and 54b to the main enclosure 51, 51a and 51b and through the outlet opening 53, 53a, and 53b, which will connect the collapsible vacuum head 50, 50a, and 50b to the gas handling unit via a connecting hose (not shown). The portion surrounding the inlet opening 54, 54a, and 54b will have foldable ends that will create a flared feature 56, 56a, and 56b to improve air flow. The flared feature 56, 56a and 56b can have any of a number of appearances and designs as seen in FIGS. 8-13. The collapsible vacuum head 50, 50a and 50b can be attached to or near the sterile site 52 by using suction applied through small openings 55 sealed by a gasket 57 seen in FIGS. 8-9, by using grip pads 58-59 as seen in FIGS. 10-11, or by using a positively charged magnetic pad 60 and a negatively charged magnetic pad 61 as seen in FIGS. 12-13. The gas handling unit and collapsible vacuum head 50, 50a, and 50b will be designed so that no infectious agents will be able to come into contact with the sterile site 52.

Figure 14:
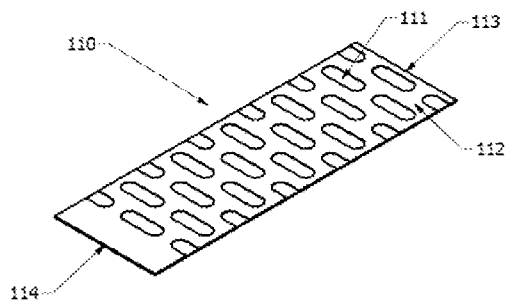
FIG. 14 is a pictorial view illustration of an embodiment of a deflated vacuum tube.
Figure 15:
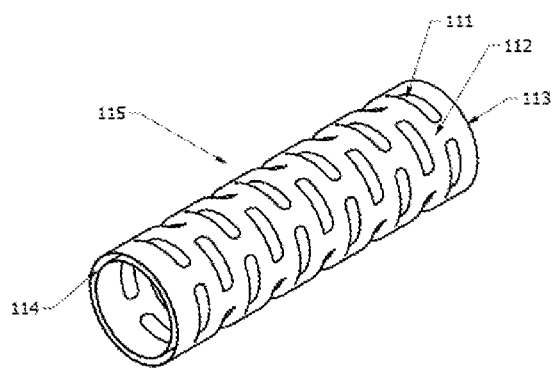
FIG. 15 is a pictorial view illustration of the inflated vacuum tube.

FIGS. 14-15 illustrate the ability for the deflated vacuum tube 110 to be filled with pressurized gas in the region where the two layers of tubing are not attached 112. Pressurized gas will be introduced between the two layers of tubing from the unsealed end 114 to inflate the tubing. The sealed end 113 will prevent pressurized gas from escaping from the opposite end of the tube. The resulting inflated vacuum tube 115 will maintain its shape from regions where the two layers of tubing are attached 111. Ambient air containing infectious agents near the sealed end 113 will flow through the center of the inflated vacuum tube 115 to the unsealed end 114 where the air will then be taken to the gas handling unit 10 (FIG. 2). Although not seen in FIGS. 14-15, the unsealed end 114 will be attached to a structure that will allow pressurized gas to flow into the region between the two layers of tubing without allowing pressurized gas to flow out of the region between the two layers of tubing.

FIGS. 16-18 illustrate a method for attaching the inflated vacuum tube with semi-rigid insertion card 126 to the gas handling unit 10 (FIG. 2). The device will consist of an inflated vacuum tube 115 connected to a semi-rigid insertion card 126. Pressurized gas will be introduced between the two layers of tubing from the unsealed end 114 (FIG. 15) to inflate the tubing. The sealed end 113 will prevent pressurized gas from escaping from the opposite end of the tube. The resulting inflated vacuum tube 115 will maintain its shape from regions where the two layers of tubing are attached 111. Ambient air containing infectious agents near the sealed end 113 will flow through the center of the inflated vacuum tube 115 to the unsealed end 114 where the air will then be taken to the gas handling unit 10. The outer layer 127 of the inflated vacuum tube 115 will be sealed to the left side of the semi-rigid insertion card 126 as seen in FIG. 17. The inner layer 128 of the inflated vacuum tube 115 will be sealed to the right side of the semi-rigid insertion card 126 as seen in FIG. 17. There will also be a pressurized gas hole 129 that will cross through the inner layer 128 of the inflated vacuum tube 115 and/or the semi-rigid insertion card 126. This hole will access the region where the two layers of tubing are not attached 112 to allow inflation of the inflated vacuum tube 115. For attaching the inflated vacuum tube with semi-rigid insertion card 126 to the gas handling unit, the semi-rigid insertion card 126 will be slid into or otherwise attached to a mating feature on the gas handling unit to allow for inflation via the pressurized gas hole 129, as shown in FIG. 18, and also allow the intake of infectious agent containing air through the center of the inflated vacuum tube 115.

FIGS. 19-20 illustrate the ability of the sterile site apparatus 1, which consists of a supply cord 40 connected to the housing 41as, to blow sterile gas 32 and/or ionized gas 73 to prevent infectious agents from coming into contact with the sterile site 52. The sterile gas 32 and/or ionized gas 73 will be propelled through gas release openings 31. The gas release openings 31 can consist of orifices, slits, vents and/or other shapes/arrangements and may release any of a number of gas mixtures including, but not limited to purified gas, sterile gas 32, ionized gas 73, ozone gas, humidified gas, carbon dioxide and CAP. While embodiments and figures of this document may specify the use of a specific gas, fluid, solid and/or CAP mixture, it should be noted that any combination of gases, fluids, solids and/or CAP may be used in its place. The released sterile gas 32 and/or ionized gas 73 will displace infectious agent containing air 43 away from the sterile site 52. The use of ionized gas 73 is desirable because it can cause infectious agents to be charged either positively or negatively. As will be discussed in other embodiments, charging the infectious agents can allow the sterile site apparatus 1 to repel or attract the infectious agents in a way to prevent contact with the sterile site 52. Additionally, if a cluster of infectious agents becomes charged in a way that the individual infectious agents all have the same charge, the cluster will tend to disintegrate as the individual infectious agents repel each other. This disintegration is advantageous because the small individual infectious agents will travel slowly through the air. When the infectious agents travel slowly, there will be a longer duration of time available for the sterile site apparatus 1 to disinfect or displace the infectious agents.

Figure 21:
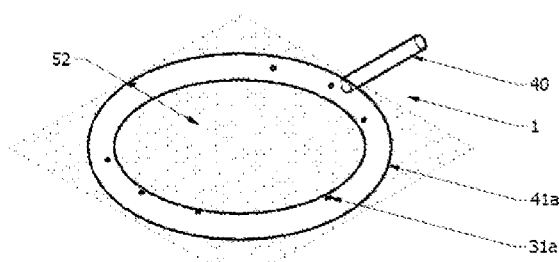
FIG. 21 is a pictorial view illustration of the sterile site apparatus that allows gas mixtures to be released in various directions.
Figure 22:
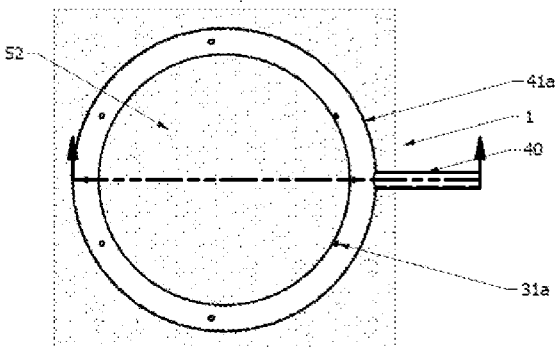
FIG. 22 is a top view illustration of the sterile site apparatus of FIG. 21.
Figure 23:
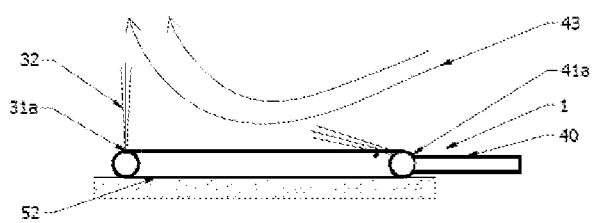
FIG. 23 is a cross-sectional view illustration of the sterile site apparatus of FIG. 22 while its gas release openings release a gas mixture in various directions to displace infectious agent containing air.

FIGS. 21-23 illustrate the ability of the sterile site apparatus 1 to blow sterile gas 32 in various directions and orientations to prevent infectious agent containing air 43 from coming into contact with the sterile site 52. By blowing gas in a non-uniform manner, it allows for a wider range of possible designs for the sterile site apparatus 1 and its gas release openings 31a. This will allow for better patient care by more effectively preventing infectious agents from coming into contact with the sterile site 52. It will also improve the comfort and performance of physician(s) by preventing gas from being blown in their direction, where it could cause discomfort and distraction. The shape and arrangement of the gas release openings 31a will be designed to prevent infectious agents from coming into contact with the sterile site 52. One preferred embodiment consists of gas release openings 31a, uniformly surrounding the perimeter of the housing 41a so that the sterile site 52 is completely surrounding by the flow of gas. The gas release openings 31a can have an opening diameter of 0.001" to 0.06", but preferably on the order of 0.010" with spacing between the gas release openings 31 ranging from 0.06" to 1" but preferably on the order of 0.25" to 0.5". The pressure of the sterile gas 32 can be in the range of 1 psi to 50 psi but is preferably on the order of 10 to 20 psi. The design of the sterile site apparatus 1 will take advantage of flow patterns and fluid phenomena that result from release and/or intake of fluids from/to the sterile site apparatus 1.

Figure 24:
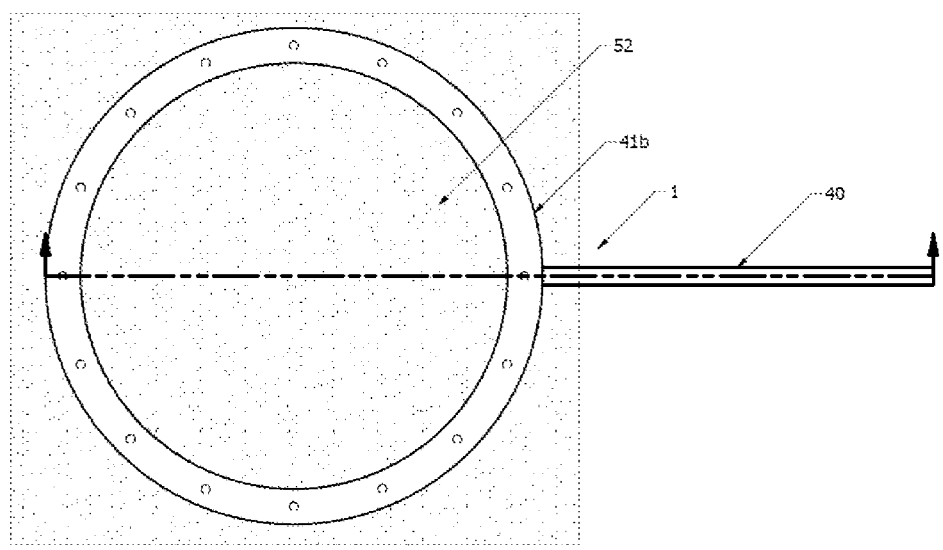
FIG. 24 is a top view illustration of an embodiment of a sterile site apparatus positioned above the sterile site.
Figure 25:
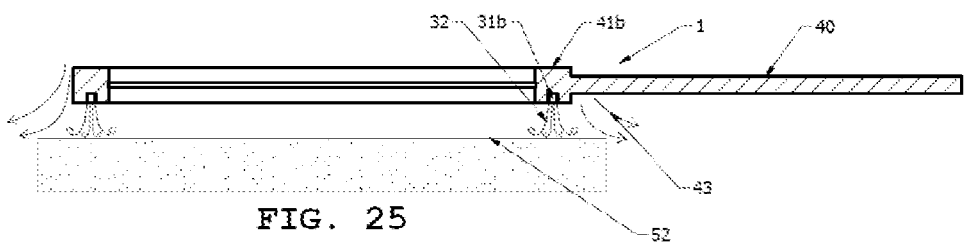
FIG. 25 is a cross-sectional view illustration of the sterile site apparatus of FIG. 24 while its gas release openings release a gas mixture to prevent infectious agent containing air from flowing under the housing of the sterile site apparatus.

FIGS. 24-25 illustrate the ability of the sterile site apparatus 1 to prevent infectious agent containing air 43 from traveling underneath the housing 41b and coming into contact with the sterile site 52. The sterile site apparatus 1 consists of a supply cord 40 and housing 41b. Sterile gas 32 will be released from gas release openings 31b in the housing 41b. When the sterile gas 32 is released, it will cause infectious agent containing air 43 to be propelled away from the sterile site 52. If this feature was not present and the sterile site apparatus 1 were to simply rest on top of a surface, it would be possible for infectious agents to come into contact with the sterile site 52 after traveling through gaps between the housing 41*b* and the sterile site 52.

Figure 26:
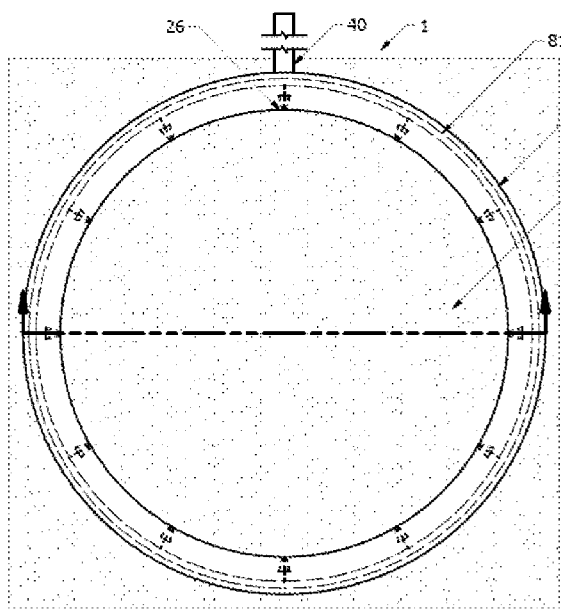
FIG. 26 is a top view illustration of an embodiment of a sterile site apparatus positioned above the sterile site.
Figure 28:
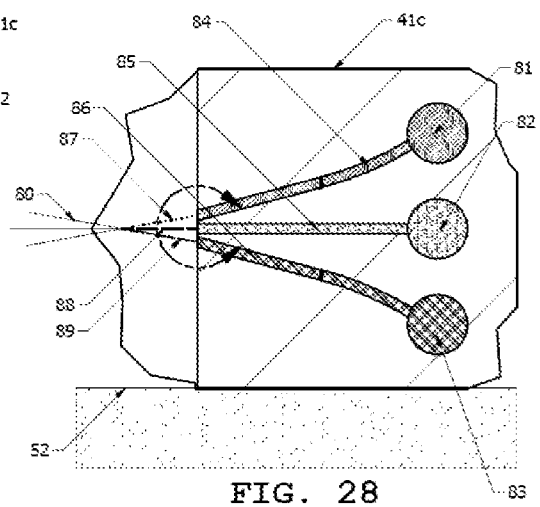
FIG. 28 is an enlarged view illustration of the sterile site apparatus of FIG. 27 highlighting the use of multiple lumens containing various fluids and materials.
Figure 27:
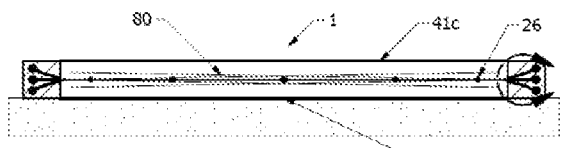
FIG. 27 is a cross-sectional view illustration of the sterile site apparatus of FIG. 26 while it forms a disinfecting fluid barrier created by the fluid release openings.
Figure 29:
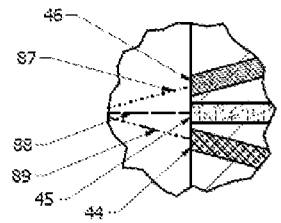
FIG. 29 is an enlarged view illustration of the sterile site apparatus of FIG. 28 highlighting a method used by the fluid release openings for mixing several fluids and materials.
Figure 30:
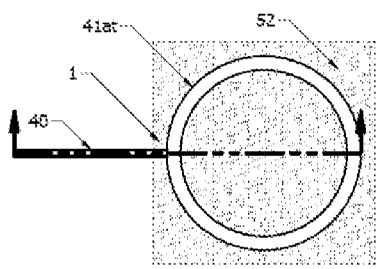
FIG. 30 is a top view illustration of an embodiment of a sterile site apparatus before it creates an extended fluid barrier over the sterile site.
Figure 32:
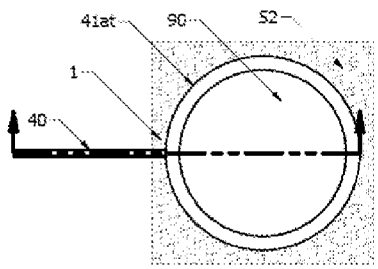
FIG. 32 is a top view illustration of the sterile site apparatus after it creates an extended fluid barrier over the sterile site.
Figure 34:
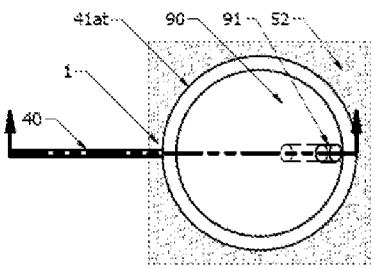
FIG. 34 is a top view illustration of the sterile site apparatus while an object passes through the extended fluid barrier.
Figure 31:
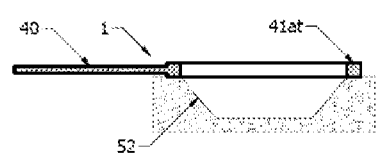
FIG. 31 is a cross-sectional view illustration of the sterile site apparatus of FIG. 30.
Figure 33:
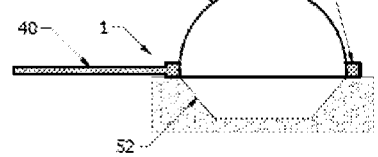
FIG. 33 is a cross-sectional view illustration of the sterile site apparatus of FIG. 32.
Figure 35:
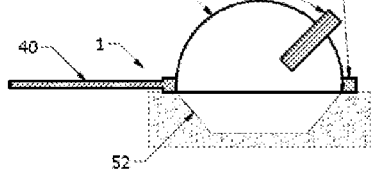
FIG. 35 is a cross-sectional view illustration of the sterile site apparatus of FIG. 34.
Figure 36:
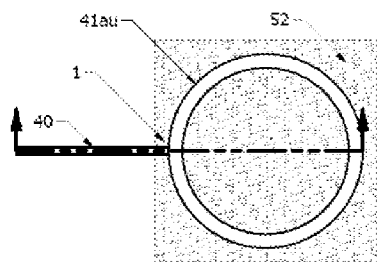
FIG. 36 is a top view illustration of an embodiment of a sterile site apparatus before it creates a planar fluid barrier over the sterile site.
Figure 38:
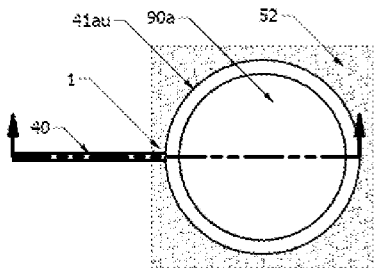
FIG. 38 is a top view illustration of the sterile site apparatus after it creates a planar fluid barrier over the sterile site.
Figure 40:
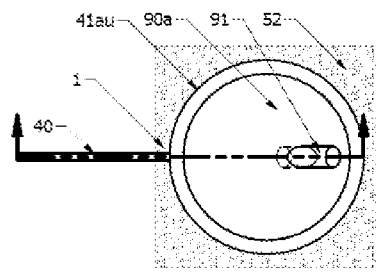
FIG. 40 is a top view illustration of the sterile site apparatus while an object passes through the planar fluid barrier.
Figure 37:
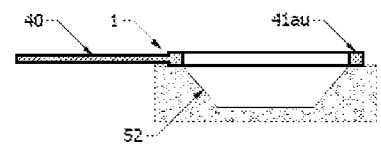
FIG. 37 is a cross-sectional view illustration of the sterile site apparatus of FIG. 36.
Figure 39:
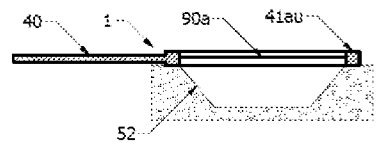
FIG. 39 is a cross-sectional view illustration of the sterile site apparatus of FIG. 38.
Figure 41:
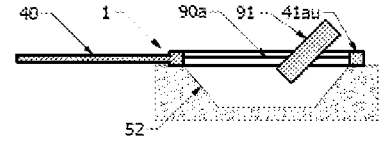
FIG. 41 is a cross-sectional view illustration of the sterile site apparatus of FIG. 40.
Figure 42:
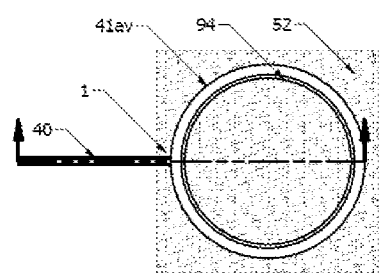
FIG. 42 is a top view illustration of an embodiment of a sterile site apparatus before it creates an extended solid barrier over the sterile site.
Figure 44:
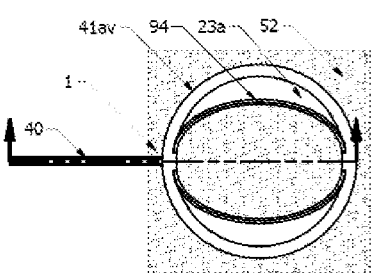
FIG. 44 is a top view illustration of the sterile site apparatus while it creates an extended solid barrier over the sterile site.
Figure 46:
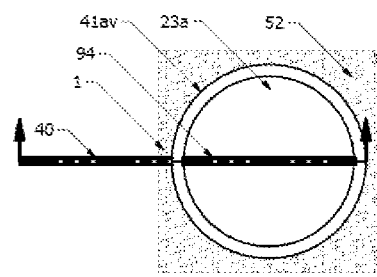
FIG. 46 is a top view illustration of the sterile site apparatus after it creates an extended solid barrier over the sterile site.
Figure 43:
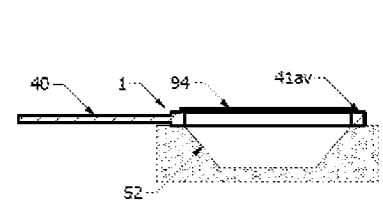
FIG. 43 is a cross-sectional view illustration of the sterile site apparatus of FIG. 42.
Figure 45:
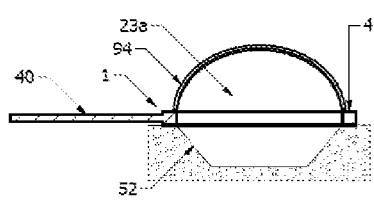
FIG. 45 is a cross-sectional view illustration of the sterile site apparatus of FIG. 44.
Figure 47:
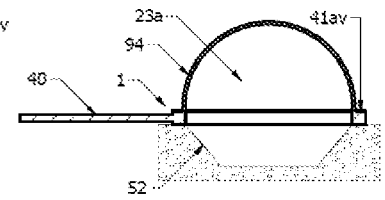
FIG. 47 is a cross-sectional view illustration of the sterile site apparatus of FIG. 46.
Figure 48:
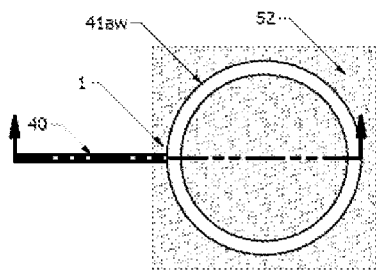
FIG. 48 is a top view illustration of an embodiment of a sterile site apparatus before it creates a planar solid barrier over the sterile site.
Figure 50:
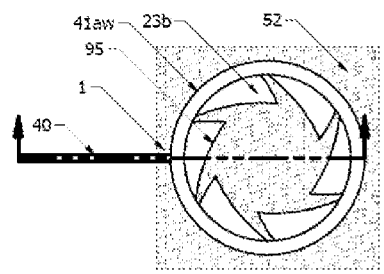
FIG. 50 is a top view illustration of the sterile site apparatus while it creates a planar solid barrier over the sterile site.
Figure 52:
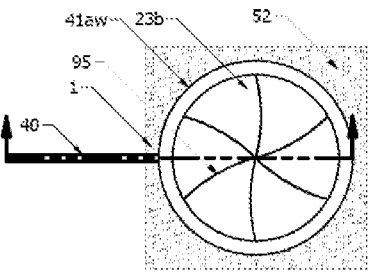
FIG. 52 is a top view illustration of the sterile site apparatus after it creates a planar solid barrier over the sterile site.
Figure 49:
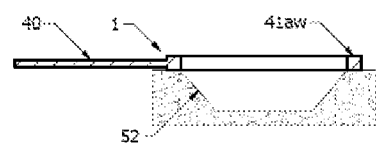
FIG. 49 is a cross-sectional view illustration of the sterile site apparatus of FIG. 48.
Figure 51:
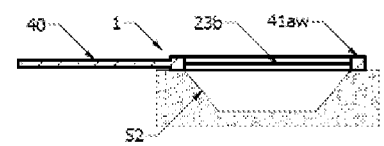
FIG. 51 is a cross-sectional view illustration of the sterile site apparatus of FIG. 50.
Figure 53:
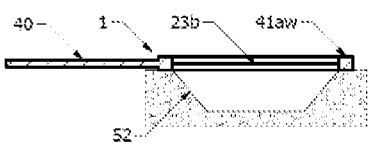
FIG. 53 is a cross-sectional view illustration of the sterile site apparatus of FIG. 52.
Figure 54:
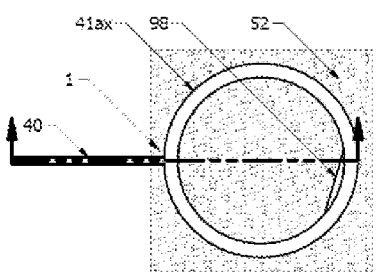
FIG. 54 is a top view illustration of an embodiment of a sterile site apparatus before it creates a thin-film solid barrier over the sterile site.
Figure 56:
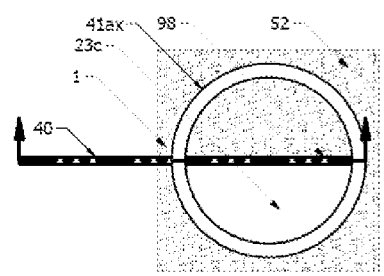
FIG. 56 is a top view illustration of the sterile site apparatus while it creates a thin-film solid barrier over the sterile site.
Figure 58:
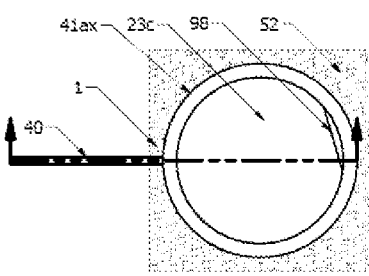
FIG. 58 is a top view illustration of the sterile site apparatus after it creates a thin-film solid barrier over the sterile site.
Figure 55:
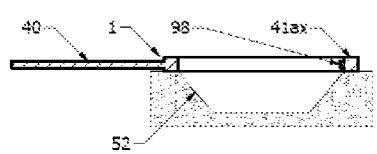
FIG. 55 is a cross-sectional view illustration of the sterile site apparatus of FIG. 54.
Figure 57:
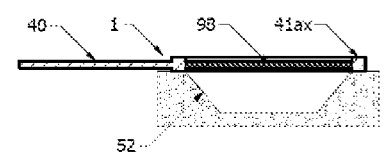
FIG. 57 is a cross-sectional view illustration of the sterile site apparatus of FIG. 56.
Figure 59:
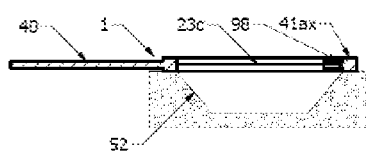
FIG. 59 is a cross-sectional view illustration of the sterile site apparatus of FIG. 58.

FIGS. 26-29 illustrate the ability of the sterile site apparatus 1 to create a coherent disinfecting fluid barrier 80, which is created by the fluid release openings 26 contained in the housing 41*c*. For the purposes of this disclosure, the term "coherent" will be used to describe the disinfecting fluid barrier 80 where the streamlines of the disinfecting fluids will be approximately convergent, parallel, and/or minimally divergent in at least one plane for desired duration or distance. The fluid release openings 26 can be oriented and arranged in ways to release their contents in any of a number of directions. The fluid release openings 26 can consist of nozzles, atomizers, nebulizers, jets, orifices, holes, slits and/or other shapes/arrangements and may release any of a number of fluids 8 (FIG. 1) in the form of a liquid, gas, mist, vapor, fog, colloid, solution, or suspension. In addition to the fluid release openings, heat, impellers, ultrasonic vibration, wicks, or other known technology can be used to combine the fluids 8. As seen in FIGS. 26 and 28, the liquid lumen 81, gas lumen 82, and suspended solids lumen 83 will distribute their respective substances throughout the housing 41*c*. As seen in FIG. 29, the substances will travel towards the liquid outlet 46, gas outlet 45, and suspended solids outlet 44 via the liquid channel 84, gas channel 85, and suspended solids channel 86, respectively. For the configuration shown in FIG. 28, the fluid release openings 26 will consist of the various outlets 44, 45, and 46. The released liquid 87, released gas 88, and released suspended solids 89 exiting their respective outlets can be mixed either external to the housing 41*c* as seen in FIG. 28 or within the housing 41*c*. The gas release openings 26 will be designed so that the released liquid 87, released gas 88, and released suspended solids 89 will form a coherent disinfecting fluid barrier 80 after being mixed. It should be noted that the sterile site apparatus 1 can consist of a number of other substances, lumens, channels, and features than those shown in FIGS. 26-29.

FIGS. 30-35 illustrate the ability of the sterile site apparatus 1 and its associated housing 41*at* to create and maintain the integrity of an extended fluid barrier 90. The extended fluid barrier 90 will extend outwards from the sterile site apparatus 1 and will create a distinct boundary between the ambient surroundings containing infectious agents and the region near the sterile site 52. While the extended fluid barrier 90 in FIGS. 32-35 is shown as a dome or arcuate shape, the extended fluid barrier 90 may form any of a number of shapes. The extended fluid barrier 90 will be composed of liquids, gases, and solids that will allow the extended fluid barrier 90 to maintain its shape while having objects 91 pass through as seen in FIGS. 34 and 35. Upon coming in contact with an object 91, the liquids, gases, and solids composing the extended fluid barrier 90 serve a variety of functions including but not limited to disinfection. Therefore, the extended fluid barrier 90 will disinfect any objects 91 and infectious agents that could come into contact with the sterile site 52. It should be noted that once the sterile site apparatus 1 creates the extended fluid barrier 90, it will be desirable to replenish the extended fluid barrier 90 with the desired liquids, gases, and solids if any of these materials are lost or depleted while the extended fluid barrier 90 is in use. It should also be noted that the extended fluid barrier 90 will have the ability to form or reform itself even when an object 91 or infectious agent is currently near or in contact with the sterile site 52. One embodiment of the extended fluid barrier 90 is formed as a bubble using a water based soap solution and a substance such as glycerin to increase the viscosity. A more robust bubble substance can be created by using polymeric soaps, block copolymers that have one hydrophobic segment attached to a hydrophilic segment as they have far better mechanical properties and are more able to heal when disrupted. Examples of these are block copolymers of either polylactic acid or polycaprolactone with polyethylene glycol. Different combinations of block molecular weights and ratios of block sizes can provide unique properties of the extended fluid barrier. Another polymer that has similar properties are block copolymers of polyethyleneglycol with polypropylene glycol. The addition of bactericidal fluids such as hypochlorous acid or hydrogen peroxide to the fluid barrier will disinfect objects that come in contact or pass through the barrier.

FIGS. 36-41 illustrate the ability of the sterile site apparatus 1 and its associated housing 41*au* to create and maintain the integrity of a planar fluid barrier 90*a*. The planar fluid barrier 90*a* will extend outwards from the sterile site apparatus 1 and will create a distinct boundary between the ambient surroundings containing infectious agents and the region near the sterile site 52. While the planar fluid barrier 90*a* in FIGS. 38-41 is shown as a planar shape, the planar fluid barrier 90*a* may form any of a number of shapes. The planar fluid barrier 90*a* will be composed of liquids, gases, and solids that will allow the planar fluid barrier 90*a* to maintain its shape while having objects 91 pass through as seen in FIGS. 40 and 41. Upon coming in contact with an object 91, the liquids, gases, and solids composing the planar fluid barrier 90*a* will serve a variety of functions including but not limited to disinfection. Therefore, the planar fluid barrier 90*a* will disinfect any objects 91 and infectious agents that could come into contact with the sterile site 52. It should be noted that once the sterile site apparatus 1 creates the planar fluid barrier 90*a*, it will be desirable to replenish the planar fluid barrier 90*a* with the desired liquids, gases, and solids if any of these materials are lost or depleted while the planar fluid barrier 90*a* is in use. It should also be noted that the planar fluid barrier 90*a* will have the ability to form or reform itself even when an object 91 or infectious agent is currently near or in contact with the sterile site 52.

FIGS. 42-47 illustrate the ability of the sterile site apparatus 1 and its associated housing 41*av* to use an extended solid barrier 23*a* to prevent infectious agents from coming into contact with the sterile site 52. The extended solid barrier 23*a* would be used when the sterile site 52 is not being accessed by the user such as when a medical instrument is no longer in contact with the sterile site 52, or it may be configured so that the leading edges 94 seal around an instrument in contact with the sterile site 52. Sensors 3 (FIG. 1) and control system 20 (FIG. 1) may be used to control the extension and retraction of solid barrier 23*a* based on a desired logic sequence. The extended solid barrier 23*a* will also be able to withdraw itself when the user wishes to access the sterile site 52. The solid barrier will be advantageous because it will prevent infectious agents contained in the ambient surroundings from coming into contact with the sterile site 52. FIGS. 44-47 also show one of the many possible ways to form the extended solid barrier 23*a* which involves rotating leading edges 94 to pull the extended solid barrier 23*a*.

FIGS. 48-53 illustrate the ability of the sterile site apparatus 1 and its associated housing 41*aw* to use a planar solid barrier 23*b* to prevent infectious agents from coming into contact with the sterile site 52. The planar solid barrier 23*b* would be used when the sterile site 52 is not being accessed by the user such as when a medical instrument is no longer in contact with the sterile site 52, or it may be configured so that the leading edges of segments 95 seal around an instrument in contact with the sterile site 52. Sensors 3 (FIG. 1) and control system 20 (FIG. 1) may be used to control the extension and retraction of solid barrier 23*b* based on a desired logic sequence. The planar solid barrier 23*b* will also be able to withdraw itself when the user wishes to access the sterile site 52. The solid barrier will be advantageous because it will prevent infectious agents contained in the ambient surroundings from coming into contact with the sterile site 52. FIGS. 50-53 also show one of the many possible ways to form the planar solid barrier 23*b* which involves drawing multiple segments 95 towards each other until they fully seal the sterile site 52 from the ambient surroundings.

FIGS. 54-59 illustrate the ability of the sterile site apparatus 1 and its associated housing 41*ax* to use a thin-film solid barrier 23*c* to prevent infectious agents from coming into contact with the sterile site 52. The thin-film solid barrier 23*c* would be used when the sterile site 52 is not being accessed by the user such as when a medical instrument is no longer in contact with the sterile site 52. Sensors 3 (FIG. 1) and control system 20 (FIG. 1) may be used to control the extension and retraction of solid barrier 23*c* based on a desired logic sequence. The thin-film solid barrier 23*c* will also be able to withdraw itself when the user wishes to access the sterile site 52. The solid barrier will be advantageous because it will prevent infectious agents contained in the ambient surroundings from coming into contact with the sterile site 52. FIGS. 56-59 also show one of the many possible ways to form the thin-film solid barrier 23*c* which involves using a rotating dispenser 98 to distribute the solid thin-film as the dispenser rotates about a fix location.

Figure 60:
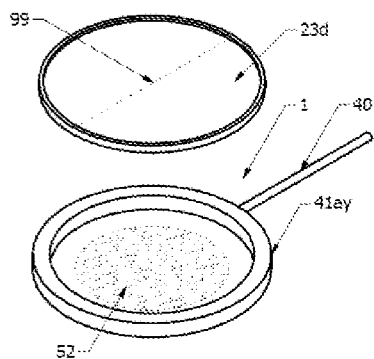
FIG. 60 is a pictorial view illustration of an embodiment of an attachable solid barrier before it is attached to the sterile site apparatus.
Figure 61:
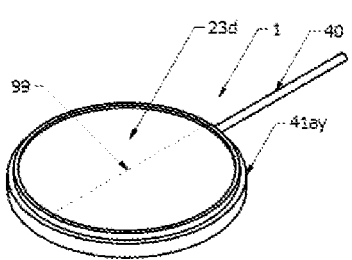
FIG. 61 is a pictorial view illustration of the attachable solid barrier after it is attached to the sterile site apparatus.
Figure 62:
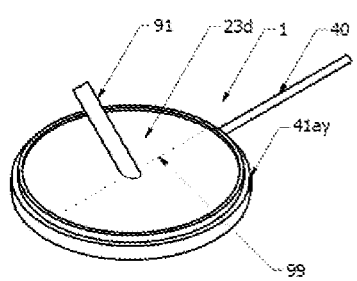
FIG. 62 is a pictorial view illustration of the sterile site apparatus while an object passes through the attachable solid barrier.
Figure 63:
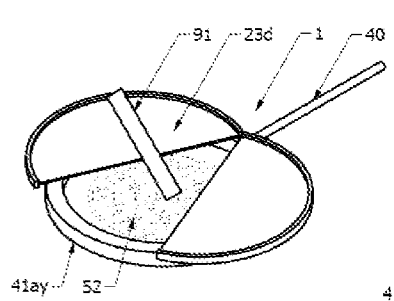
FIG. 63 is a pictorial view illustration of the sterile site apparatus after the attachable solid barrier has separated from itself and left the object undisturbed.
Figure 64:
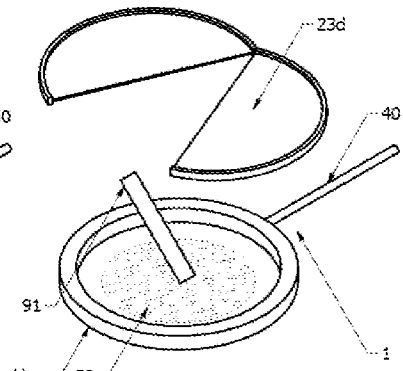
FIG. 64 is a pictorial view illustration of the sterile site apparatus after the attachable solid barrier has been removed from the sterile site apparatus and left the object undisturbed.
Figure 65:
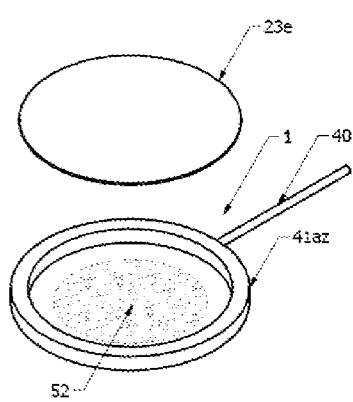
FIG. 65 is a pictorial view illustration of an embodiment of an attachable thin-film solid barrier before it is attached to the sterile site apparatus.
Figure 66:
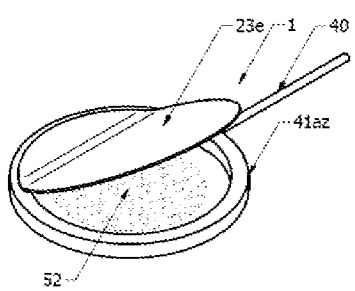
FIG. 66 is a pictorial view illustration of the attachable thin-film solid barrier after it is initially attached and begins to be applied to the sterile site apparatus.
Figure 67:
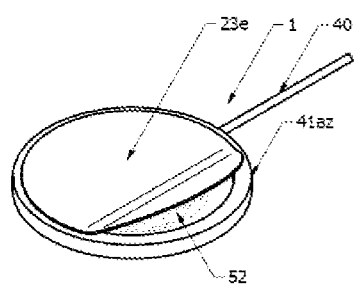
FIG. 67 is a pictorial view illustration of the attachable thin-film solid barrier as it continues to be applied to the sterile site apparatus.
Figure 68:
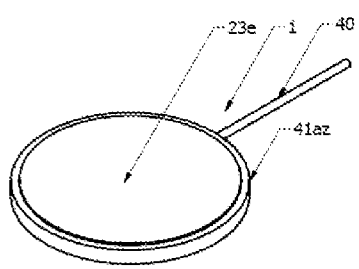
FIG. 68 is a pictorial view illustration of the attachable thin-film solid barrier after it is fully attached to the sterile site apparatus.
Figure 69:
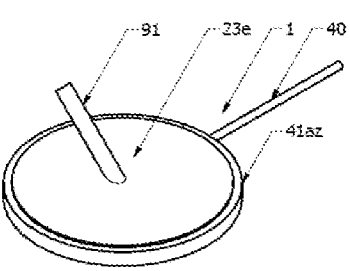
FIG. 69 is a pictorial view illustration of the sterile site apparatus as an object passes through the attachable thin-film solid barrier.

FIGS. 60-64 illustrate the ability of the sterile site apparatus 1 to use an attachable solid barrier 23*d* to prevent infectious agents from coming into contact with the sterile site 52. As seen in FIGS. 60-61, the attachable solid barrier 23*d* can originally be separate from the housing 41*ay* and then be attached to the housing 41*ay* using a variety of known technologies including but not limited to adhesives, magnets, clamps, and snap fittings. As seen in FIG. 62, once the attachable solid barrier 23*d* is secured to the housing 41*ay*, objects 91 such as medical instruments will still be able to access the sterile site 52 by passing through the attachable solid barrier 23*d*. The portion of the attachable solid barrier 23*d* that objects 91 can pass through can use a variety of known technologies including but not limited to a slit or permeable membrane to allow passage of an object 91 while preventing infectious agents in the ambient surroundings from coming into contact with the sterile site 52. As seen in FIGS. 63-64, the attachable solid barrier 23*d* will have the ability to be removed from the housing 41*ay* without disturbing the positioning of an object 91 that is currently near or in contact with the sterile site 52. FIGS. 63-64 show a possible method for removing the attachable solid barrier 23*d*, which entails separating the attachable solid barrier 23*d* along a perforation 99 and lifting the attachable solid barrier 23*d* off of the housing 41*ay*. It should be noted that the attachable solid barrier 23*d* will still prevent infectious agents from coming into contact with the sterile site 52 if an object 91 is passed into and then out of the attachable solid barrier 23*d*.

FIGS. 65-69 illustrate the ability of the sterile site apparatus 1 to use an attachable thin-film solid barrier 23*e* to prevent infectious agents from coming into contact with the sterile site 52. As seen in FIGS. 65-68, the attachable thin-film solid barrier 23*e* can originally be separate from the housing 41*az* and then by attached to the housing 41*az* using a variety of known technologies including but not limited to adhesives, magnets, clamps, and electrostatic mechanisms. Similar to the attachable solid barrier 23*d* (FIGS. 60-64), the attachable thin-film solid barrier 23*e* can have an object 91 inserted through the solid barrier while still preventing the infectious agents from coming into contact with the sterile site 52. The attachable thin-film solid barrier 23*e* can be made from variety of known materials including but not limited to a flexible polymer, tyvek (DuPont), and rubber. It should be noted that the attachable thin-film solid barrier 23*e* will still prevent infectious agents from coming into contact with the sterile site 52 if an object 91 is passed into and then out of the attachable thin-film solid barrier 23*e*.

Figure 70:
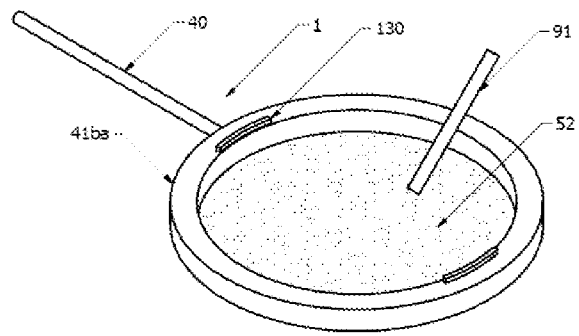
FIG. 70 is a pictorial view illustration of an embodiment of a sterile site apparatus before the opening/closing feature is used.
Figure 71:
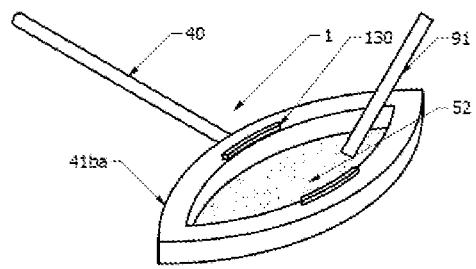
FIG. 71 is a pictorial view illustration of the sterile site apparatus while the opening/closing feature is used to reduce the size of the opening leading to the sterile site and seal around an object in contact with the sterile site.
Figure 72:
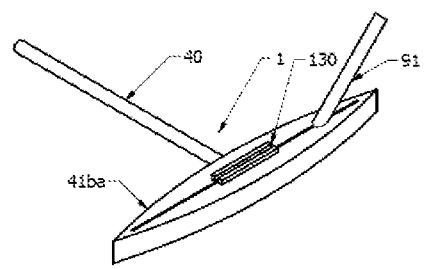
FIG. 72 is a pictorial view illustration of the sterile site apparatus after the opening/closing feature is used to reduce the size of the opening leading to the sterile site and seal around an object in contact with the sterile site.

FIGS. 70-72 illustrate the ability of the sterile site apparatus 1 and its associated housing 41*ba* to change its shape in order to reduce the size of the sterile site 52 and thereby reduce the possibility of infectious agents contained in the ambient surroundings from coming into contact with the sterile site 52. FIGS. 70-72 show the sterile site apparatus 1 and its associated housing 41*ba* changing its shape to successively reduce to the size of the sterile site 52 and create a seal around an object 91 that is in contact with the sterile site 52. The opening/closing feature 130 can act to change the shape of the sterile site apparatus 1 and its associated housing 41*ba* and to maintain that shape. The housing 41*ba* can be constructed with valorous features such as hinges, or linkages, or be a flexible material that may either be elastic or malleable depending on if the housing is to stay in a position or elastically open or close. The housing can also be configured to be soft so that it can seal around object 91, or be thin so as to allow the body tissue to seal around the object 91. The opening/closing feature 130 can use a variety of known technologies including but not limited to pneumatics, electric actuators, forces applied by the user, snap features magnets, adhesives, and clamps to change and maintain the shape of the sterile site apparatus 1. It is conceivable that the sterile site apparatus 1 can maintain an open shape, as seen in FIG. 70, when the user needs clear access to the sterile site 52 and then change to and maintain a closed shape, as seen in FIG. 72, when the user does not need clear access to the sterile site 52. It should be noted that it is also conceivable for the sterile site apparatus 1 to maintain a closed shape, as seen in FIG. 72, and then change to and maintain an open shape, as seen in FIG. 70. Sealing the sterile site apparatus 1 around an object 91 is advantageous because it will prevent infectious agents from coming into contact with the sterile site while also maintaining the positioning of the object 91 while the user is not accessing the sterile site 52.

Figure 73:
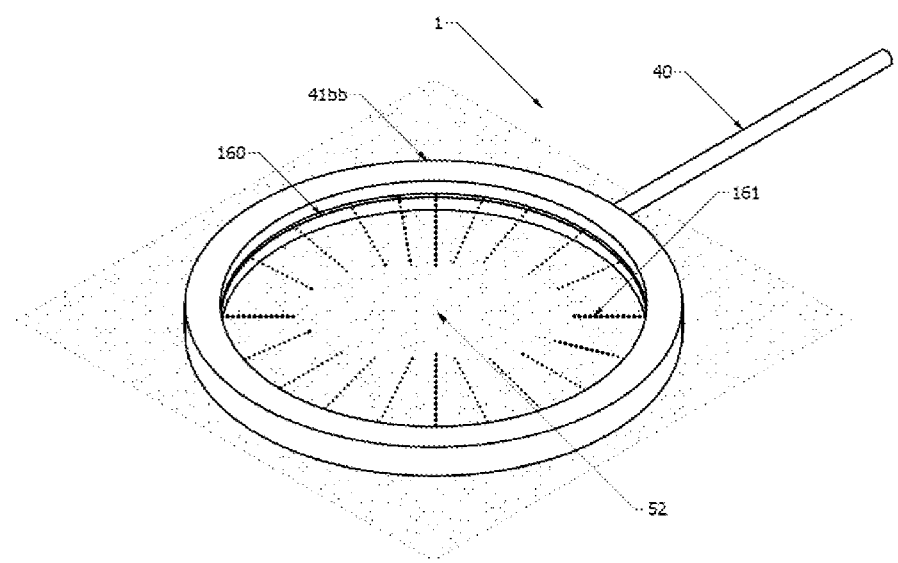
FIG. 73 is a pictorial view illustration of an embodiment of a sterile site apparatus emitting an EMR barrier.

FIG. 73 illustrates the ability of the sterile site apparatus 1 to emit the EMR barrier 161. The EMR barrier 161 will be composed of the desired wavelength(s) of EMR that disinfect infectious agents before they enter the sterile site 52. The EMR barrier 161 may have diverging beams of EMR but preferably are composed of convergent, parallel, and/or minimally divergent beams of the desired wavelength(s) of EMR. For the purposes of this disclosure, the term "coherent" will be used to describe the EMR barrier 161 where the EMR beams will be convergent, parallel, and/or minimally divergent in at least one plane. The EMR barrier 161 will be coherent in order to protect physicians from exposure to undesired levels of EMR that are emitted by the sterile site apparatus 1. For FIG. 73, the role of the desired wavelength(s) of EMR will be to disinfect infectious agents, medical instruments and other objects coming into contact with the sterile site 52. The housing 41*bb* will distribute the desired wavelength(s) of EMR to the EMR emitters 160 or the EMR emitters 160 can generate the desired wavelength(s) of EMR. EMR emitters 160 can be composed of any number of point or line sources. The EMR emitters 160 will emit the coherent EMR barrier 161 to provide a complete coverage of the area above the sterile site 52 that is encompassed by the sterile site apparatus 1. The term "barrier" is used to describe a clear, free, unimpeded, shadow-free region, surface, plane, area, or volume with the ability to pass multiple non-touching objects simultaneously through and still maintain complete contact with each object along its perimeter. As an object passes through the coherent EMR barrier 161, the object will be disinfected by the desired wavelength(s) of EMR. By disinfecting any object that could come into contact with the sterile site 52, the risk for infection will be reduced.

Figure 74:
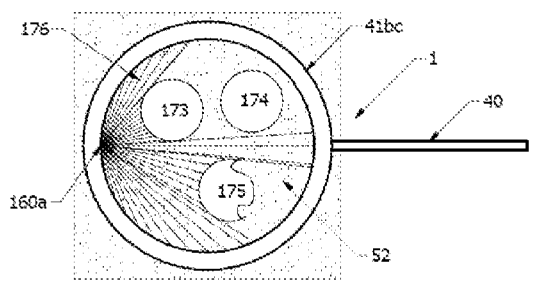
FIG. 74 is a top view illustration of the sterile site apparatus demonstrating its ability to expose a portion of an object's exterior surface to EMR even when multiple objects are simultaneously entering the EMR barrier.
Figure 75:
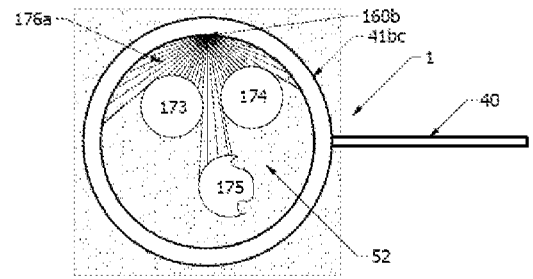
FIG. 75 is a top view illustration of the sterile site apparatus demonstrating its ability to expose a portion of an object's exterior surface to EMR even when multiple objects are simultaneously entering the EMR barrier.
Figure 76:
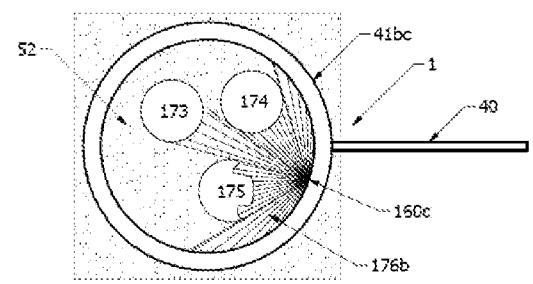
FIG. 76 is a top view illustration of the sterile site apparatus demonstrating its ability to expose a portion of an object's exterior surface to EMR even when multiple objects are simultaneously entering the EMR barrier.

FIGS. 74-76 illustrate the ability of the sterile site apparatus 1 and its associated housing 41*bc* to disinfect the entire exterior surface of an object 173 passing through the sterile site apparatus 1 even when multiple additional objects 174 and 175 are present. While many EMR emitters can be used at the same time, only single EMR emitters 160*a*, 160*b*, and 160*c* will be shown in FIGS. 74-76 in order to highlight the advantages of the sterile site apparatus 1. For FIGS. 74-76, the role of the desired wavelength(s) of EMR emitted by the EMR emitters 160*a*, 160*b*, and 160*c* will be disinfection. EMR paths 176, 176*a*, and 176*b* of the desired wavelength(s), which sum to form the coherent EMR barrier, can also be seen in FIGS. 74-76. The objects 173-175 represent objects such as infectious agents, medical devices, or a physician's hands being passed through the coherent EMR barrier and towards the sterile site 52. To highlight the advantages of the sterile site apparatus 1, object 173 will be focused on to show how the sterile site apparatus 1 is able to disinfect the exterior surface of the object 173 when multiple additional objects 174-175 are also present. As seen in FIG. 74, the EMR emitter 160*a* is able to expose the lower left portion of the object 173 to the desired wavelength(s) of EMR. As seen in FIG. 75, the EMR emitter 160*b* is able to expose the upper right portion of the object 173 to the desired wavelength(s) of EMR. As seen in FIG. 76, the EMR emitter 160*c* is able to expose the lower right portion of the object 173 to the desired wavelength(s) of EMR. Therefore, the combinations of the EMR emitters 160*a*, 160*b*, and 160*c* are able to completely disinfect the exterior surface of the object 173. This feature is advantageous because multiple objects are frequently introduced near a sterile site 52 during the course of a medical procedure. It should also be noted that the EMR emitters 160*a*, 160*b*, and 160*c*, can be replaced in FIGS. 74-76 with gas release openings 31 (FIG. 20) or fluid release openings 26 (FIG. 26) that have the same ability to completely disinfect the exterior surface of the objects 173-175 using disinfecting gases and gas mixtures, gas liquid mixtures, liquids and liquid mixtures, gas and solid mixtures, and/or liquid and solid mixtures as opposed to EMR.

FIG. 77 illustrates the ability of the sterile site apparatus 1 to create a coherent EMR barrier 161*a* out of convergent beams 184 of the desired wavelength(s) of EMR using a highly convex lens 183 and desired wavelength(s) of EMR 182 emitted from point source EMR emitters 160*d* contained within the housing 41*d*. The reflective surface 181 is advantageous because it will allow more EMR energy to actively contact objects passing through the coherent EMR barrier 161*a*. It should be noted that the highly convex lens 183 can be used in conjunction with or replaced by additional lenses and optics to produce to the coherent EMR barrier 161*a* composed of convergent beams 184 of the desired wavelength(s) of EMR. It is contemplated that the materials for the optics will be compatible with the EMR. For example, a lens can be selected from conventional lenses that are compatible with suitable levels of EMR.

Figure 78:
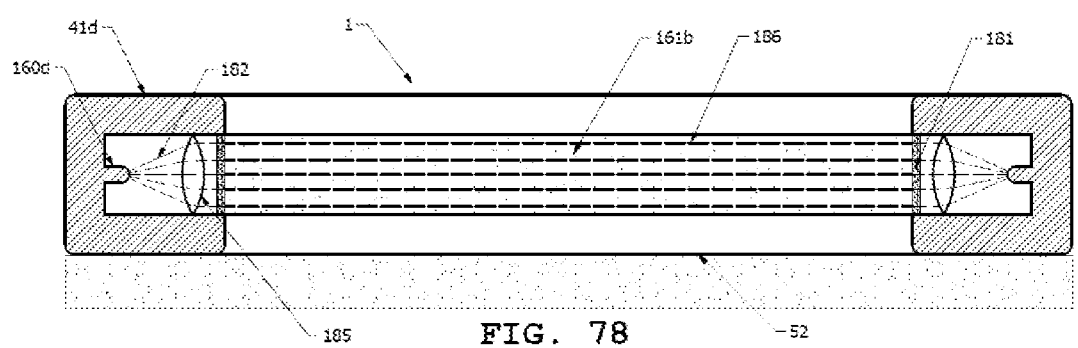
FIG. 78 is a cross-sectional view illustration of an embodiment of a sterile site apparatus to show that a coherent EMR barrier composed of parallel beams of EMR can be formed by using a lens in conjunction with EMR emitted from a point source EMR emitter.

FIG. 78 illustrates the ability of the sterile site apparatus 1 to create a coherent EMR barrier 161*b* out of parallel beams 186 of the desired wavelength(s) of EMR using a slightly convex lens 185 and desired wavelength(s) of EMR 182 emitted from point source EMR emitters 160*d* contained within the housing 41*d*. The reflective surface 181 is advantageous because it will allow more EMR energy to actively contact objects passing through the coherent EMR barrier 161*b*. It should be noted that the slightly convex lens 185 can be used in conjunction with or replaced by additional lenses and optics to produce to the coherent EMR barrier 161*b* composed of parallel beams 186 of the desired wavelength(s) of EMR.

Figure 79:
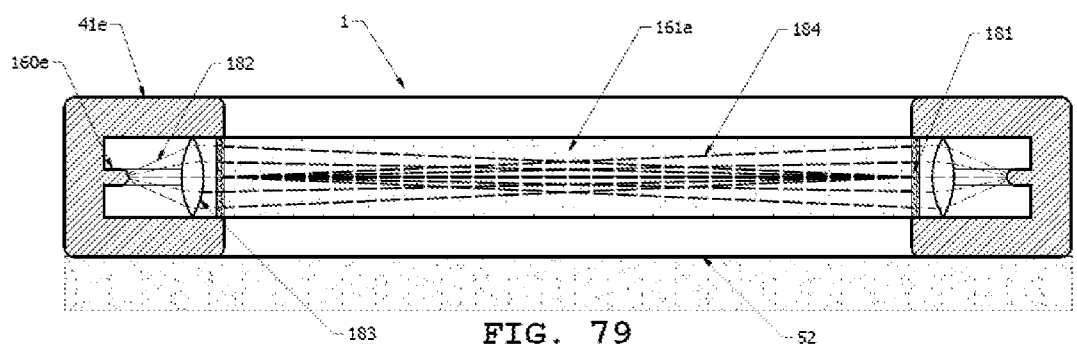
FIG. 79 is a cross-sectional view illustration of an embodiment of a sterile site apparatus to show that a coherent EMR barrier composed of convergent beams of EMR can be formed by using a lens in conjunction with EMR emitted from a line source EMR emitter.

FIG. 79 illustrates the ability of the sterile site apparatus 1 to create a coherent EMR barrier 161*a* out of convergent beams 184 of the desired wavelength(s) of EMR using a highly convex lens 183 and desired wavelength(s) of EMR 182 emitted from a line source EMR emitter 160*e* contained within the housing 41*e*. The reflective surface 181 is advantageous because it will allow more EMR energy to actively contact objects passing through the coherent EMR barrier 161*a*. It should be noted that the highly convex lens 183 can be used in conjunction with or replaced by additional lenses and optics to produce to the coherent EMR barrier 161*a* composed of convergent beams 184 of the desired wavelength(s) of EMR.

Figure 80:
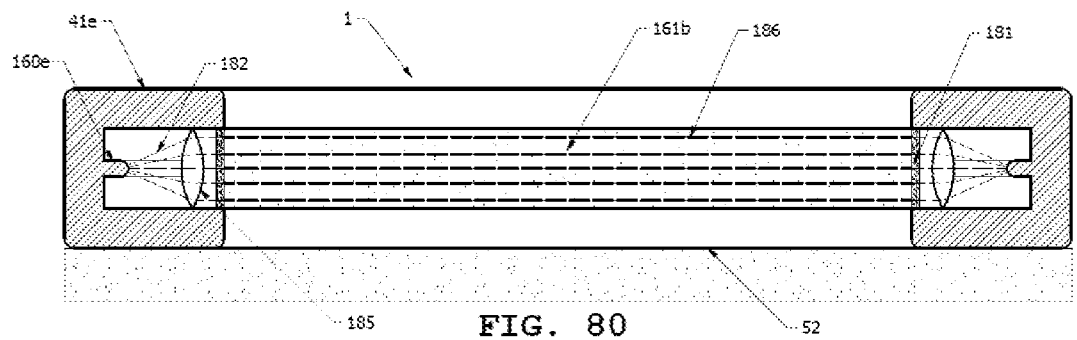
FIG. 80 is a cross-sectional view illustration of an embodiment of a sterile site apparatus to show that a coherent EMR barrier composed of parallel beams of EMR can be formed by using a lens in conjunction with EMR emitted from a line source EMR emitter.

FIG. 80 illustrates the ability of the sterile site apparatus 1 to create a coherent EMR barrier 161*b* out of parallel beams 186 of the desired wavelength(s) of EMR using a slightly convex lens 185 and desired wavelength(s) of EMR 182 emitted from a line source EMR emitter 160*e* contained within the housing 41*e*. The reflective surface 181 is advantageous because it will allow more EMR energy to actively contact objects passing through the coherent EMR barrier 161*b*. It should be noted that the slightly convex lens 185 can be used in conjunction with or replaced by additional lenses and optics to produce to the coherent EMR barrier 161*b* composed of parallel beams 186 of the desired wavelength(s) of EMR.

Figure 81:
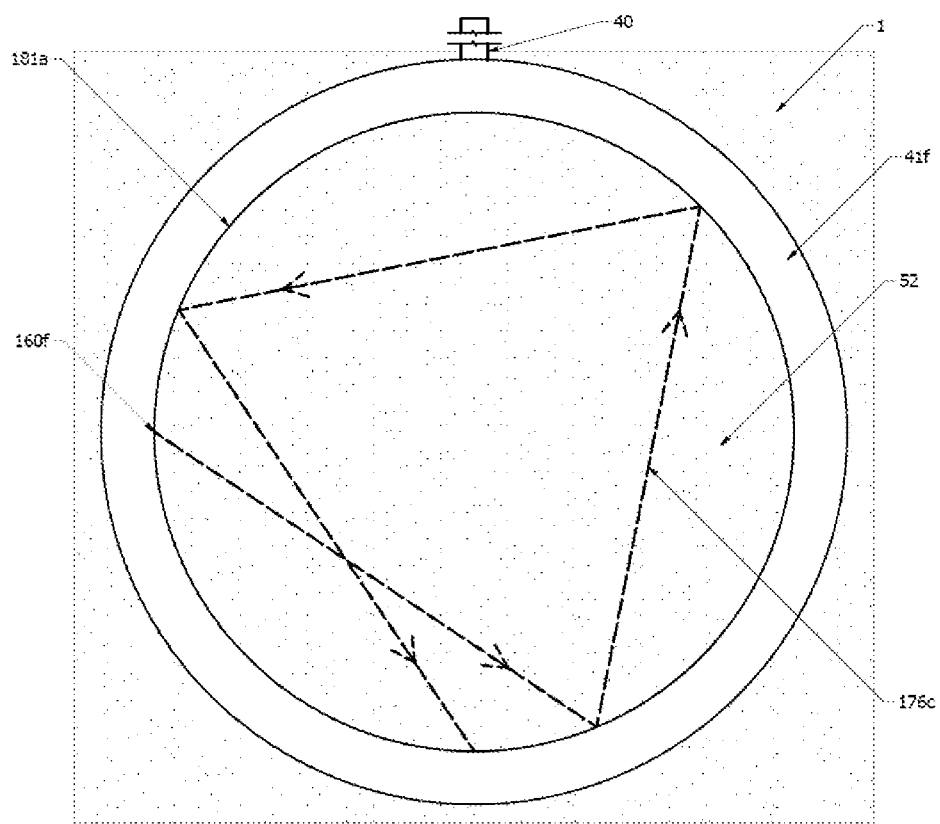
FIG. 81 is a top view illustration of an embodiment of a sterile site apparatus showing the effect of using a reflective surface to enhance the transmission of EMR.

FIG. 81 further illustrates the advantage of the sterile site apparatus 1 using a reflective surface 181*a*. The inner reflective surface 181*a* of the housing 41*f* will have characteristics to allow it to reflect certain wavelength(s) of EMR emitted from the EMR emitter 160*f*. A reflective surface 181*a* will allow the desired wavelength(s) of EMR to traverse a greater distance before dissipating. This can be seen in FIG. 81, where a beam of the desired wavelength(s) of EMR would follow the EMR path 176*c*. The reflective surface 181*a* is advantageous because it will allow more EMR energy to actively disinfect objects passing through the coherent EMR barrier. This will allow the sterile site apparatus 1 to operate with greater energy efficiency by reducing the rate of EMR dissipation in the coherent EMR barrier.

Figure 82:
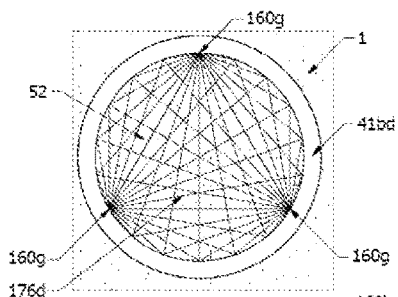
FIG. 82 is a top view illustration of an embodiment of a sterile site apparatus showing how the desired wavelength(s) of EMR can be pulsed from multiple locations at a given time interval.
Figure 83:
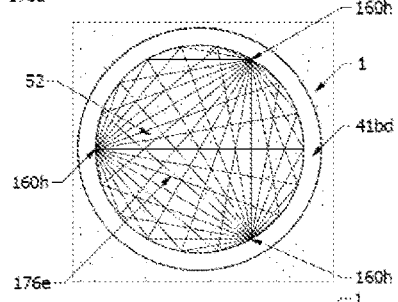
FIG. 83 is a top view illustration of the sterile site apparatus of FIG. 82 showing how the desired wavelength(s) of EMR can be pulsed from multiple different locations at a given time interval.
Figure 84:
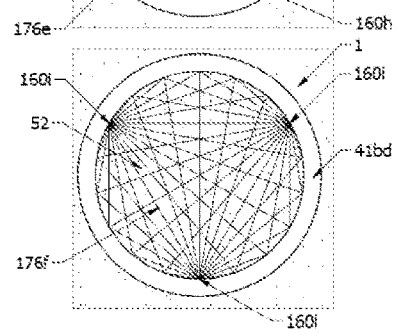
FIG. 84 is a top view illustration of the sterile site apparatus of FIG. 83 showing how the desired wavelength(s) of EMR can be pulsed from multiple locations at a given time interval.

FIGS. 82-84 illustrate the ability of the sterile site apparatus 1 and its associated housing 41*bd* to have the desired wavelength(s) of EMR pulsed from multiple EMR emitters 160*g*, 160*h*, and 160*i* at different time intervals. FIGS. 82-84 show the progression of EMR emitters being activated at successive time intervals. It also shows representations of the EMR paths 176*d*, 176*e*, and 176*f* taken by the desired wavelength(s) of EMR. Initially, the EMR emitters 160g emit EMR, which follows the EMR paths 176d. This is followed by the EMR emitters 160h emitting EMR, which travels the EMR paths 176e. Finally, the EMR emitters 160i emit EMR, which follows the EMR paths 176f. The intensity and wavelength(s) of the EMR composing the pulses will provide sufficient power to disinfect any infectious agent or object that could come into contact with the sterile site 52. Using pulsed EMR is advantageous over using constantly emitted EMR because the pulsed EMR will be more energy efficient and prolong the service life of the sterile site apparatus 1.

Figure 85:
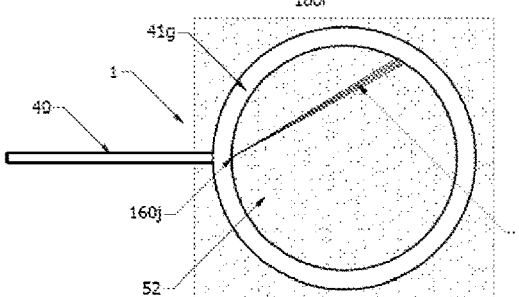
FIG. 85 is a top view illustration of an embodiment of a sterile site apparatus showing how an EMR emitter can create a sweeping motion with the desired wavelength(s) of EMR.
Figure 86:
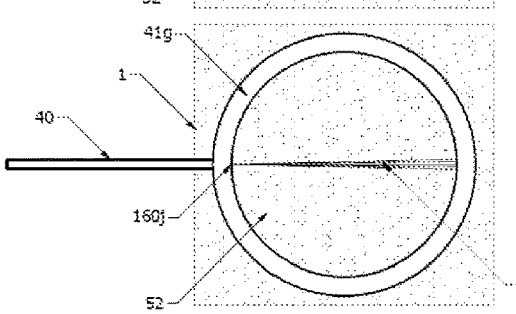
FIG. 86 is a top view illustration of the sterile site apparatus of FIG. 85 showing how an EMR emitter can create a sweeping motion with the desired wavelength(s) of EMR.
Figure 87:
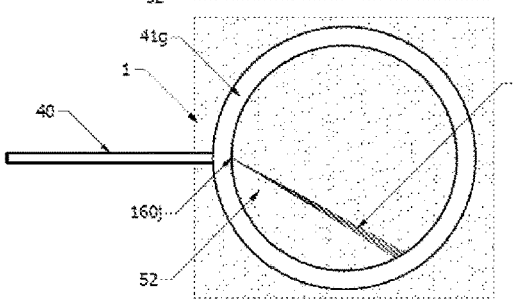
FIG. 87 is a top view illustration of the sterile site apparatus of FIG. 86 showing how an EMR emitter can create a sweeping motion with the desired wavelength(s) of EMR.

FIGS. 85-87 illustrate the ability of the sterile site apparatus 1 to use the EMR emitter 160j to emit the divergent beams 231 of EMR in various directions at successive time intervals, which results in a sweeping motion. While minimally divergent beams 231 of EMR are shown, other types of beams can be used including but not limited to convergent beams and parallel beams. A single of multiple EMR emitters 160j may be used. The sterile site apparatus 1 and its EMR emitter 160j will be able to direct the minimally divergent beams 231 in a way to provide disinfection for a portion of the region where an infectious agent or object can come into contact with the sterile site 52. Allowing a beam of the desired wavelength(s) of EMR to be directed in various directions is advantageous because it will provide any given EMR emitter 160j the ability to disinfect a larger portion of the region where an infectious agent or object can come into contact with the sterile site 52. The minimally divergent beams 231 can sweep the area encompassed by the housing 41g by rotating, oscillating, or vibrating the source, a lens or reflective surface, any other known technologies or technologies determined in the future.

Figure 88:
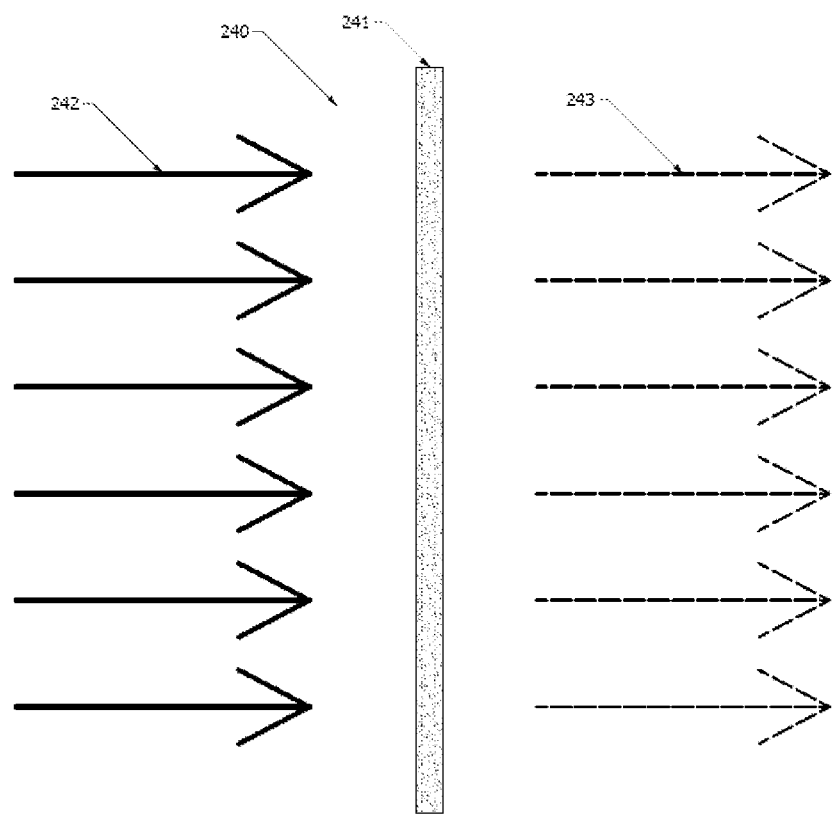
FIG. 88 is an illustration of how an EMR filter can be used to yield only the desired wavelength(s) of EMR.

FIG. 88 illustrates the function of the EMR filtration unit 240, which will be used with the sterile site apparatus. The EMR filter 241 will function by filtering the incoming broad spectrum EMR 242 to yield the filtered EMR 243. The filtered EMR 243 can then be used for a variety of purposes. Because the EMR filter 241 can only reduce the intensity of the wavelengths contained in the broad spectrum EMR 242, the intensity of the wavelengths contained in the broad spectrum EMR 242 must be greater than or equal to the intensity of the desired wavelengths of the filtered EMR 243.

Figure 89:
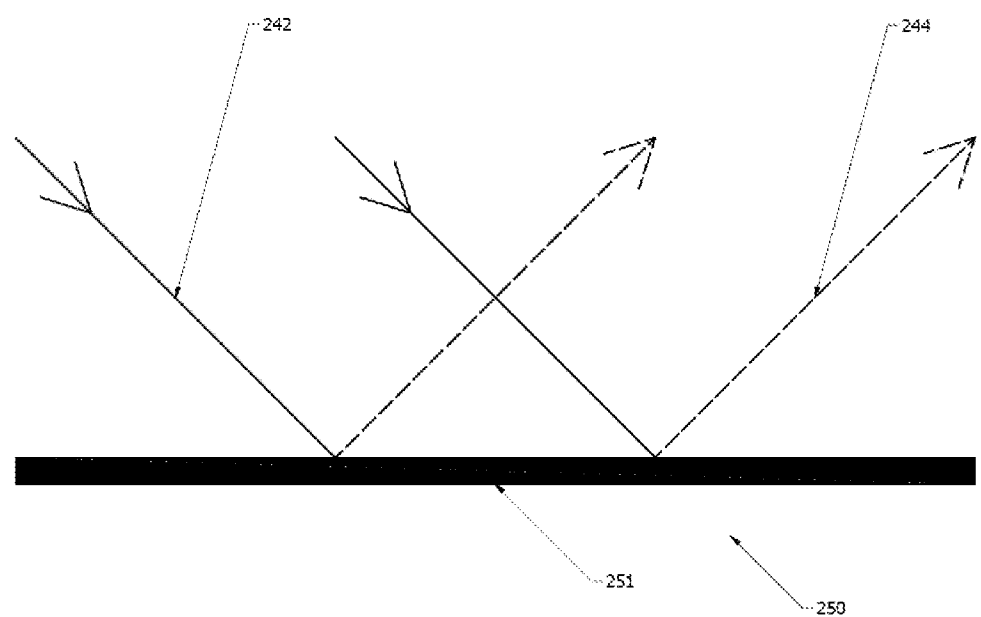
FIG. 89 is an illustration of how an EMR reflector can be used to yield only the desired wavelength(s) of EMR.

FIG. 89 illustrates the function of the EMR reflection unit 250, which will be used with the sterile site apparatus. The EMR reflector 251 will function by reflecting the incoming broad spectrum EMR 242 to yield the reflected EMR 244. The reflected EMR 244 can then be used for a variety of purposes. Because the EMR reflector 251 can only reduce the intensity of wavelengths contained in the broad spectrum EMR 242, the intensity of the wavelengths contained in the broad spectrum EMR 242 must be greater than or equal to the intensity of the desired wavelengths of the reflected EMR 244. It should be noted that the EMR reflection unit 250 can be used by the reflective surface (FIGS. 77-81).

Figure 90:
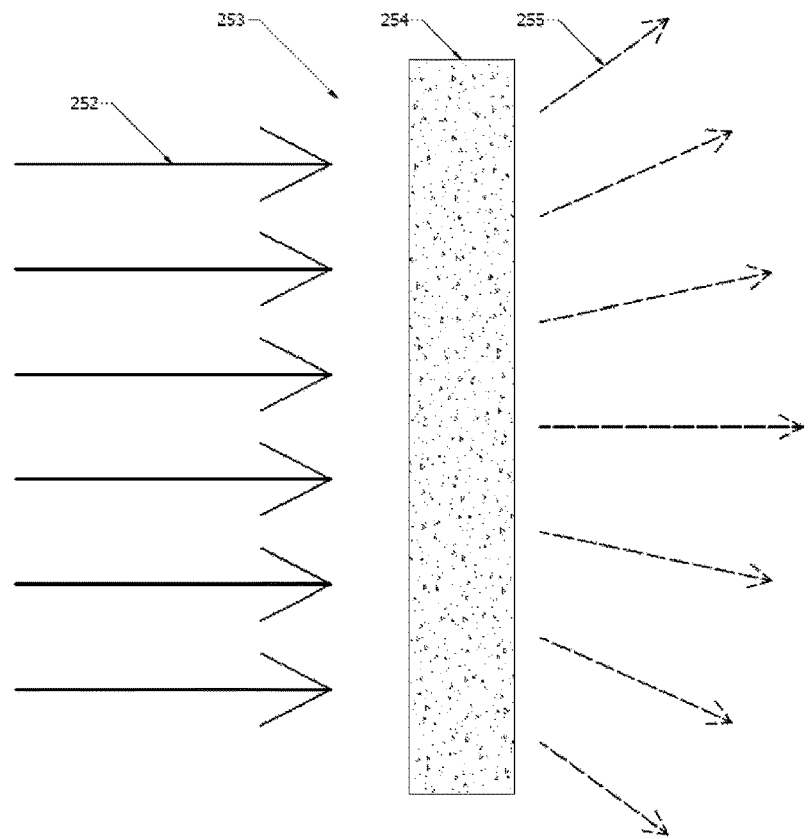
FIG. 90 is an illustration of how an emission material can be used to emit the desired wavelength(s) of EMR.

FIG. 90 illustrates the function of the EMR emission unit 253, which will be used with the sterile site apparatus 1 (FIG. 1). The emission material 254 will function by emitting the desired wavelength(s) of EMR 255 after the emission material 254 is acted upon by an input 252. The desired wavelength(s) of EMR 255 can have a variety of applications, which are further discussed throughout this document and include but are not limited to disinfection, illumination, and ozone gas generation. The nature of the input 252 can include but is not limited to mechanical, magnetic, electrostatic, electrical, EMR, thermal, and chemical stimuli. It should be noted that the emission material 254 can consist of multiple combined materials or a single material. If multiple materials are used, the ways they can be combined include but is not limited to coating, doping and mixing.

Another example of how the EMR emission unit 253 can operate is as a scintillator whereby the emission material 254 is a scintillating material that luminesces when excited by input 252 which could be in the form of ionizing radiation emitted by a fluoroscope. This is beneficial in alerting the user of ionizing radiation in or near the sterile site 52 (FIG. 1) which could be harmful to the user, specifically the user's hands which are typically unprotected from direct exposure to the radiation beam.

Figure 91:
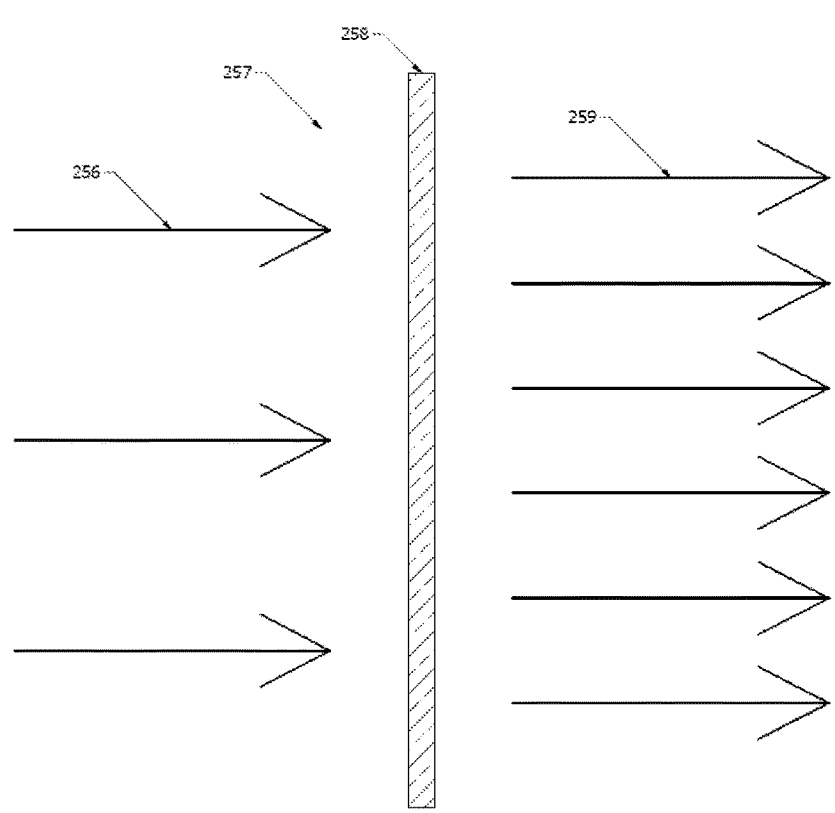
FIG. 91 is an illustration of how an EMR amplifier can be used to amplify the desired wavelength(s) of EMR.

FIG. 91 illustrates the function of the EMR amplification unit 257, which will be used with the sterile site apparatus 1 (FIG. 1). The EMR amplifier 258 will function by emitting the amplified EMR 259 after the EMR amplifier 258 is acted upon by the incoming EMR 256. It should be noted that the wavelength of the incoming EMR 256 and the wavelength of the amplified EMR 259 will be the same. However, the energy of the amplified EMR 259 will be greater than the energy of the incoming EMR 256.

Figure 92:
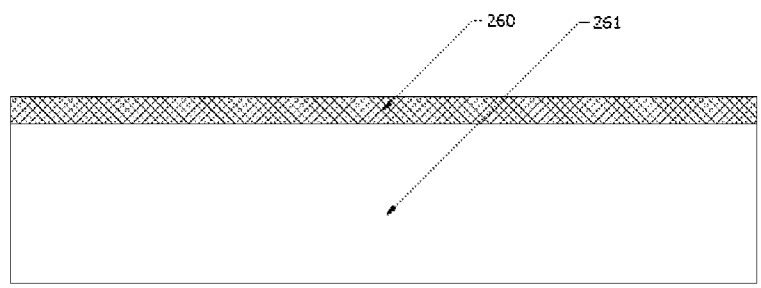
FIG. 92 is an illustration of how a coating can be used on the surface of an object.

FIG. 92 illustrates the use of a coating 260 on the surface of an object 261. The coating 260 can serve a variety of functions including but not limited to antibacterial purposes, antimicrobial purposes, antifungal purposes, antiviral purposes, producing thermal energy, conducting thermal energy, producing EMR, and adhesion. The coating 260 can be used on any number of surfaces on any part or feature of the sterile site apparatus. Coatings and fillers can be used with the sterile site apparatus and its housing to impart various features that improve the sterile site apparatus' function. Antimicrobial or antibacterial coatings and fillers will prevent the adherence, growth, and propagation of infection agents on the housing and other components of the sterile site apparatus. Antibiotics, antivirals, antifungals, and antiparasitics are commonly used. Organic acids such as lactic acid, citric acid, and acetic acid, and their salts have been used effectively. Essential oils such as bay, cinnamon, clove and thyme have been found to be inhibitive to bacterial growth. Heavy metal cations such as colloidal silver or copper alloys have substantial antimicrobial properties and are widely used on medical devices to prevent biofilm formation. Other hydrophobic coatings such as silicone oil and hydrophilic coatings can also prevent bacterial adherence. Thermally conductive coatings and fillers are used to transfer heat and cooling throughout a material that has poorer thermal conductance. Ceramic and chemical compound fillers such as alumina, boron nitride, iron-oxide, beryllium oxide, aluminum nitride, aluminum oxide, zinc oxide, silicon dioxide, or metal powders such as aluminum, copper, and silver, or liquid metal alloys such as gallium, or allotropes of carbon such as diamond, graphite, carbon fiber, fullerenes, and graphene can be used in greases, plastics, elastomers and rubbers to improve the thermal conductivity.

Figure 93:
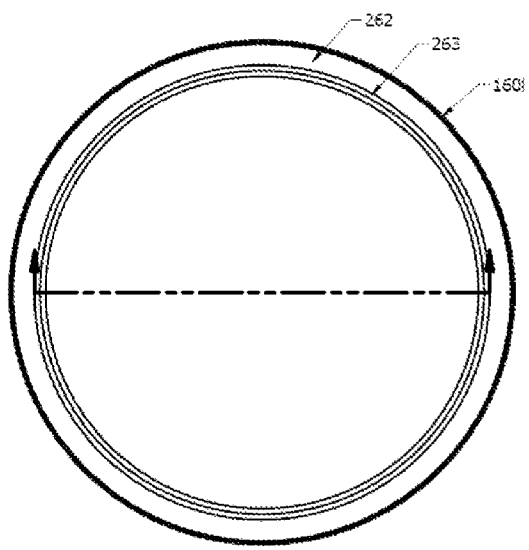
FIG. 93 is a top view illustration of an embodiment of a line source toroid convex lens apparatus, which uses a line source EMR emitter and a toroid convex lens to create an EMR barrier.
Figure 94:
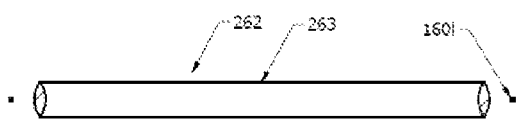
FIG. 94 is a cross-sectional view illustration of the line source toroid convex lens apparatus of FIG. 93.

FIGS. 93-94 illustrate the ability for the line source toroid convex lens apparatus 262, which is contained in the sterile site apparatus, to use a toroid convex lens 263 and a line source EMR emitter 160l to produce a coherent EMR barrier. The cross-sectional profile of the lens as seen in FIG. 94 will determine whether parallel, convergent, or minimally divergent beams of EMR are produced. It should be noted that the toroid convex lens 263 can be used in conjunction with a variety of additional lenses and optics to produce a coherent EMR barrier.

Figure 95:
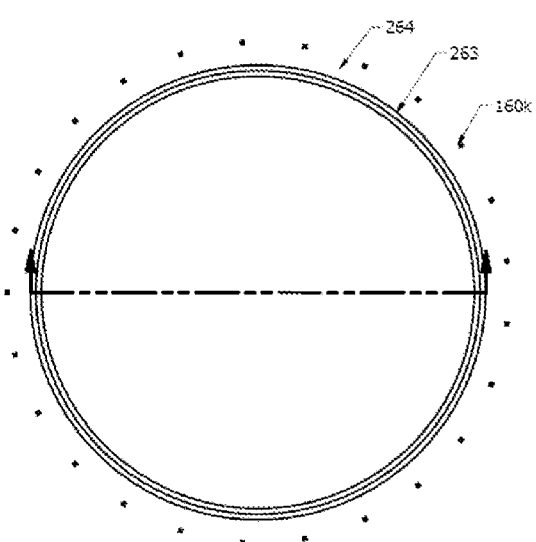
FIG. 95 is a top view illustration of an embodiment of a point source toroid convex lens apparatus, which uses point source EMR emitters and a toroid convex lens to create an EMR barrier.
Figure 96:
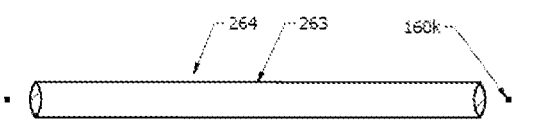
FIG. 96 is a cross-sectional view illustration of the point source toroid convex lens apparatus of FIG. 95.

FIGS. 95-96 illustrate the ability for the point source toroid convex lens apparatus 264, which is contained in the sterile site apparatus, to use a toroid convex lens 263 and point source EMR emitters 160k to produce a coherent EMR barrier. The cross-sectional profile of the lens as seen in FIG. 96 will determine whether parallel, convergent, or minimally divergent beams of EMR are produced. It should be noted that the toroid convex lens 263 can be used in conjunction with a variety of additional lenses and optics to produce a coherent EMR barrier.

Figure 97:
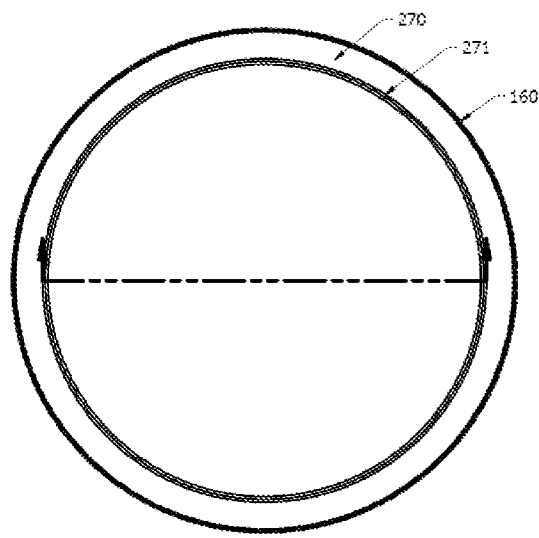
FIG. 97 is a top view illustration of an embodiment of a line source toroid meniscus lens apparatus, which uses a line source EMR emitter and a toroid meniscus lens to create an EMR barrier.
Figure 98:
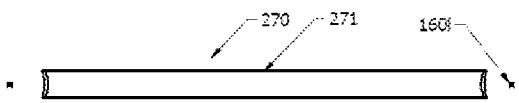
FIG. 98 is a cross-sectional view illustration of the line source toroid meniscus lens apparatus of FIG. 97.

FIGS. 97-98 illustrate the ability for the line source toroid meniscus lens apparatus 270, which is contained in the sterile site apparatus, to use a toroid meniscus lens 271 and a line source EMR emitter 160l to produce a coherent EMR barrier. The cross-sectional profile of the lens as seen in FIG. 98 will determine whether parallel, convergent, or minimally divergent beams of EMR are produced. It should be noted that the toroid meniscus lens 271 can be used in conjunction with a variety of additional lenses and optics to produce a coherent EMR barrier.

Figure 99:
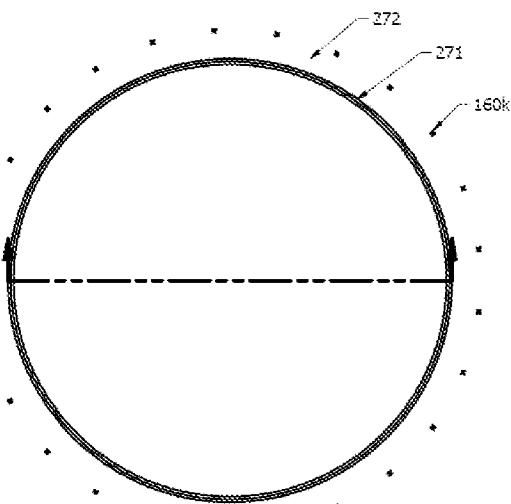
FIG. 99 is a top view illustration of an embodiment of a point source toroid meniscus lens apparatus, which uses point source EMR emitters and a toroid meniscus lens to create an EMR barrier.
Figure 100:
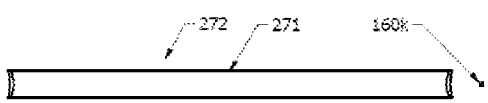
FIG. 100 is a cross-sectional view illustration of the point source toroid meniscus lens apparatus of FIG. 99.

FIGS. 99-100 illustrate the ability for the point source toroid meniscus lens apparatus 272, which is contained in the sterile site apparatus, to use a toroid meniscus lens 271 and point source EMR emitters 160k to produce a coherent EMR barrier. The cross-sectional profile of the lens as seen in FIG. 100 will determine whether parallel, convergent, or minimally divergent beams of EMR are produced. It should be noted that the toroid meniscus lens 271 can be used in conjunction with a variety of additional lenses and optics to produce a coherent EMR barrier.

Figure 101:
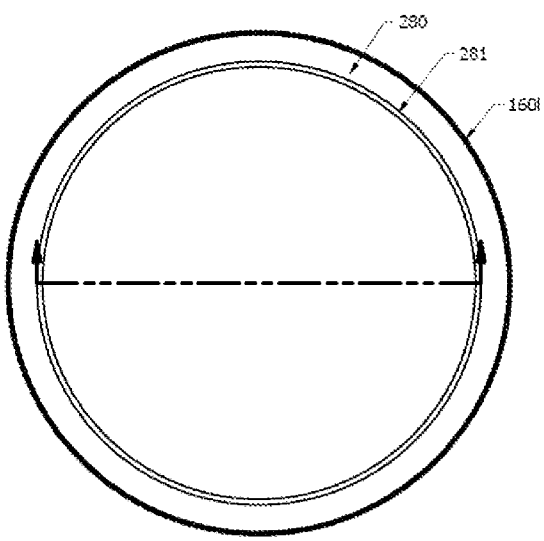
FIG. 101 is a top view illustration of an embodiment of a line source toroid plano-convex lens apparatus, which uses a line source EMR emitter and a toroid plano-convex lens to create an EMR barrier.
Figure 102:
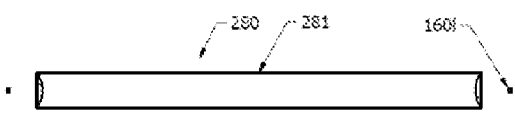
FIG. 102 is a cross-sectional view illustration of the line source toroid plano-convex lens apparatus of FIG. 101.

FIGS. 101-102 illustrate the ability for the line source toroid plano-convex lens apparatus 280, which is contained in the sterile site apparatus, to use a toroid plano-convex lens 281 and a line source EMR emitter 160l to produce a coherent EMR barrier. The cross-sectional profile of the lens as seen in FIG. 102 will determine whether parallel, convergent, or minimally divergent beams of EMR are produced. It should be noted that the toroid plano-convex lens 281 can be used in conjunction with a variety of additional lenses and optics to produce a coherent EMR barrier.

Figure 103:
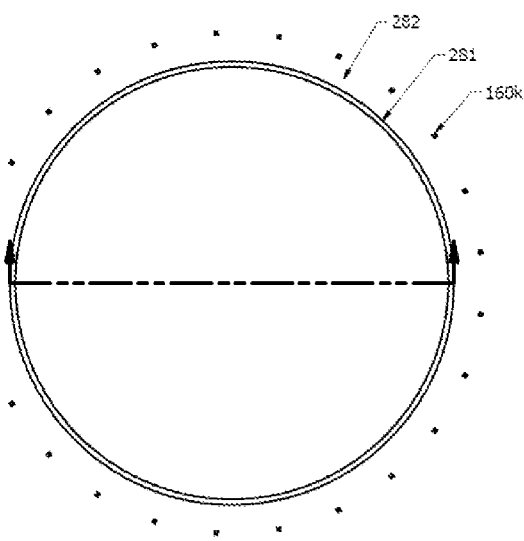
FIG. 103 is a top view illustration of an embodiment of a point source toroid plano-convex lens apparatus, which uses point source EMR emitters and a plano-toroid convex lens to create an EMR barrier.
Figure 104:
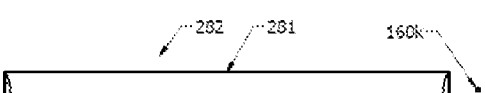
FIG. 104 is a cross-sectional view illustration of the point source toroid plano-convex lens apparatus of FIG. 103.

FIGS. 103-104 illustrate the ability for the point source toroid plano-convex lens apparatus 282, which is contained in the sterile site apparatus, to use a toroid plano-convex lens 281 and point source EMR emitters 160k to produce a coherent EMR barrier. The cross-sectional profile of the lens as seen in FIG. 104 will determine whether parallel, convergent, or minimally divergent beams of EMR are produced. It should be noted that the toroid plano-convex lens 281 can be used in conjunction with a variety of additional lenses and optics to produce a coherent EMR barrier.

Figure 105:
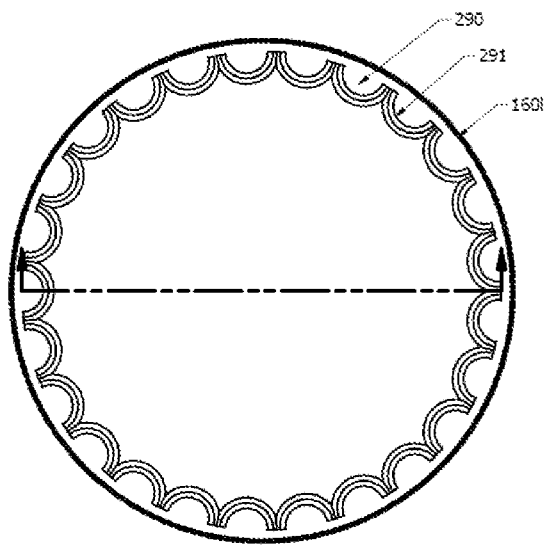
FIG. 105 is a top view illustration of an embodiment of a line source multiple partial-toroid convex lens apparatus, which uses a line source EMR emitter and multiple partial-toroid convex lens to create an EMR barrier.
Figure 106:
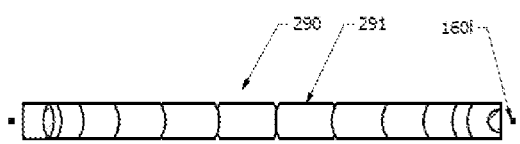
FIG. 106 is a cross-sectional view illustration of the line source multiple partial-toroid convex lens apparatus of FIG. 105.

FIGS. 105-106 illustrate the ability for the line source multiple partial-toroid convex lens apparatus 290, which is contained in the sterile site apparatus, to use a multiple partial-toroid convex lens 291 and a line source EMR emitter 160l to produce a coherent EMR barrier. The cross-sectional profile of the lens as seen in FIG. 106 will determine whether parallel, convergent, or minimally divergent beams of EMR are produced. It should be noted that the multiple partial-toroid convex lens 291 can be used in conjunction with a variety of additional lenses and optics to produce a coherent EMR barrier.

Figure 107:
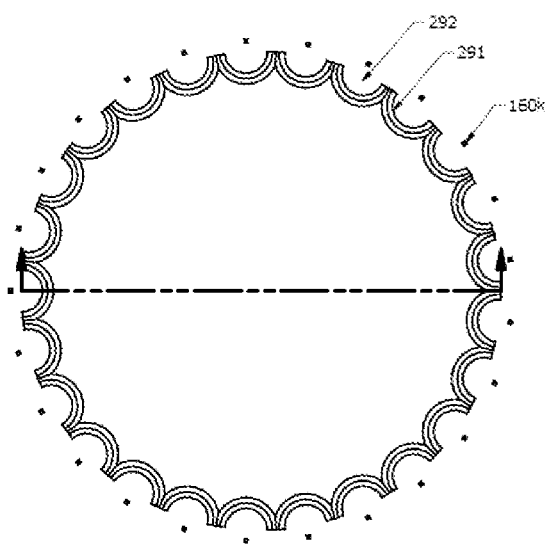
FIG. 107 is a top view illustration of an embodiment of a point source multiple partial-toroid convex lens apparatus, which uses point source EMR emitters and multiple partial-toroid convex lens to create and EMR barrier.
Figure 108:
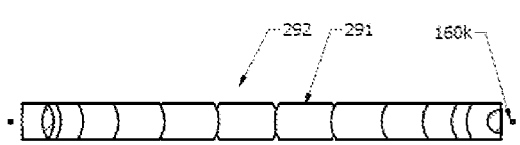
FIG. 108 is a cross-sectional view illustration of the point source multiple partial-toroid convex lens apparatus of FIG. 107.

FIGS. 107-108 illustrate the ability for the point source multiple partial-toroid convex lens apparatus 292, which is contained in the sterile site apparatus, to use a multiple partial-toroid convex lens 291 and point source EMR emitters 160k to produce a coherent EMR barrier. The cross-sectional profile of the lens as seen in FIG. 108 will determine whether parallel, convergent, or minimally divergent beams of EMR are produced. It should be noted that the multiple partial-toroid convex lens 291 can be used in conjunction with a variety of additional lenses and optics to produce a coherent EMR barrier.

Figure 109:
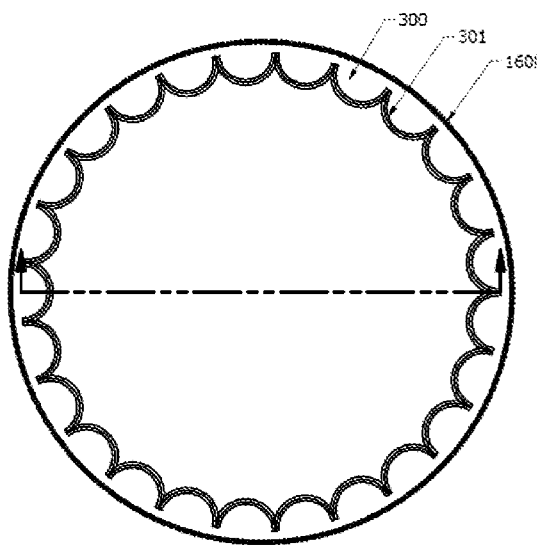
FIG. 109 is a top view illustration of an embodiment of a line source multiple partial-toroid meniscus lens apparatus, which uses a line source EMR emitter and multiple partial-toroid meniscus lens to create an EMR barrier.
Figure 110:
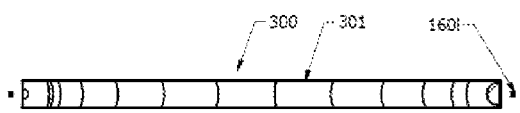
FIG. 110 is a cross-sectional view illustration of the line source multiple partial-toroid meniscus lens apparatus of FIG. 109.

FIGS. 109-110 illustrate the ability for the line source multiple partial-toroid meniscus lens apparatus 300, which is contained in the sterile site apparatus, to use a multiple partial-toroid meniscus lens 301 and a line source EMR emitter 160l to produce a coherent EMR barrier. The cross-sectional profile of the lens as seen in FIG. 110 will determine whether parallel, convergent, or minimally divergent beams of EMR are produced. It should be noted that the multiple partial-toroid meniscus lens 301 can be used in conjunction with a variety of additional lenses and optics to produce a coherent EMR barrier.

Figure 111:
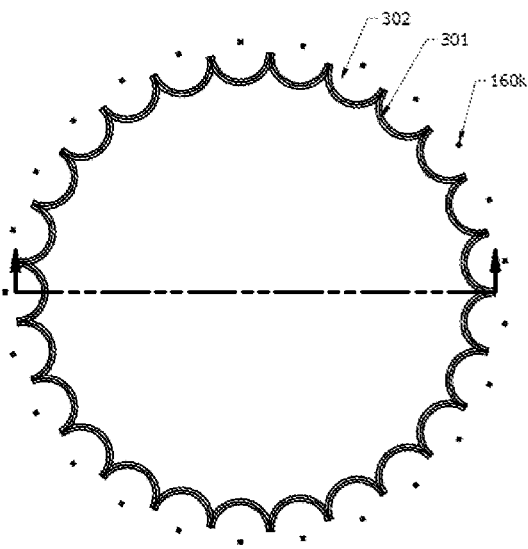
FIG. 111 is a top view illustration of an embodiment of a point source multiple partial-toroid meniscus lens apparatus, which uses point source EMR emitters and multiple partial-toroid meniscus lens to create an EMR barrier.
Figure 112:
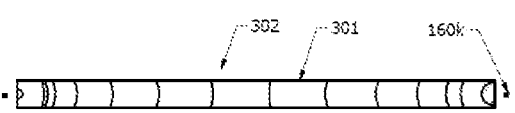
FIG. 112 is a cross-sectional view illustration of the point source multiple partial-toroid meniscus lens apparatus of FIG. 111.

FIGS. 111-112 illustrate the ability for the point source multiple partial-toroid meniscus lens apparatus 302, which is contained in the sterile site apparatus, to use a multiple partial-toroid meniscus lens 301 and point source EMR emitters 160k to produce a coherent EMR barrier. The cross-sectional profile of the lens as seen in FIG. 112 will determine whether parallel, convergent, or minimally divergent beams of EMR are produced. It should be noted that the multiple partial-toroid meniscus lens 301 can be used in conjunction with a variety of additional lenses and optics to produce a coherent EMR barrier.

FIGS. 113-114 illustrate the ability for the line source multiple partial-toroid plano-convex lens apparatus 310, which is contained in the sterile site apparatus, to use a multiple partial-toroid plano-convex lens 311 and a line source EMR emitter 160l to produce a coherent EMR barrier. The cross-sectional profile of the lens as seen in FIG. 114 will determine whether parallel, convergent, or minimally divergent beams of EMR are produced. It should be noted that the multiple partial-toroid plano-convex lens 311 can be used in conjunction with a variety of additional lenses and optics to produce a coherent EMR barrier.

FIGS. 115-116 illustrate the ability for the point source multiple partial-toroid plano-convex lens apparatus 312, which is contained in the sterile site apparatus, to use a multiple partial-toroid plano-convex lens 311 and point source EMR emitters 160k to produce a coherent EMR barrier. The cross-sectional profile of the lens as seen in FIG. 116 will determine whether parallel, convergent, or minimally divergent beams of EMR are produced. It should be noted that the multiple partial-toroid plano-convex lens 311 can be used in conjunction with a variety of additional lenses and optics to produce a coherent EMR barrier.

FIGS. 117-118 illustrate the ability of the sterile site apparatus 1 to deliver fiber optics 320 throughout the housing 41h via the supply cord 40. It should be noted that the fiber optics 320 can still be distributed throughout the sterile site apparatus 1 if the housing 41h is not present. The fiber optics 320 will carry the desired wavelength(s) of EMR, which will be generated at a source connected to or separate from the housing 41h. The fiber optics 320 will be able to efficiently carry the desired wavelength(s) of EMR without a significant decrease in power.

Figure 119:
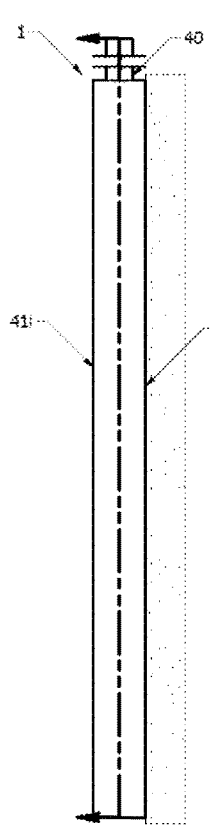
Figure 120:
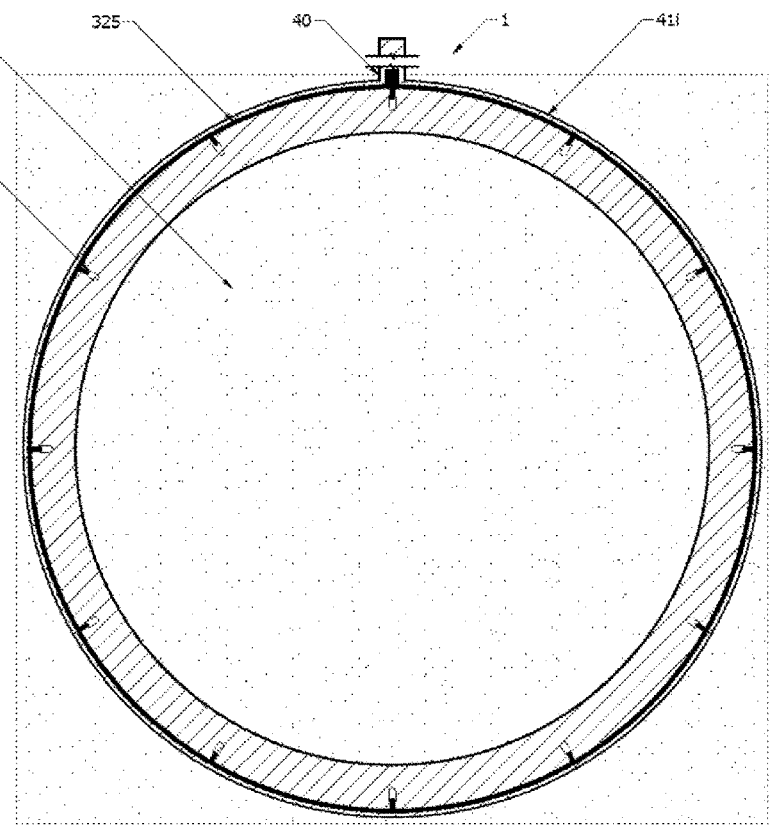

FIGS. 119-120 illustrate the ability of the sterile site apparatus 1 to deliver a power wire 325 throughout the housing 41i via the supply cord 40. The power wire 325 will power the internal EMR emitters 160m, which will generate the desired wavelength(s) of EMR. The internal EMR emitters 160m are contained within the housing 41i. However, it should be noted that other EMR emitters can be located anywhere within, attached to, or distant to the sterile site apparatus 1. The desired wavelength(s) of EMR generated by the internal EMR emitters 160m can be sent to a system of the sterile site apparatus 1, which will create an EMR barrier. The power wire 325 can also be used for a variety of additional systems and features.

Figure 121:
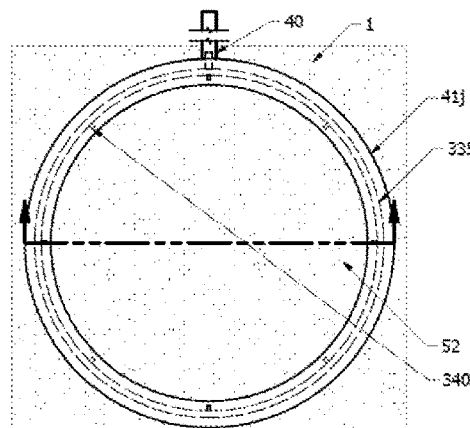
Figure 122:
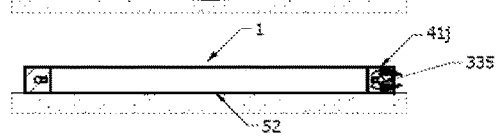
Figure 123:
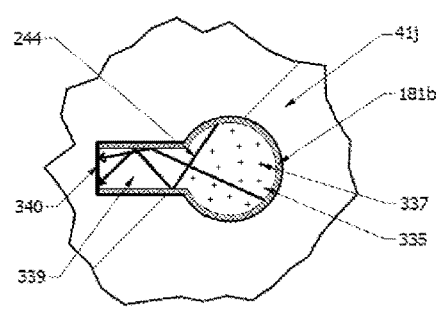
Figure 124:
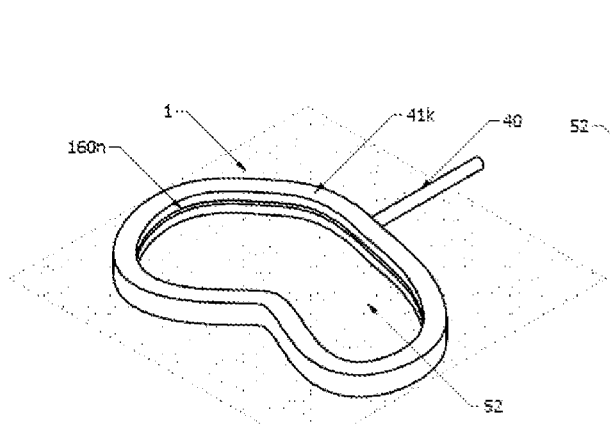
Figure 125:
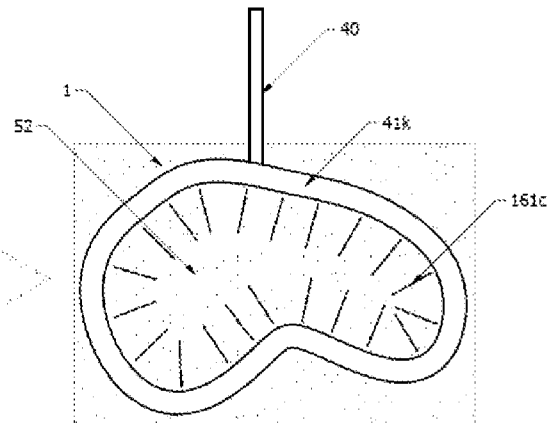
Figure 126:
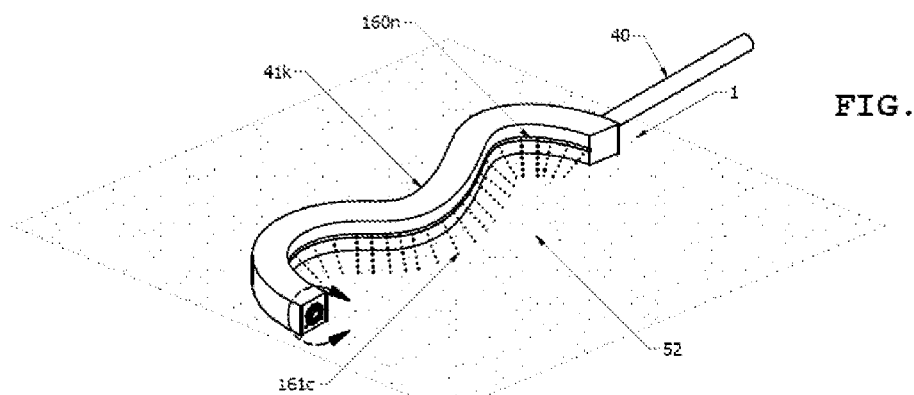

FIGS. 121-123 illustrate the ability of the sterile site apparatus 1 to have a transmission channel 335 distribute the desired wavelength(s) of EMR throughout the housing 41*j*. The desired wavelength(s) of EMR will be delivered to the transmission channel 335 via the supply cord 40 or other means. The transmission channel 335 will be composed of a transmission medium 339, which will efficiently transmit the desired wavelength(s) of EMR without a significant decrease in power, and a reflective surface 181*b*, which will reflect the desired wavelength(s) of EMR throughout the transmission medium 339. EMR will travel throughout the transmission channel 335 as peripheral EMR 337 until it is reflected towards an outlet 340. Peripheral EMR 337 that is reflected towards an outlet 340 will be designated as reflected EMR 244. The reflected EMR 244 will then be used by a system of the sterile site apparatus 1, which will create the EMR barrier with the desired wavelength(s) of EMR.

Figure 127:
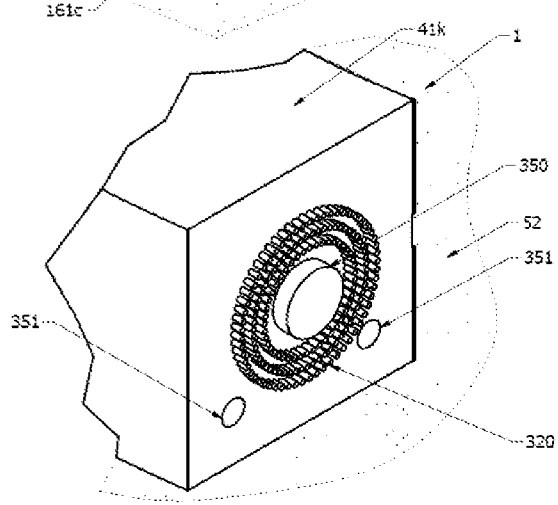

FIGS. 124-127 illustrate the ability of the sterile site apparatus 1 to have its housing 41*k* be in a non-circular and potentially non-planar configuration by being flexible and malleable. After the housing 41*k* is molded to a desired shape by the physician(s) or medical staff, the sterile site apparatus 1 will still be able to create an EMR barrier 161*c* from the EMR emitters 160*n*. This malleable feature is advantageous because it will allow a custom shape to be created for each patient to meet his or her individual needs. This will be especially useful for sterile sites 52 that have an unusual, non-uniform shape. It is also contemplated for the housing 41*k* not being continuous, fully enclosed, or connected all the way around, so that the housing 41*k* can still provide a barrier for sterile sites 52 that may already be enclosed on one or more sides by a projecting wall or other barrier. While showing several features of the housing 41*k*, FIG. 127 highlights the malleable portion 350. For this particular embodiment, the housing 41*k* will be made of a non-rigid material while the malleable portion 350 is made of a material can be molded/bent to the desired shape. The sterile site apparatus 1, housing 41*k*, and malleable portion 350 will be designed so that the EMR barrier 161*c* will not be directed in a manner that will cause an increased exposure of EMR to the patient and/or physician(s). FIG. 127 also shows the fluid and gas lumens 351, which can be used to deliver fluid and/or gas near the sterile site 52, and the fiber optics 320, which can deliver the desired wavelength(s) of EMR throughout the housing 41*k*. It should be noted that the sterile site apparatus 1 can contain additional components, systems, and features than those shown in FIGS. 124-127. It should also be noted that the housing 41*k* of the sterile site apparatus 1 can be pre-fabricated in a particular desired shape that may or may not be malleable, so it can be used as is without having to be formed by the medical staff.

Figure 128:
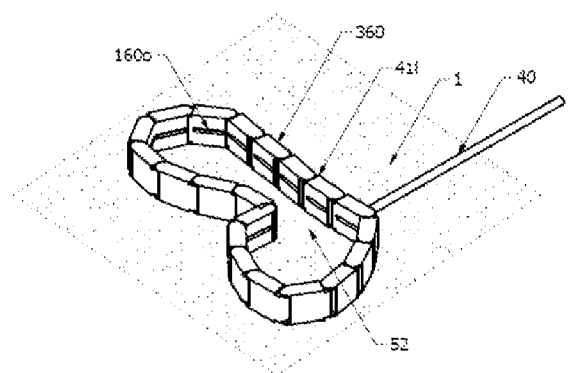
Figure 129:
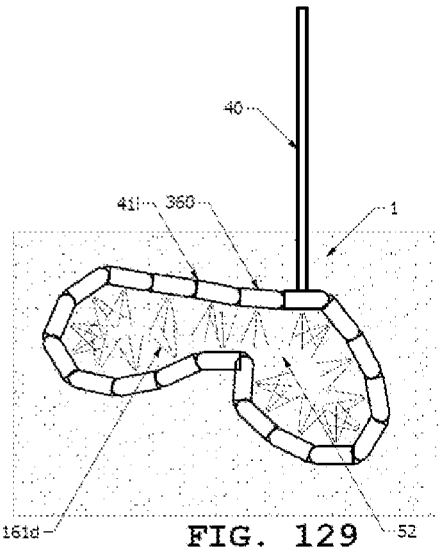

FIGS. 128-129 illustrate the ability of the sterile site apparatus 1 to be composed of multiple housing links 360, which will form the housing 41I. The housing links 360 and their method of attaching to one another will be designed to ensure that the EMR barrier 161*d* which is created by the EMR emitters 160*o*, will not be directed in a manner that will cause an increased exposure of EMR to the patient and/or physician(s). Similar to the malleable housing, the housing links 360 will allow for a custom shape of the housing 41I of the sterile site apparatus 1. The housing links 360 can be hinged in a single plane so that the housing 41I stays in a plane perpendicular to the hinged members, the housing links 360 can be hinged in alternating ninety degree planes so that the housing 41I can be angled perpendicularly out of plane, or the housing links 360 can be hinged in any plane in any order so that the housing 41I can assume any shape. The housing links 360 can be loose, a friction fit, or be detented to lock into discrete positions depending on the desired function of the housing 41I.

Figure 130:
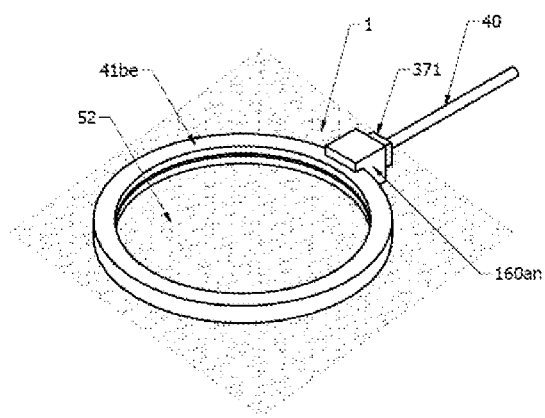

FIGS. 130-131 illustrate the ability of the sterile site apparatus 1 to consist of a housing 41*be* and a single EMR emitter 160*an*, which will be powered by the supply cord 40. Additionally, an object sensor 3*a* may be used in conjunction with the EMR emitter 160*an*. For example, the object sensor 3*s* senses an object about to enter the sterile site 52, which causes the control system 20 (FIG. 1) to turn on the EMR emitter 160*an* so that it can generate the desired wavelength(s) of EMR and send it to the housing 41*be*. The advantage of using an object sensor 3*a* for controlling the EMR emitter 160*an* is that the EMR barrier will only be on when it is needed to disinfect infectious agents before they enter the sterile site 52, thereby lowering EMR exposure to the sterile site 52 and to any persons in proximity to the sterile site 52. Locating the EMR emitter 160*an* closer to the sterile site 52 will be beneficial because the EMR power will be used efficiently. If fiber optics or other transmission means were used to bring the desired wavelength(s) of EMR from a distant EMR emitter or generator, EMR power would be dissipated. This would be detrimental because the sterile site apparatus 1 would need to draw greater power in order to emit a given level of EMR. A cooling unit 371 can also be used in conjunction with the EMR emitter 160*an* in order to prevent overheating/wear/damage. Using a cooling unit 371 will prolong the service life of the sterile site apparatus 1. The cooling unit 371 can consist of a small fan, fin arrays, pumped coolant system, or other forms of heat sinks. If solid state LED's are used to generate the EMR, then cooling unit 371 may not be needed.

FIGS. 132-133 illustrate the ability of the sterile site apparatus 1 to consist of a single EMR emitter 160*an*, which will be powered by the supply cord 40. It should be noted that this design does not utilize a housing. Additionally, an object sensor 3*a*, and a cooling unit 371 may be used in conjunction with the EMR emitter 160*an* in a similar manner to FIG. 131.

FIGS. 134-135 illustrate the ability of the sterile site apparatus 1 to consist of a housing 41*m* and a multiple EMR emitters 160*ao*, which will be powered by the supply cord 40 and secondary supply cords 40*a*. Additionally, object sensors 3*b*, cooling units 371*a* may be used in conjunction with the EMR emitters 160*ao* in a similar manner to FIG. 131.

FIGS. 136-137 illustrate the ability of the sterile site apparatus 1 to consist of a multiple EMR emitters 160*ao*, which will be powered by the supply cord 40 and secondary supply cords 40*a*. It should be noted that this design does not call for a housing. Additionally, object sensors 3*b*, and cooling units 371*a* may be used in conjunction with the EMR emitters 160*ao* in a similar manner to FIG. 131.

FIGS. 138-142 illustrate the ability for the sterile site apparatus 1 to consist of a positively charged electrode 390, housing 41*bf* and supply cord 40. FIGS. 138-142 focus on the function of the positively charged electrode 390 in the presence of falling infectious agents 391 and ionized gas containing electrons 392. The ionized gas containing electrons 392 can be created by the ionizer/ion balancer 15 of the gas handling unit 10 (FIG. 2). FIGS. 140-142 are depicting the sterile site apparatus 1 at successive time intervals. When the falling infectious agents 391 travel towards the sterile site 52, as seen in FIG. 140, the infectious agents 391 will pass through ionized gas containing electrons 392. When the falling infectious agents 391 come into contact with the electrons 392, they will become attached to each other, as seen in FIG. 141. Because of the opposite charges, the negatively charged object consisting of infectious agents 391 and electrons 392 will become attracted to the positively charged electrode 390, as seen in FIG. 142. By doing so, the infectious agents 391 will be prevented from coming into contact with the sterile site 52. Although the FIGS. 138-142 depict the positively charged electrode 390 as a separate component from the housing 41*bf*, it is also contemplated that the positively charged electrode 390 is integrated with or attached to the housing 41*bf*.

FIGS. 143-147 illustrate the ability for the sterile site apparatus 1 to consist of a negatively charged electrode 393, housing 41*bf* and supply cord 40. FIGS. 143-147 focus on the function of the negatively charged electrode 393 in the presence of falling infectious agents 391 and ionized gas containing protons 394. The ionized gas containing protons 394 can be created by the ionizer/ion balancer 15 of the gas handling unit 10 (FIG. 2). FIGS. 145-147 are depicting the sterile site apparatus 1 at successive time intervals. When the falling infectious agents 391 travel towards the sterile site 52, as seen in FIG. 145, the infectious agents 391 will pass through ionized gas containing protons 394. When the falling infectious agents 391 come into contact with the protons 394, they will become attached to each other, as seen in FIG. 146. Because of the opposite charges, the positively charged object consisting of infectious agents 391 and protons 394 will become attracted to the negatively charged electrode 393, as seen in FIG. 147. By doing so, the infectious agents 391 will be prevented from coming into contact with the sterile site 52. Although the FIGS. 143-147 depict the negatively charged electrode 393 as a separate component from the housing 41*bf*, it is also contemplated that the negatively charged electrode 393 is integrated with or attached to the housing 41*bf*.

FIGS. 148-152 illustrate the ability for the sterile site apparatus 1 to consist of a negatively charged electrode 393, housing 41*bf* and supply cord 40. FIGS. 148-152 focus on the function of the negatively charged electrode 393 in the presence of falling infectious agents 391 and ionized gas containing electrons 392. The ionized gas containing electrons 392 can be created by the ionizer/ion balancer 15 of the gas handling unit 10 (FIG. 2). FIGS. 150-152 are depicting the sterile site apparatus 1 at successive time intervals. When the falling infectious agents 391 travel towards the sterile site 52, as seen in FIG. 150, the infectious agents 391 will pass through ionized gas containing electrons 392. When the falling infectious agents 391 come into contact with the electrons 392, they will become attached to each other, as seen in FIG. 151. Because of the similar charges, the negatively charged object consisting of infectious agents 391 and electrons 392 will be repelled by the negatively charged electrode 393, as seen in FIG. 152. By doing so, the infectious agents 391 will be prevented from coming into contact with the sterile site 52. Although the FIGS. 148-152 depict the negatively charged electrode 393 as a separate component from the housing 41*bf*, it is also contemplated that the negatively charged electrode 393 is integrated with or attached to the housing 41*bf*.

FIGS. 153-157 illustrate the ability for the sterile site apparatus 1 to consist of a positively charged electrode 390, housing 41*bf* and supply cord 40. FIGS. 153-157 focus on the function of the positively charged electrode 390 in the presence of falling infectious agents 391 and ionized gas containing protons 394. The ionized gas containing protons 394 can be created by the ionizer/ion balancer 15 of the gas handling unit 10 (FIG. 2). FIGS. 155-157 are depicting the sterile site apparatus 1 at successive time intervals. When the falling infectious agents 391 travel towards the sterile site 52, as seen in FIG. 155, the infectious agents 391 will pass through ionized gas containing protons 394. When the falling infectious agents 391 come into contact with the protons 394, they will become attached to each other, as seen in FIG. 156. Because of the similar charges, the positively charged object consisting of infectious agents 391 and protons 394 will be repelled by the positively charged electrode 390, as seen in FIG. 157. By doing so, the infectious agents 391 will be prevented from coming into contact with the sterile site 52. Although the FIGS. 153-157 depict the positively charged electrode 390 as a separate component from the housing 41*bf*, it is also contemplated that the positively charged electrode 390 is integrated with or attached to the housing 41*bf*.

FIGS. 158-159 illustrate the ability for the sterile site apparatus 1 to emit the ozone-generating EMR 411, which will create an ozone-filled region 412 near the sterile site 52. The ozone-generating EMR 411 will be released by ozone-generating EMR emitters 160*q*. The ozone-generating EMR 411 will be generated within the housing 41*n* or it will be delivered via the supply cord 40. The ozone-generating EMR 411 will be emitted at the specific wavelength(s) and intensities to generate ozone gas near the sterile site 52, for example UV light at 185 nm is effective at creating a percentage of ozone from oxygen found in the air or fluids at the sterile site 52. Focus is placed on creating ozone gas or ozonated fluid because it will act to disinfect infectious agents in or near the sterile site 52. The ozone filled region 412 of the sterile site 52 will not present a risk of exposure to the patient and physician(s) because of several possible factors—1) the ozone gas could be created at minimal concentrations that are not harmful, 2) the ozonated fluid would be at a concentration that is not harmful, and 3) the ozone gas can be reverted to oxygen gas if it passes through an EMR barrier 161*e*. The EMR barrier 161*e* will be created by the EMR emitters 160*p*. The desired wavelength(s) of EMR used in the EMR barrier 161*e* will contain the wavelength(s) of EMR necessary to turn the ozone gas into oxygen gas, for example UV light at 200 nm-280 nm, and more specifically 254 nm is effective at converting a percentage of ozone gas back to oxygen gas. This occurrence makes the containment of ozone gas to the sterile site 52 possible. The feature of reverting ozone gas to oxygen gas is advantageous because it will reduce or eliminate excessive expose of ozone gas to the patient and physician(s).

FIGS. 160-161 illustrate the ability of the sterile site apparatus 1 to create a positive pressure region 422 in or near the sterile site 52. The sterile gas 32 needed to create this positive pressure region 422 will be released from gas release openings 31*c*.

Sterile gas 32 will be delivered to the housing 410 via the supply cord 40. The positive pressure region 422 is advantageous because it will cause a flow of sterile gas 423 to leave the sterile site 52. This flow of sterile gas 423 is advantageous because it will propel infectious agents away from the sterile site 52.

Figure 162:
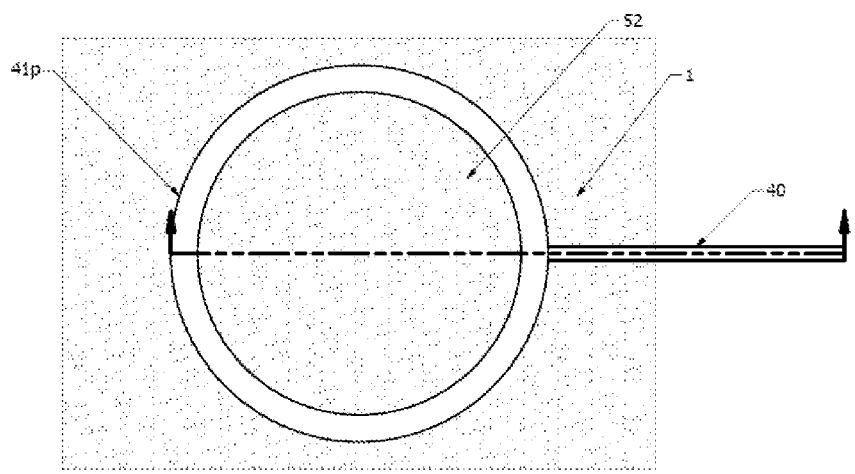
Figure 163:
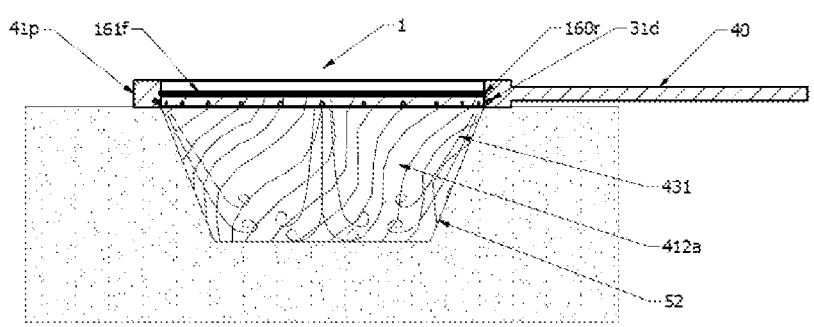

FIGS. 162-163 illustrate the ability of the sterile site apparatus 1 to pump ozone gas 431 into or near the sterile site 52 to create an ozone filled region 412*a*. The ozone gas 431 will be released from gas release openings 31*d*. The ozone gas 431 will be delivered to the housing 41*p* via the supply cord 40. Focus is placed on using ozone gas 431 because it will act to disinfect infectious agents in or near the sterile site 52. The ozone filled region 412*a* of the sterile site 52 will not present a risk of exposure to the patient and physician(s) as discussed in FIGS. 158-159 because the ozone gas 431 may be reverted to oxygen gas if it passes through an EMR barrier 161*f*. This EMR barrier 161*f* will be created by the EMR emitters 160*r*. As has been previously discussed, the EMR barrier 161*f* will contain the necessary wavelength(s) of EMR to turn ozone gas 431 into oxygen gas. This occurrence makes the containment of ozone gas 431 to the sterile site 52 possible.

Figure 164:
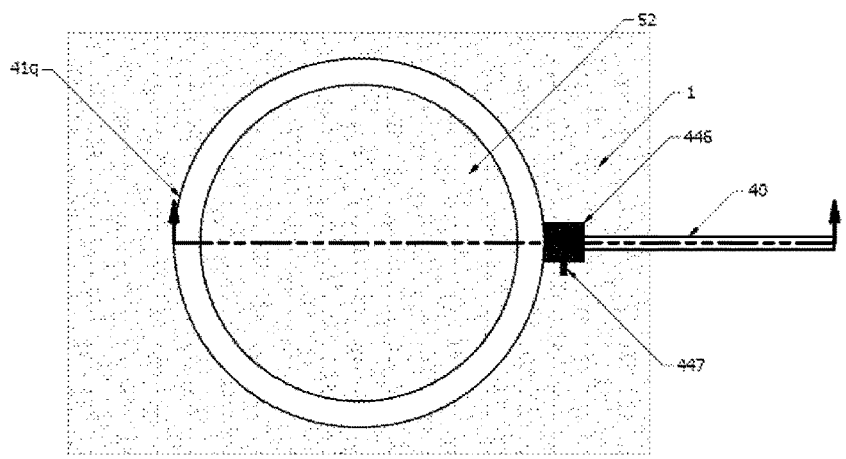
Figure 165:
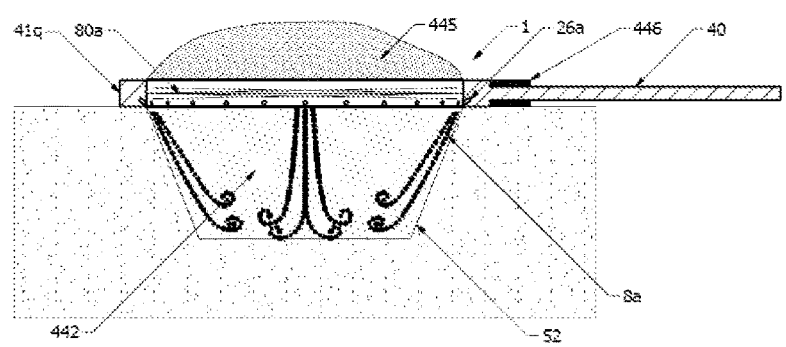
Figure 166:
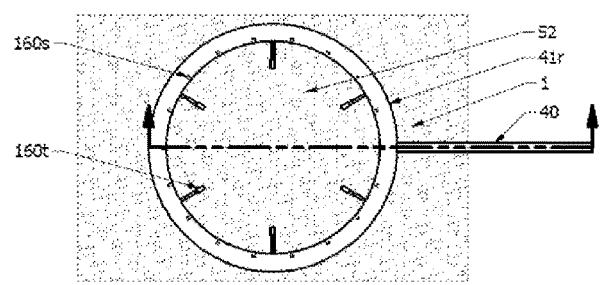

FIGS. 164-165 illustrate the ability of the sterile site apparatus 1 to provide fluids 8*a* into or near the sterile site 52. The fluids 8*a* will be released from the fluid release openings 26*a* in the housing 41*q* to be delivered near the sterile site 52 to form a coherent disinfecting fluid barrier 80*a*, a top cloud 445 between the sterile site apparatus 1 and the ambient surroundings, and/or a bottom cloud 442 between the sterile site apparatus 1 and the sterile site 52. As the fluids 8*a* used for disinfection are typically denser than the surrounding air, they will form a boundary for airborne infectious agents as well as infectious agents attached to objects such as surgical gloves, devices or instruments entering the sterile site 52. The fluids 8*a* may be delivered to the housing 41*q* via the supply cord 40, be injected, or be contained in a structure attached to the housing 41*q*. FIG. 164 shows a fluid reservoir 446, which will contain the fluids 8*a* used during a medical procedure, and an access port 447, which will be used to deliver the fluids 8*a* to the fluid reservoir 446 or the housing 41*q*.

Figure 167:
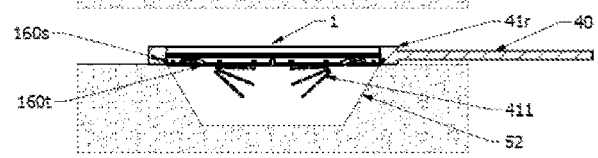
Figure 168:
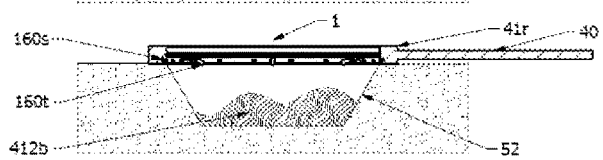
Figure 169:
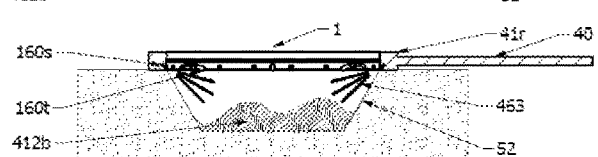
Figure 170:
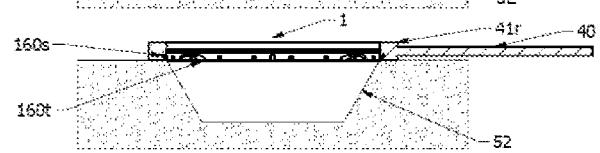

FIGS. 166-170 illustrate the ability of the sterile site apparatus 1 to emit pulses of ozone-generating EMR 411 and ozone-eliminating EMR 463. The ozone-generating EMR 411 and ozone-eliminating EMR 463 will be emitted from the ozone-generating EMR emitters 160*t* and ozone-eliminating EMR emitters 160*s*, respectively. The ozone-generating EMR 411 and the ozone-eliminating EMR 463 can be delivered to the housing 41*r* via the supply cord 40. FIGS. 167-170 show the sterile site apparatus 1 at successive time intervals. As seen in FIG. 167, the initial step involves pulsing the ozone-generating EMR 411 into or near the sterile site 52. As seen in FIG. 168, the result will be an ozone-filled region 412, which will disinfect any infectious agents in or near the sterile site 52. While the ozone filled region 412 is still present, as seen in FIG. 169, the ozone-eliminating EMR 463 will be pulsed into or near the sterile site 52. As seen in FIG. 170, the result will be a sterile site 52 that no longer contains the ozone-filled region 412. The feature of pulsing ozone-generating EMR 411 and ozone-eliminating EMR 463 is advantageous because it will reduce or eliminate excessive expose of ozone gas to the patient and physician(s).

FIGS. 171-172 illustrate the ability of the sterile site apparatus 1 to use an object sensor 3*c*, which is contained in the housing 41*s*, to detect an object 91 passing near or into the sterile site 52. The object 91 can be large objects, such as a physician's hand(s), medical device, or small microscopic objects such as infectious agents. FIGS. 171 and 172 depict one of the detecting mechanisms that can be used by the object sensor 3*c*, which uses a detecting region 471. When an object 91 passes near or through this detecting region 471, a disrupted region 472 will result. This disruption can be used as a means to activate/deactivate various features of the sterile site apparatus 1. For example, when an object 91 disrupts the detecting region 471, it could cause a feature to disinfect the object 91 before it comes into contact with the sterile site 52. A variety of contact and non-contact object sensors 3*c*, such as a microswitch, infrared, ultrasonic, capacitance, laser, laser scanner, laser displacement, optical, inductance, photoelectric, light sensor, pressure sensor, temperature sensor, biosensor or numerous others, can be used. While the object sensor 3*c* described in FIGS. 171-172 shows a distinct detecting region 471 and disrupted region 472, these regions do not have to be included in the object sensor 3*c* so long as the functional aspects of the sensor are ensured.

FIGS. 173-174 illustrate the ability of the sterile site apparatus 1 and its associated housing 41*bg* to use several sensors to gain information on the sterile site 52 and objects/infectious agents contained outside of the sterile site 52 and to detect if an object/infectious agent will to come into contact with the sterile site 52. As also seen in FIGS. 171-172, FIG. 174 shows the object sensor 3*c* and its associated detecting region 471*a* to detect if an object will come into contact with the sterile site 52. The object sensors 3*b* will be used to gain information on the objects contained outside of the sterile site 52. The object sensors 3*b* will determine an object's shape, external and internal geometry, material composition, position, velocity, trajectory, type of infectious agent or object, surface characteristics, and susceptibility to various types of disinfection or displacement along with various other characteristics, properties, and features. The sterile site sensors 3*d* will be used to gain information on the sterile site 52. The sterile site sensors 3*d* will determine a sterile site's 52 shape, external and internal geometry, material/tissue composition, if an object or infectious agent is in contact with the sterile site 52, type of object or infectious agent, surface characteristics, temperature, and susceptibility to various types of disinfection along with various other characteristics, properties, and features. All sensors of the sterile site apparatus 1, will be used to activate/deactivate, modify, and/or alter various features of the sterile site apparatus 1 including but not limited to EMR intensity, EMR wavelength(s), fluid or gas mixture composition, fluid or gas delivery/removal rate, electrode power, CAP delivery rate, and ionic composition of fluids or gases.

In one example, the sensors may be configured to monitor the amount of EMR that is emitted in the EMR barrier and/or in the vicinity of the sterile site 52. The sensors may also provide the monitored data to the control system 20 which may then provide feedback to the emitters to adjust the amount of EMR in the EMR barrier and/or the sterile site 52 accordingly.

Figure 175:
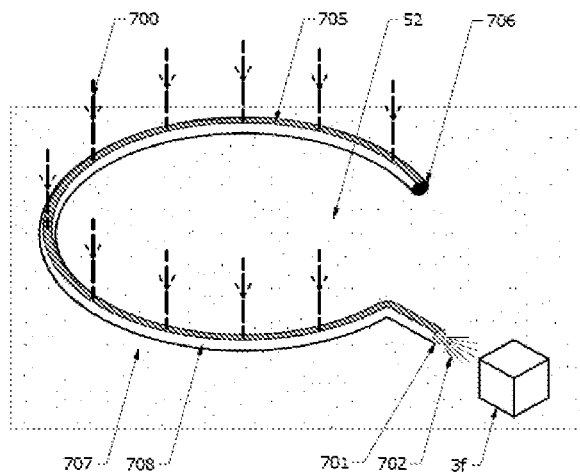
Figure 176:
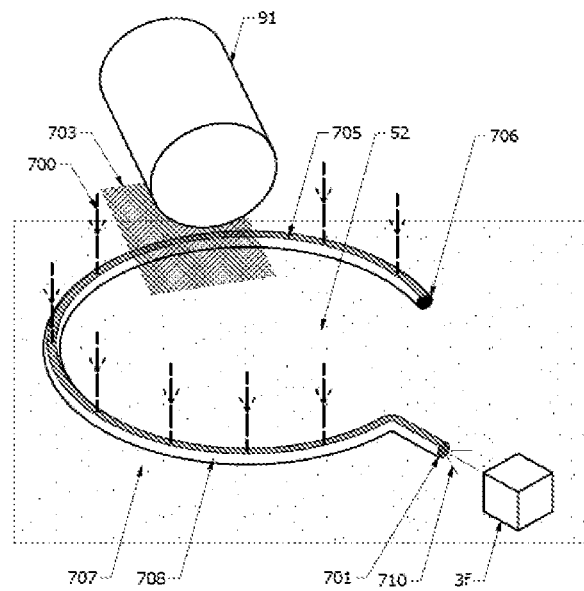

FIGS. 175-176 illustrate the function of the visible light detection system 707, which will be used by the sterile site apparatus 1 (FIG. 1). The visible light detection system 707 will be used to detect the presence of an object 91, which could come into contact with the sterile site 52. The detection of an object 91 is advantageous because it can be used as an input for the control system 20 (FIG. 1) to activate or deactivate various features of the sterile site apparatus 1 such as creating an EMR barrier 161 (FIG. 73.) The visible light detection system 707 will consist of components and features including but not limited to those seen in FIGS. 175-176. Visible light 700 will enter the transmission structure 708 via the visible light inlet 705. The transmission structure 708 will be designed and composed of materials to allow efficient transmission of visible light and keep the visible light contained within the transmission structure 708. One of the features that will aid in this containment is the reflective end surface 706, which will prevent undesired losses of visible light by reflecting the visible light in the transmission structure 708 back towards and into the transmission structure 708. The visible light inlet 705 will allow the visible light 700 to enter the transmission structure 708 and also minimize the amount of visible light that can escape from the transmission structure 708. While the visible light inlet 705 in FIGS. 175 and 176 is shown as a continuous feature along the top of the transmission structure 708, the visible light inlet 705 can have any of number of segments, components, orientations and patterns. Once the visible light 700 enters and is contained within the transmission structure 708, it will be released from the visible light outlet 701.

When an object 91 is not present near the sterile site 52, the visible light leaving the visible light outlet 701 will be described as high levels of visible light 702. The intensity and power of the high levels of visible light 702 will be detected by the visible light sensor 3f. When an object 91 is located near the sterile site 52, it will create a shadow 703 that will prevent some of the visible light 700 from entering the transmission structure 708. By preventing some visible light 700 from entering the transmission structure 708, lower levels of visible light 710 will leave the visible light outlet 701. The intensity and power of the lower levels of visible light 710 will be detected by the visible light sensor 3f. The control system 20 will be able to determine when an object 91 is moving towards the sterile site 52 because the object 91 will cause a decrease in the visible light detected by the visible light sensor 3f. Also, the control system 20 will be able to determine when an object 91 is moving away from the sterile site 52 because the object 91 will cause an increase in the visible light detected by the visible light sensor 3f.

Figure 177:
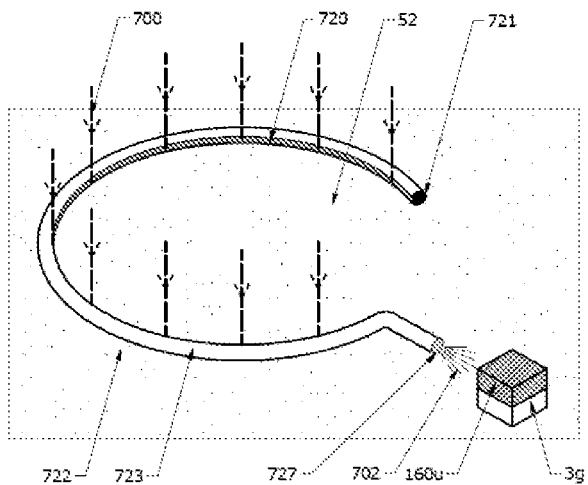
Figure 178:
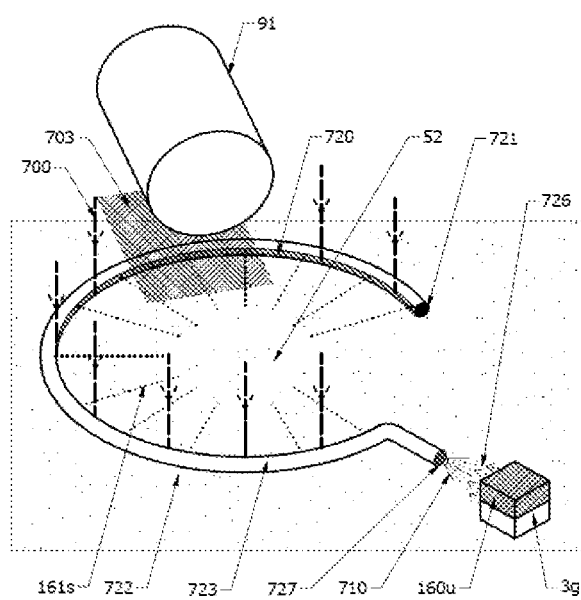

FIGS. 177-178 illustrate the function of the visible light detection and EMR emission system 722, which will be used by the sterile site apparatus 1 (FIG. 1). The visible light detection and EMR emission system 722 will be used for two purposes: detecting an object 704 near the sterile site 52 and emitting an EMR barrier 161. To address the function of the visible light detection and EMR emission system 722, it will be helpful to observe its similarities to the visible light detection system 707 in FIGS. 175-176, which includes its ability to detect an object 704 near the sterile site 52 by observing changes in the amount of visible light detected by the visible light sensor 3g. The visible light inlet/EMR emitter 720 will function similar to the visible light inlet 705, but the visible light inlet/EMR emitter 720 will also be able to emit EMR that can be used to create the EMR barrier 161. While the visible light inlet/EMR emitter 720 in FIGS. 177 and 178 is shown as a continuous feature along the inner face of the transmission structure 723, the visible light inlet/EMR emitter 720 can have any of number of segments, components, orientations and patterns. The reflective end face 721 will function similar to the reflective end face 706, but the reflective end face 721 will also be able to reflect other desired wavelengths of EMR in addition to visible light. The transmission structure 723 will function similar to the transmission structure 708, but the transmission structure 723 will also be able to transmit and contain other desired wavelengths of EMR in addition to visible light. The visible light outlet/EMR inlet 727 will function similar to the visible light outlet 701, but the visible light outlet/EMR inlet 727 will also be able to receive EMR 726 from the EMR emitter 160u. The visible light sensor 3g will function similar to the visible light sensor 3f. For the purpose of emitting an EMR barrier 161, EMR 726 released by the EMR 160u will enter the transmission structure 723 via the visible light outlet/EMR inlet 727. After being efficiently transmitted and contained within the transmission structure 723, the EMR will be released from the visible light inlet/EMR emitter 720. The EMR will then be used to create the EMR barrier 161. As shown in FIG. 176, a shadow 703 from an object 704 will cause a change in the amount of visible light detected by the visible light detection and EMR emission system 722, which can be used as an input to trigger the creation of an EMR barrier 161 to disinfect the object 704 before it can come into contact with the sterile site 52.

Figure 179:
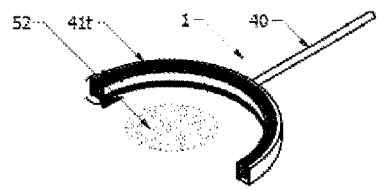
Figure 180:
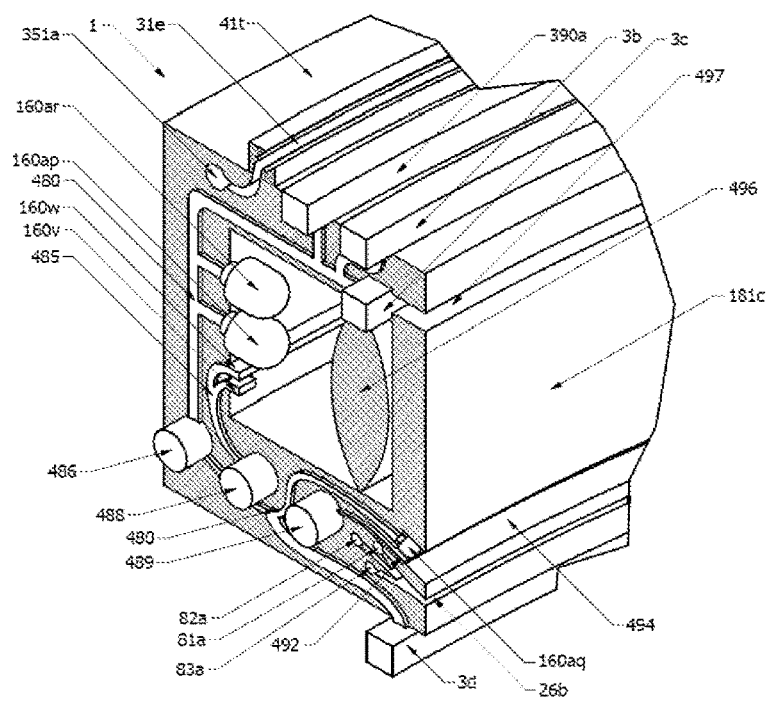

FIGS. 179-180 illustrate the ability of the sterile site apparatus 1 to be composed of a multitude of various features and systems. While FIG. 180 shows these features and systems collectively, it should be noted that they can be omitted and additional features or systems can be included. The primary power line 486, primary fiber optics for the EMR barrier 488, primary fiber optics for EMR entering the sterile site 489, fluid and gas lumen 351a for the gas release openings 31e, and the liquid lumen 81a, gas lumen 82a, and suspended solids lumen 83s for the fluid release openings 26b will be supplied or powered by the supply cord 40.

The primary power line 486 will branch off to form secondary power lines 480, which will power the object sensors 3b and 3c, sterile site sensor 3d, visible light EMR emitter(s) 160ar, desired wavelength(s) of EMR emitter(s) 160ap, sterile site EMR emitter 160aq, and the positively charged electrode 390a. The sensors 3b, 3c, and 3d, as depicted in FIGS. 171-174, will act as a mechanism to activate/deactivate and/or adjust various features of the sterile site apparatus 1 when an object, such as a physician's hand or infectious agent, has been sensed near or on the sterile site 52 or when conditions of the sterile site 52 change. The object sensor 3c will be able to "see" objects through an object sensor opening 497 or it will sense objects through the housing 41t if the object sensor opening 497 is not present. The visible light EMR emitter(s) 160ar will generate visible light, which will be used to enhance the visibility of the area near the sterile site 52. The desired wavelength(s) of EMR emitters 160ap will generate the desired wavelength(s) of EMR, which will be used to create the EMR barrier. The sterile site EMR emitters 160aq will be used to generate the sterile site EMR that can be emitted into or near the sterile site 52. The function of the sterile site EMR includes but is not limited to illuminating the sterile site 52, generating ozone gas and eliminating ozone gas. The positively charged electrode 390a will be used to attract or repel infectious agents away from the sterile site 52. While a positively charged electrode 390a is shown in FIG. 180, a negatively charged electrode can be used in its place.

The primary fiber optics for the coherent EMR barrier 488 will distribute the desired wavelength(s) of EMR needed for the EMR barrier. The primary fiber optics for the EMR barrier 488 will branch off to form secondary fiber optics for the EMR barrier 485. The secondary fiber optics for the EMR barrier 485 will emit their contents to form line source EMR emitters 160w, point source EMR emitters 160v, or any of a number of types of forms not shown in FIG. 180. The various types of EMR from the visible light EMR emitter(s) 160ar, the desired wavelength(s) of EMR emitter(s) 162ap, the line source EMR emitter(s) 160w, and the point source EMR emitter(s) 160v will be passed through the optics mechanism 496. The optics mechanism 496 will take various wavelengths of EMR and focus them into an EMR barrier. While a convex profile is shown for the optics mechanism 496 in FIG. 180, a configuration of any number of any types of lenses and optics can be used. To form the EMR barrier, the light will initially pass through the reflective surface 181c. However, the reflective surface 181c will only allow EMR to pass in the direction leading to the area above the sterile site 52. In other words, EMR traveling from the area above the sterile site 52 towards the reflective surface 181*c* will be reflected back towards the area above the sterile site 52.

The primary fiber optics for EMR entering the sterile site 489 will branch off to form secondary fiber optics for EMR entering the sterile site 492, which will emit sterile site EMR into or near the sterile site 52. The sterile site EMR from the secondary fiber optics for EMR entering the sterile site 492 and sterile site EMR emitters 160*aq* will pass through a sterile site EMR opening 494 to access the sterile site 52 and its surroundings.

The sterile site apparatus 1 will also include a fluid and gas lumen 351*a*, liquid lumen 81*a*, gas lumen 82*a*, and suspended solids lumen 83*s*. The fluid and gas lumen 351*a* will supply the gas release openings 31*e*. The liquid lumen 81*a*, gas lumen 82*a*, and suspended solids lumen 83*s* will supply the fluid release openings 26*b*. These lumens can supply gases, liquids, solids, gas mixtures, liquid mixtures, solids mixtures, gas and liquid mixtures, gas and solid mixtures, liquid and solid mixtures, and liquid, gas, and solid mixtures including but not limited to ozone gas, sterile gas, sterile humidified gas, carbon dioxide, CAP, antibiotics. These mixtures can be delivered near the sterile site 52 through fluid release openings 26*b*. The functions of the gas release openings 31*e* can include but are not limited to infectious agent displacement and disinfection. The function of the fluid release openings 26*b* will include but is not limited to disinfection of the sterile site 52.

Figure 181:
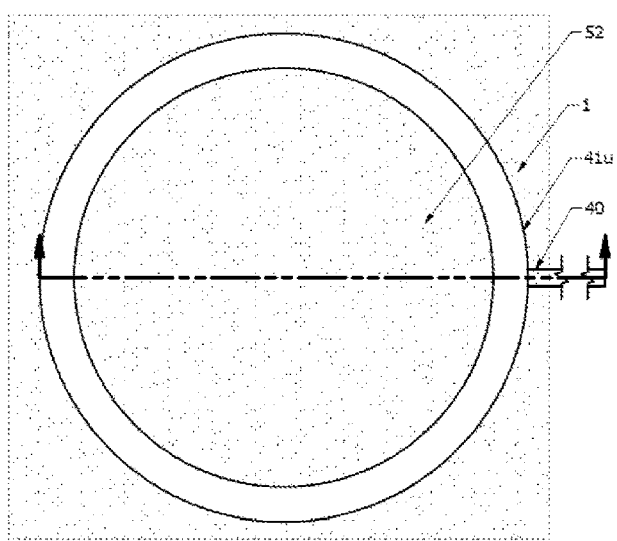
Figure 182:
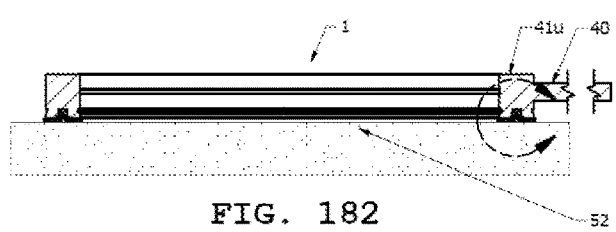
Figure 183:
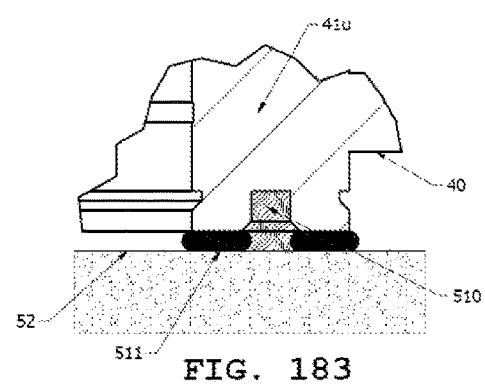

FIGS. 181-183 illustrate the ability of the sterile site apparatus 1, which consists of an attached suction gasket 511, to be sealed against the sterile site 52 using suction. This can be performed by creating a region of negative pressure 510 within the housing 41*u*. The region of negative pressure 510 can either be generated by the sterile site equipment 27 (FIG. 3) or be incorporated into the profile of the suction gasket 511 similar to a suction cup. Using suction to attach the sterile site apparatus 1 to the sterile site 52 will ensure that the sterile site apparatus 1 is secure and will prevent infectious agents from coming into contact with the sterile site 52 after they travel under the sterile site apparatus 1.

FIGS. 184-185 illustrate the ability of the sterile site apparatus 1, which consists of an attached conformable gasket 520, to be sealed against the sterile site 52. Having a conformable gasket 520 attached to the bottom of the sterile site apparatus 1 will allow the sterile site apparatus 1 to be sealed against the patient or drape even when a non-uniform surface 521 is encountered. The conformable gasket 520 may also minimize the angulation that the housing 41*bh* undergoes to contour to a non-uniform surface 521, thereby allowing the housing 41*bh* to remain oriented in a single plane. To prevent infectious agents from coming into contact with the sterile site 52, the conformable gasket 520 should be designed to completely seal the bottom surface of the sterile site apparatus 1 to the sterile site 52.

FIGS. 186-189 illustrate the ability of the sterile site apparatus 1, which consists of an attached positively charged magnetic strip 530, to be sealed against the sterile site 52 using a negatively charged magnetic strip 531. Note that although FIGS. 186-189 show the positively charged magnetic strip 530 initially attached the sterile site apparatus 1 and the negatively charged magnetic strip 531 initially attached to the sterile site 52, the position of the strips can be reversed. The sterile site apparatus 1 and sterile site 52 surface will be attached and sealed to each other once the positively charged magnetic strip 530 and negatively charged magnetic strip 531 engage. To prevent infectious agents from coming into contact with the sterile site 52, the magnetic strips 530 and 531 should be designed to completely seal the bottom surface of the sterile site apparatus 1 and housing 41*bi* (if present) to the sterile site 52.

FIGS. 190-191 illustrate the ability for the sterile site apparatus 1 to protect the sterile site 52 and the user from being exposed to EMR released at a potentially harmful trajectory 541, which is released by the EMR emitter(s) 160*x*. The EMR released at a potentially harmful trajectory 541 will be prevented from reaching the patient and physician(s) by using a shield 540, which is attached to and surrounds the sterile site apparatus 1. The shield 540 will be composed of features/materials that will not allow the transmission, reflection, or refraction of high levels of potentially harmful EMR to the surrounding areas where the patient and physician(s) will be located. The shield 540 is shown positioned on both sides of the housing 41*v*, but may be partial or complete and on one or both sides of the housing 41*v* as required to reduce potentially harmful trajectories 541. It is also noted that the shield 540 can be utilized to reduce harmful trajectories of gases 4 (FIG. 1), CAP 7 (FIG. 1), fluids 8 (FIG. 1), and sterile or purified gas from the gas handling unit 10 (FIG. 1) in place of or in addition to the EMR. The shield 540 will help to guarantee that operating the sterile site apparatus 1 poses minimal to no danger to the patient and user.

FIGS. 192-193 illustrate the ability of the sterile site apparatus 1 to use a retracting feature 542 to maintain, decrease, and/or increase the size of the opening that is used to access the sterile site 52 while also preventing infectious agents contained on the exterior surface 544 from coming into contact with the sterile site 52. It should be noted that for the embodiment shown in FIGS. 192-193, the sterile site 52 is located within a mass of body tissue 547. While the sterile site apparatus 1 shown in FIGS. 192-193 illustrates the retracting feature 542 attached to the housing 41*bj*, the retracting feature 542 can be located anywhere with respect to the sterile site apparatus 1 and may be used with or without the housing 41*bj*. It is conceivable that the exterior surface 544 can be the skin of a patient. It is conceivable that the isolated region 546 is exposed body tissue 547. The interface region 545 is part of the exterior surface 544 that is coincident with the isolated region 546. The retracting feature 542 can retract body tissue 547 by interacting with existing retraction equipment, by being opened, closed, and shaped by the user, or by being automatically opened, closed, and shaped by the sterile site apparatus 1 and its associated control system 20 (FIG. 1). The retracting feature 542 can be made of a variety of known materials including but not limited to those that are flexible, rigid, and malleable. It should be noted that the retracting feature 542 can be made of a single or multiple components and have appearances, shapes, and configurations other than that shown in FIGS. 192-193. Without the use of the retracting feature 542, infectious agents on the exterior surface 544 could migrate to the sterile site 52 after the infectious agents at the interface region 545 and exterior surface 544 are contacted by objects, such as a user's hand or medical instrument. When these objects are in contact with the sterile site 52, the infectious agents will then also come into contact with the sterile site 52. The retracting feature 542 will create the isolated region 546 and cover the interface region 545. By covering and isolating the interface region 545, infectious agents at the interface region 545 will not come into contact with object such as the user's hand or a medical device.

FIGS. 194-195 illustrate the ability of the sterile site apparatus 1 to include an ergonomic attachment 550, which will improve the comfort and health of the users using the sterile site apparatus 1. It should be noted that the ergonomic attachment 550 can consist of a single or multiple pieces and can be located anywhere on the sterile site apparatus 1. The shape of the single or multiple pieces of the ergonomic attachment 550 can be different than that shown in FIGS. 194-195, and may or may not be adhered to the housing 41*bk*.

FIGS. 196-198 illustrate the ability of the sterile site apparatus 1 to be composed of a multitude of various features and systems. While FIGS. 197 and 198 show these features and systems collectively, it should be noted that some features can be omitted and additional features or systems can be included. The positively charged electrode 390*b*, which is part of the charged particle displacement mechanism 9 (FIG. 1), will act to attract or repel infectious agents in a manner to prevent them from coming into contact with the sterile site 52. It should be noted that although FIG. 198 shows a positively charged electrode 390*b* being used, a negatively charged electrode can be used in its place. The gas release opening 31*f* will release sterile gas 32 or other gas mixtures to displace infectious agents in a way that will prevent them from coming into contact with the sterile site 52. The shield 540*a* will protect the patient and physician(s) from being exposed to EMR released at a potentially harmful trajectory. While the EMR barrier 161*g*, which is created by the EMR emitters 160*y*, will be designed to prevent EMR from being released at a potentially harmful trajectory, the safety feature of using the shield 540*a* will help to guarantee that operating the sterile site apparatus 1 poses minimal to no danger to user. An ergonomic attachment 550*a* can be used to improve the comfort and health of the user operating the sterile site apparatus 1. An attachment mechanism 573 will be used to attach and/or seal the sterile site apparatus 1 to the sterile site 52. The attachment mechanism 573 can consist of multiple or single magnetic strips, gaskets, grip pads, adhesives, or suction features. The attachment mechanism 573 is configured so the sterile site apparatus 1 will be firmly attached to the sterile site 52 while creating a seal to prevent infectious agents from passing under the housing 41*w*, which could cause the infectious agents to come into contact with the sterile site 52. A detecting region 471*b*, which is created by the object sensor 3*c*, can be used to detect a physician's hand, small objects, such as a hemostat, and microscopic objects, such as infectious agents, traveling into or near the sterile site 52. The object sensor 3*b* will be used to detect objects in the ambient surroundings near the sterile site apparatus 1. The sterile site sensor 3*d* will monitor conditions of the sterile site 52 including but not limited to infectious agents in contact with the sterile site 52 and growth of an infection. The ability to detect the presence of an object near the sterile site 52 or the conditions of the sterile site 52 will allow certain features of the sterile site apparatus 1, such as illuminating the sterile site 52 or creating an EMR barrier 161*g*, to be activated only when needed. This will prolong the service life of the sterile site apparatus 1 and minimize exposure to unnecessary radiation and potentially harmful chemicals. The EMR barrier 161*g* can be used to disinfect objects that can come into contact with the sterile site 52 by using the desired wavelength(s) of EMR. The EMR barrier 161*g* can have a variety of functions including but not limited to disinfection and illumination. A coherent EMR barrier will be able to disinfect the entire exterior surface of an object before it comes into contact with the sterile site 52. It will also be able to disinfect the exterior of objects traveling towards the sterile site 52 even when multiple objects are simultaneously passing through the sterile site apparatus 1. It is implied that the EMR barrier 161*g* is planar, following a plane defined by the inner diameter of the housing 41*w*, however, it is also contemplated that the EMR barrier 161*g* be arcuate or shaped like a dome, whereby the electromagnetic radiation follows the contour of a gas, fluid or solid shape. Sterile site EMR 577, which is released by separate EMR emitters 160*z*, will be released in the area in or near the sterile site 52, where it can perform a number of functions including but not limited to ozone generation, ozone elimination, and illumination. Fluids 8*b* will be released in the area in or near the sterile site 52 by fluid release openings 26*c* to perform a variety of functions that include but are not limited to mold spore neutralization and infectious agent disinfection. A vacuum head 42*a* can also be used to remove infectious agent containing air 43 away from the sterile site 52.

It should also be noted that the portions of the sterile site apparatus 1 of FIG. 197 that are on or near the sterile site 52 must be configured to be sterile so as not to transmit infectious agents to the sterile site 52. This may be accomplished by any combination of a) the portions of the sterile site apparatus 1 that are on or near the sterile site 52 are sterilized and re-usable (able to be cleaned and re-sterilized by common sterilization methods such as autoclaving, ethylene oxide gas, gamma, or ebeam); b) the portions of the sterile site apparatus 1 that are on or near the sterile site 52 are sterilized and disposable; c) the portions of the sterile site apparatus 1 that are on or near the sterile site 52 are covered with a sterile cover; or d) the portions of the sterile site apparatus 1 that are on or near the sterile site 52 are able to be self-sterilized by the sterile site apparatus 1 itself before or during its use.

FIGS. 199-202 illustrate to ability of the housing 41*x* and supply cord 40 of the sterile site apparatus 1 to be covered by a sterile sleeve 600. FIGS. 199-202 show the progression as the sterile sleeve 600 is slid on the housing 41*x* followed by the supply cord 40. The sterile sleeve 600 is advantageous because it will ensure that any portion of the sterile site apparatus 1 that is used on or near a sterile site 52 will not cause contamination of the sterile site 52. The sterile sleeve 600 can be made of any material, but preferably it is made of plastic, and more specifically out of polyethylene which is commonly used as a disposable sterile covering for medical equipment and apparatus. It is also contemplated to create a porous sterile sleeve 600 that will allow gas and fluid mixtures to pass through, such as Tyvek (DuPont) which is commonly used for sterile medical apparatus. It is further contemplated that the sterile sleeve 600 be made of a combination of materials such as polyethylene and Tyvek that would not hinder the performance of the sterile site apparatus 1 as described in the preceding embodiments.

FIGS. 203-204 illustrate the ability of the housing 41*bl* of the sterile site apparatus 1 to be covered by a sterile, rigid cover, which consists of a sterile, rigid top component 610 and a sterile, rigid bottom component 611. The sterile, rigid top component 610 and bottom component 611, will attach to form a sterile rigid cover for the housing 41*bl*. The sterile, rigid cover is advantageous because it will ensure that any portion of the sterile site apparatus 1 that is used on or near a sterile site will not cause contamination of the sterile site. The sterile, rigid cover can be made of any material, but preferably it is made of plastic or glass, and more specifically out of acrylic, polycarbonate, or quartz which is commonly used in medical equipment and apparatus, especially when it is desirable to be transparent. It is also contemplated that the sterile, rigid cover be made of a combination of materials such as acrylic and tyvek that would not hinder the performance of the sterile site apparatus 1 as described in the preceding embodiments.

FIG. 205 illustrates the use of a movable arm 620 with sterile site apparatus 1 to allow the user to place the sterile site apparatus 1 in a location near the sterile site. The movable arm 620 can consist of movable joints 144, hollow rigid members 143, and attachment location 621. The movable arm 620 can use joints that can maintain their position by friction, locking, or any other method commonly used with articulated arms to position and hold medical apparatus.

FIG. 206 illustrates how an object 634 can be disinfected or kept free of infectious agents by using a sterile site apparatus 1. An object 634 can be disinfected or kept free of infectious agents by passing it through an EMR barrier 161$h$, which is created by the EMR emitter 160$aa$, and into an enclosure created by the housing 41$y$. This sterile site apparatus 1 is advantageous because it gives users the ability to disinfect their hands, forearms, gloves, medical instruments, or other objects before they come into contact with a sterile site 52. The housing 41$y$ can be supported by a pole 632 and base 633, or it can be mounted on a wall or any other structure that can support the housing 41$y$ and provide ample access to the user. It is also contemplated that any of the features described in the preceding embodiments can be substituted for or combined with the EMR barrier 161$h$ to enhance the sterile site apparatus 1 of FIG. 206. For example, ozone gas flowing into the housing 41$y$ will disinfect the enclosure and prevent infectious agents from existing in the sterile site 52.

FIG. 207 illustrates how an object in an enclosure can be kept free of infectious agents by using a sterile site apparatus 1. An object 634$a$ can be kept free of infectious agents by passing it through an EMR barrier 161$i$, which is created by the EMR emitter 160$ab$, and into an enclosure created by the housing 41$z$. It is also contemplated that any of the features described in the preceding embodiments can be substituted for or combined with the EMR barrier 161$i$ to enhance the sterile site apparatus 1 of FIG. 207. For example, sterile gas flowing into the housing 41$z$ will create a positive pressure in the enclosure to help prevent infectious agents from entering the sterile site 52.

FIGS. 208-209 illustrate the ability of the sterile site apparatus 1 and its housing 41$am$ to form enclosures where an object (not shown), such as a chemical or medical device, can be placed or manipulated while isolating the object from the user and infectious agents contained in the ambient surroundings. While the sterile site apparatus 1 in FIGS. 208-209 shows three connected enclosures, more or fewer enclosures of various designs may be used in place of or in conjunction with those shown. Whenever the object needs to be manipulated by the user, such as moving the object from one enclosure to the other, the user will insert their left and right hands through the left and right glove sleeve entrances 649 and 650, respectively, and into the left and right glove sleeves 647 and 648, respectively. The glove sleeves 647 and 648 will allow the user to manipulate an object inside of an enclosure without coming into direct contact with the object or other contents of the enclosures. It should be noted that before use, the sealing features 639, 651, 652, and 653 will be closed and the entrance enclosure 636, primary enclosure 635 and exit enclosure 637 will be sterile to ensure that the sterile site apparatus 1 does not contain any infectious agents. The sealing features 639, 651, 652 and 653 can use a variety of known technologies to create a seal including but not limited to gaskets, zippers, adhesives, and magnetic strips and can used in multiple locations in conjunction with or in place of those shown in FIGS. 208-209. The sealing feature 639 will create a seal between the ambient surroundings and the entrance enclosure 636. The sealing feature 651 will create a seal between the entrance enclosure 636 and the primary enclosure 635. The sealing feature 652 will create a seal between the primary enclosure 635 and the exit enclosure 637. The sealing feature 653 will create a seal between the exit enclosure 637 and the ambient surroundings. The entrance enclosure 636, primary enclosure 635, and exit enclosure 637 will be supported, have their shape maintained, and held in position by features including but not limited to the base supports 646, cross supports 645, and protective material 644. The base supports 646 and cross supports 645 can utilize known technologies including but not limited to rigid components, flexible components, inflatable components, and collapsible features to maintain the integrity of the enclosures. The protective material 644 that will form the walls of the enclosures and all other materials used by the sterile site apparatus 1 will be transparent, translucent, or opaque materials that will serve to protect and isolate the user from conditions within the enclosures including but not limited to hazardous drugs, chemicals, fumes, vapors, liquids, solids EMR, sharp edges, and high pressures.

It is also conceivable that the enclosures 636, 635, and 637 will maintain their shape by being inflated with combinations of gas, liquid, Cold Atmospheric Plasma (CAP) and/or solid mixtures. The combinations of gas, liquid, CAP, and/or solid mixtures will be delivered to the entrance enclosure 636, primary enclosure 635, and exit enclosure 637 through the inlet ports 640, 642, and 655, respectively. The combinations of gas, liquid, CAP, and/or solid mixtures will be removed from the entrance enclosure 636, primary enclosure 635, and exit enclosure 637 through the outlet ports 641, 643, and 656, respectively. The inlets ports 640, 642, and 655 and the outlet ports 641, 643, and 656 will transfer combinations of gas, liquid, CAP and/or solid mixtures via the supply cord 40 (FIG. 3). The gas, liquid, CAP and/or solid mixtures can serve a variety of other functions besides inflation which include but are not limited to disinfection, infectious agent displacement, and neutralizing hazardous materials. The sterile site apparatus 1 can also implement EMR emitters 160$ac$ and 160$ad$ of the entrance enclosure 636 and the exit enclosure 654, respectively. The EMR emitters 160$ac$ and 160$ad$ will create an EMR barrier 161 (FIG. 73), which will serve a variety of functions including but not limited to disinfection, illumination, and ozone gas generation.

FIG. 210 illustrates the ability of the sterile site apparatus 1 to be used for post-operative monitoring of the sterile site 52. For this configuration, the housing 41$aa$ and possibly the sterile site equipment 27$a$, which can be connected to each other via the supply cord 40$b$, will be attached to the patient 660 during normal day-to-day to activities. In this instance, the sterile site 52 can represent a healing wound or a chemotherapy/dialysis access port. The sterile site apparatus 1 will monitor the conditions of the sterile site 52 to check for signs of infection or other complication. Upon recognition of the infection or other complication, the sterile site apparatus 1 will activate various features to alert the patient or medical personnel of the infection or other complication and/or take measures, such as administering disinfect fluids, to actively disinfect the sterile site 52 to slow the growth of the infection or eliminate it entirely.

FIGS. 211-213 illustrate the ability of the sterile site apparatus 1 to be attached to an intravenous device 473 to protect the sterile site 52, which is shown as the access location 474 of the intravenous device 473 in FIG. 213. For this configuration, the housing 41*bm* will at least partially surround the sterile site 52 while still allowing access for a medical instrument. The object sensor 3*c* would detect an object or infectious agent as it approaches the sterile site 52. Upon detection of an object or infectious agent, the object 3*c* will send a signal to the control system 20*a*, which can be powered by a battery 476, via the transmission wire 475. The battery 476 and control system 20*a* will be considered as part of the sterile site equipment 27*b*. The configuration in FIG. 213 is unique because the sterile site equipment 27*b* is contained within the housing 41*bm*. The control system 20*a* will then send a signal the EMR emitters 160*ae*, which will create an EMR barrier 161*j* to disinfect the incoming object or infectious agent and/or the sterile site 52. This will prevent contamination of an intravenous line, which will reduce the risk of infection by preventing infectious agents from coming into contact with the sterile site 52.

FIGS. 214-221 illustrate the ability of the sterile site apparatus 1 to be a portable system used to disinfect infectious agents contained in and on an intravenous access device 755. FIGS. 214-217 show the sterile site apparatus 1 before it has become engaged with the intravenous access device 755. FIGS. 218-221 show the sterile site apparatus 1 once it has become engaged with and is disinfecting the intravenous access device 755 with an EMR barrier 161*k*. For the configurations shown in FIGS. 214-221, the infectious agents will be located on the leading interior surface 759 and leading exterior surface 760 of the intravenous access device 755. The sterile site 52 will be described as the inner portion of the intravenous access device 755 that is distant from the leading interior surface 759 and the leading exterior surface 760. If infectious agents were to come near the sterile site 52, it is possible that they would travel through the intravenous access device 755, reach the patient and cause an infection. The housing 41*ab* of the sterile site apparatus 1 will consist of a rear portion 752 and a front portion 753. The front portion 753 will be able to rotate about the housing hinge joint 750. When the sterile site apparatus 1 is not in use, the front portion 753 can rest in the depressed region 751 to allow for a compact profile. The sterile site apparatus 1 will also have an attachment clip 756 with grip features 758, which will be able to rotate about the clip hinge joint 757. The attachment clip 756 will allow the sterile site apparatus 1 to be attached to a surface or object and allow for greater portability. The front portion 753 of the housing 41*ab* will contain a sensor 3*e* to detect when the sterile site apparatus 1 and intravenous access device 755 are engaged, an attachment feature 761 to engage the sterile site apparatus 1 with the intravenous access device 755, an EMR emitter 160*af* to create the EMR barrier 161*k*, and an EMR shielding feature 754 to prevent EMR from escaping the enclosure of the front portion 753, which could cause EMR exposure to the user or patient. The use of the sensor 3*e* is advantageous because the presence of an intravenous access device 755 will act as a necessary input for the control system 20 (FIG. 1) to create the EMR barrier 161*k*. To extend the service life of the sterile site apparatus 1 and prevent EMR exposure to the user or patient, the EMR barrier 161*k* only needs to be activated when it is coming into contact with the intravenous access device 755. While the attachment feature 761 is shown as threading, any known method(s) for connecting two objects can be used in place of or in conjunction with the threading. While the EMR barrier 161*k* is shown as being emitted towards the leading interior surface 759 and leading exterior surface 760 of the intravenous access device 755, the EMR barrier 161*k* may be used on any part of an intravenous access device 755. While the EMR shielding feature 754 is shown in FIGS. 214-221 as a valve or membrane that can be crossed by the intravenous access device 755, the EMR shielding feature 754 can use any known technologies for sealing around an object.

FIGS. 222-224 illustrate the ability of the sterile site apparatus 1 to couple two tubular medical devices and disinfect the fluid flowing through them. The housing 41*ac* of the sterile site apparatus 1 will contain two couplers 780, which will couple the inlet tubular medical device 782 and outlet tubular medical device 781 to the sterile site apparatus 1. The couplers 780 will also create seals between the tubular medical devices and the sterile site apparatus 1 to prevent fluid 785 from leaking out into the ambient surroundings. For the configuration shown, fluid 785 will be flowing from the inlet tubular medical device 782 to outlet tubular medical device 781. The sterile site 52 will be a portion of the inner region of the outlet tubular medical device 781 that is distant from the sterile site apparatus 1. The housing 41*ac* will contain features and components including but not limited to a flow sensor 3*h*, control system 20*b*, battery 476*b*, EMR emitters 160*ah*, transmission wires 784, EMR emitters 160*ag* and fiber optics 320. The flow sensor 3*h* can use any of a number of known technologies to measure the flow rate of the fluid 785 without contacting the fluid 785. The flow sensor 3*h*, control system 20*b*, EMR emitters 160*ah*, and EMR emitters 160*ag* will be powered by the battery 476*b*. Electrical power can be distributed throughout the sterile site apparatus 1 and its systems via the transmission wires 784. The control system 20*b* will serve to activate, deactivate, and alter the outputs of the sterile site apparatus 1 based on inputs it receives, such as the flow rate of the fluid 785. Signals for inputs and outputs will also be sent and received via the transmission wires 784. If the flow sensor 3*h* detects flow moving through the sterile site apparatus 1, it will be advantageous to disinfect the fluid 785 to prevent infectious agents from reaching the sterile site 52. Once the flow sensor 3*h* detects flow of the fluid 785, a signal will be sent to the control system 20*b*. The control system 20*b* will then send a signal to the EMR emitters 160*ag* and the EMR emitters 160*ah*. The EMR emitters 160*ag* will generate and emit the desired wavelength(s) of EMR to form an EMR barrier 161*l*. The EMR emitters 160*ah* will generate the desired wavelength(s) EMR, transmit the EMR through fiber optics 320, and emit the EMR from the ends of the fiber optics 320 to form an EMR barrier 161*m*. By passing the fluid 785 through the EMR barriers 161*l* and 161*m*, infectious agents will no longer pose any danger to the sterile site 52. It should be noted that the EMR emitters 160*ag* and fiber optics 320 can be distributed continuously throughout the entire inner surface of the sterile site apparatus 1. It should be noted that it would be advantageous to locate the EMR barriers 161*l* and 161*m* downstream of the flow sensor 3*h* and upstream of the sterile site 52. Using this configuration is beneficial because it will ensure that any infectious agents in the fluid 785 between the flow sensor 3*h* and EMR barriers 161*l* and 161*m* are disinfected. It should also be noted that the sterile site apparatus 1 can have other appearances and features than those in FIGS. 222-224.

FIGS. 225-230 illustrate the ability of the sterile site apparatus 1 to partially or fully surround the exterior surface of a length of a tubular medical device 800. The functions, systems, features and other details of the sterile site apparatuses 1 in FIGS. 225-230 will be the same as those described in FIGS. 222-224 with the exception that the sterile site apparatuses 1 in FIGS. 225-230 will not couple two separate tubular medical devices. FIGS. 225-226 show a top housing component 41ad and bottom housing component 41an that can be attached to each other after being assembled over the tubular medical device 800. FIGS. 227-228 show a housing that will consist of two housing components 41ae and 41af that will be connected along a hinge joint 801, which can be opened and/or closed on the tubular medical device 800 by pushing on both handles 802 of the housing components 41ae and 41af. FIGS. 229-230 show a housing 41ag that can be slid over and onto the tubular medical device 800.

FIGS. 231-234 illustrate the ability of the sterile site apparatus 1 and its associated housing 41ah to attach to the exterior of a multi-line tubular medical device 810 and surround several tubular medical device lines 811 and 812 of the multi-line tubular medical device 810. While FIGS. 231-234 show the sterile site apparatus 1 attached to multiple tubular medical device lines 811 and 812 of the same multi-line tubular medical device 810, it is conceivable that the sterile site apparatus 1 will attach to tubular medical device lines from multiple tubular medical devices. For the configuration shown in FIG. 234, fluid will be flowing from left to right in the second tubular medical device line 812 and fluid will be flowing from right to left in the first tubular medical device line 811. The sterile site 52 will be a portion of the inner region of a tubular medical device line that is downstream from and distant to the sterile site apparatus 1. The housing 41ah will contain features and components including but not limited to flow sensors 3i, control systems 20c, batteries 476c, EMR emitters 160aj and 160al, transmission wires 784a, and fiber optics 320. The flow sensors 3i can use any of a number of known technologies to measure the flow rate of the fluid contained within the tubular medical device lines 811 and 812 without contacting the fluid. The flow sensors 3i, control systems 20c, and EMR emitters 160aj and 160al will be powered by the batteries 476c. Electrical power can be distributed throughout the sterile site apparatus 1 and its systems via the transmission wires 784a. The control system 20c will serve to activate, deactivate, and alter the outputs of the sterile site apparatus 1 based on inputs it receives, such as the flow rate of the fluid. Signals for inputs and outputs will also be sent and received via the transmission wires 784a. If the flow sensors 3i detect flow moving through the sterile site apparatus 1, it will be advantageous to disinfect the fluid to prevent infectious agents from reaching the sterile site 52. Once the flow sensors 3i detect flow of the fluid, a signal will be sent to the control systems 20c. The control systems 20c will then send a signal to the EMR emitters 160al and 160aj. The EMR emitters 160al will generate and emit the desired wavelength(s) of EMR to form the EMR barriers 161n. The EMR emitter 160aj will generate the desired wavelength(s) EMR, transmit the EMR through fiber optics 320, and emit the EMR from the ends of the fiber optics 320 to form the EMR barriers 161t. By passing the fluid through the EMR barriers 161n and 161t, infectious agents will no longer pose any danger to the sterile site 52. It should be noted that the EMR emitters 160al and fiber optics 320 can be distributed continuously throughout the entire inner surface of the sterile site apparatus 1. It should be noted that it would be advantageous to locate the EMR barriers 161n and 161t downstream of the flow sensor 3i and upstream of the sterile site 52. Using this configuration is beneficial because it will ensure that any infectious agents in the fluid between the flow sensor 3i and EMR barriers 161n and 161t are disinfected. It should also be noted that the sterile site apparatus 1 can have other appearances and features than those in FIGS. 231-234. While a tubular medical device related to blood dialysis treatment is shown in FIGS. 231-234, any of a number of tubular medical devices may be used in its place.

FIGS. 235-237 illustrate the ability of the sterile site apparatus 1 and its associated housing 41ai to be inserted into and along the inner surface of a tubular medical device 821. For this configuration, the tubular medical device 821 is located within the internal pathway of a patient 820. A tubular medical device 821 can include but is not limited to central line catheters, urinary catheters, pacemaker leads, and intubation tubes. The internal pathway of a patient 820 can include but is not limited to respiratory passageways, arteries, veins, and the urinary tract. The sterile site 52 is designated as the inner surface of the internal pathway of a patient 820. To prevent infectious agents or biofilm 822 on the exterior surface of a tubular medical device 821 from coming into contact with the sterile site 52, it is advantageous to disinfect the infectious agents or biofilm 822. This can be done by first inserting the housing 41ai through the center of the tubular medical device 821. The sterile site apparatus 1 and its housing 41ai can then be advanced through and along the tubular medical device 821. Once at the desired location, the sterile site apparatus 1 and its housing 41ai will emit an EMR barrier 1610 from EMR emitters 160ak. To perform properly, the tubular medical device 821 should be made of materials that will allow the desired wavelength(s) of EMR of the EMR barrier 1610 to pass through the tubular medical device 821 and disinfect the infectious agents or biofilm 822. It should be noted that the EMR needed for the EMR barrier 1610 can be distributed through the housing 41ai using a variety of known technologies including but not limited to fiber optics, EMR generators, and stimulated emission.

FIGS. 238-240 illustrate the ability of the sterile site apparatus 1 and its associated housing 41aj to be inserted into the internal pathway of a patient 820 and over the tubular medical device 821. For this configuration, the tubular medical device 821 is located within the internal pathway of a patient 820. The sterile site 52 is designated as the inner surface of the internal pathway of a patient 820. To prevent infectious agents or biofilm 822 on the exterior surface of a tubular medical device 821 from coming into contact with the sterile site 52, it is advantageous to disinfect the infectious agents or biofilm 822. This can be done by first inserting the housing 41aj through the internal pathway of a patient 820 and over the tubular medical device 821. The sterile site apparatus 1 and its housing 41aj can then be advanced over and along the tubular medical device 821. Once at the desired location, the sterile site apparatus 1 and its housing 41aj will emit an EMR barrier 161p, which is created by the EMR emitters 160al. It should be noted that the EMR needed for the EMR barrier 161p can be distributed through the housing 41aj using a variety of known technologies including but not limited to fiber optics, EMR generators, and stimulated emission.

FIGS. 241-243 illustrate the ability of the sterile site apparatus 1 and its associated housing 41ak to be inserted into the internal pathway of a patient 820. For this configuration, the sterile site apparatus 1 and its housing 41ak have functions and features in addition to those of a tubular medical device, which the sterile site apparatus 1 and its housing 41ak are replacing. In addition to performing the same functions as the tubular medical device it is replacing, the sterile site apparatus 1 also has the ability to disinfect the outer surface of the housing 41ak, which is a common location for the accumulation of infectious agents and biofilm 822. The sterile site 52 is designated as the inner surface of the internal pathway of a patient 820. To prevent infectious agents or biofilm 822 on the exterior surface of housing 41ak from coming into contact with the sterile site 52, it is advantageous to disinfect the infectious agents or biofilm 822. This can be done by having the EMR emitters 160am emit an EMR barrier 161q while the housing 41ak is still within the patient. It should be noted that the EMR needed for the EMR barrier 161q can be distributed through the housing 41ak using a variety of known technologies including but not limited to fiber optics, EMR generators, and stimulated emission.

FIGS. 244-248 illustrate the ability of the sterile site apparatus 1 and its housing 41al to attach to the exterior of a tubular medical device 821, emit an EMR barrier 161r into a contaminated region 835, and emit an EMR barrier 161r into the tubular medical device 821 where the EMR will be transmitted and contained within tubular medical device 821. For this configuration, the housing 41al would be made of a semi-rigid or flexible material so that it can be wedged apart and have its gap 830 enlarged enough so that the housing 41al can fit over the tubular medical device 821. EMR will be delivered to the transmission and emission medium 831 at the attachment face 832, where the housing 41al can be connected to a supply cord 40 (FIG. 3) or other EMR source. Once the EMR is within the transmission and emission medium 831, the EMR will be released from the transmission and emission medium 831. The EMR will be released towards the contaminated region 835 of the patient 834 and towards the tubular medical device 821. The contaminated region 835 is a region of the patient 834 that contains an undesirably high level of infectious agents. The sterile site 52 will be defined as the part of the patient 834 that is on the boundary between the contaminated region 835 and the rest of the patient 834, but is not contaminated by infectious agents. EMR is released towards the contaminated region 835 in order to kill the infectious agents in the contaminated region 835 and prevent them from spreading to the sterile site 52. EMR is released towards the tubular medical device 821 in order to have the EMR enter, become contained within, and transmit through the tubular medical device 821. The EMR contained transmitted within the tubular medical device 821 can then be used for a variety of purposes including but not limited to disinfecting infectious agents on the interior and exterior surfaces of the portion of the tubular medical device 821 within the patient.

FIGS. 249-251 illustrate the ability of the sterile site apparatus 1 and its housing 41ao to attach to the exterior of a tubular medical device 821 and use a heating element 2a to generate heat 843, which can aid in preventing the infectious agents or biofilm 822a on the outer surface of the patient 834a from coming into contact with the sterile site 52. For this configuration, the sterile site 52 is the region between the patient 834a and the exterior of the tubular medical device 821 and is the inner region of the tubular medical device 821 that is within the patient 834a. The heating element 2a will generate heat 843 using any of a number of known technologies including but not limited to resistance heaters, radio frequency heating of a material, and exothermic chemical reactions including but not limited to sodium acetate trihydrate reactions and ferrous materials reactions. If the heating element 2a requires additional means, including but not limited to electricity, heat, or chemical energy, for generating heat 843, these means will be delivered to the heating element 2a via the power wire 841, which can be connected to the supply cord 40 (FIG. 3) (not shown). Heat 843 will be transferred to the tubular medical device 821. The heated tubular medical device 821 will have the ability to heat the inner surface or fluid contained within the tubular medical device 821 and also heat portions of the patient 834a near the tubular medical device 821. This will also heat infectious agents in these areas. Heating infectious agents is advantageous because elevating the temperature above a threshold, such as 105 degrees Fahrenheit, has been shown to significantly slow the rate of growth for a wide range of infectious agents. With a decreased rate of growth, the heated infectious agents will have a lower risk of causing infection. Heating the regions of the patient 834a near infectious agents is additionally advantageous because and elevated body temperature has been shown to enhance the ability of the immune system to defend against infectious agents. Heating at higher heats such as 300 degrees Fahrenheit will serve to disinfect infectious agents on the inner and outer surfaces of the tubular medical device 821.

FIGS. 252-254 illustrate the ability of the sterile site apparatus 1 and its housing 41ap to attach to the exterior of a tubular medical device 821 and use an electromagnetic field generator 844 to generate an electric field 845, which can aid in preventing the infectious agents of biofilm 822a on the outer surface of the patient 834a from coming into contact with the sterile site 52. For this configuration, the sterile site 52 is the region between the patient 834a and the exterior of the tubular medical device 821 and is the inner region of the tubular medical device 821 that is within the patient 834a. The electromagnetic field generator 844 will generate an electric field 845 using any of a number of known technologies such as pulsed electrical field (PEF), alternating current electric field, direct current electric field, or a high frequency electric field. If the electromagnetic field generator 844 requires additional means, including but not limited to electricity, for generating the electric field 845, these means will be delivered to the electromagnetic generator 844 via the power wire 841a, which can be connected to the supply cord 40 (FIG. 3) (not shown). The electric field 845 will act on the tubular medical device 821, the fluid contained within the tubular medical device 821, the region of the patient 834a near the sterile site apparatus 1, and the infectious agents contained in those areas. Using an electric field 845 on infectious agents is advantageous because electric fields 845 have been shown to eliminate or reduce the growth rate of infectious agents. With a reduce number of infectious agents or a decreased growth rate of infectious agents, there will be a lower risk of infection.

FIGS. 255-256 show the ability of the sterile site apparatus 1 and its associated housing 41bn to use several features to reduce risk of infection and retract body tissue 547a. It should be noted that housing 41bn can be configured in any geometry and out of any materials to serve the function of retracting body tissue 547a. The opening/closing feature 130a will alter the sterile site apparatus 1 and serve to increase the size, decrease the size, and maintain the shape of the opening used to access the sterile site 52. The retracting feature 542a will hold back body tissue 547a in order to maintain the shape and size of the opening leading to the sterile site 52. The retracting feature 542 will also prevent infectious agents on the exterior surface of the body tissue 547a from touching objects, such as medical instruments or the user's hand, which will come into contact with the sterile site 52. The sterile site apparatus 1 can also use heating elements 2b and 2c, which can be located internally or externally to the sterile site apparatus 1 as seen in FIG. 256, to heat infectious agents and body tissue 547a. Heat will slow the growth rate of the infectious agents and also boost the immune response of the patient. Both of these effects will reduce the risk of infection. Conductive materials 846 can be used to effectively deliver heat from a heating element 2b to a targeted area. Highly conductive coatings and filler can enhance the ability of the sterile site apparatus 1 to transfer heating or cooling to the sterile site 52 and surrounding body tissue 547a. Coatings 260a can also be used anywhere on the sterile site apparatus 1 to serve a variety of purposes including but not limited to antimicrobial, antibiotic, antiviral, antifungal, and antiparasitic applications.

FIGS. 257-258 illustrate the ability of the sterile site apparatus 1 to use an object sensor 3c, which is contained in the housing 41s, to detect an object 91 passing through the detecting region 471. The object 91 can be large objects, such as a hand, or smaller slender objects such as catheters. Depicted in FIGS. 257-258 is an object 91 with two separate projections that join 91b and step down to a smaller profile 91a. When an object 91 passes near or through this detecting region 471, two disrupted regions 472 will result corresponding to the two projections on object 91. This disruption can be used as a means to control various features of the sterile site apparatus 1. For example, when an object 91 disrupts the detecting region 471, the control system 20 (FIG. 1) could cause a feature to disinfect the object 91 as the object passes through the opening in the sterile site apparatus 1. If the object 91 is a hand, the object sensor 3c could detect when the hand enters the detecting region 471 and the control system 20 (FIG. 1) could verify that there are five fingers by the number of disrupted regions 472. The object sensor 3c could further detect if the fingers are spread apart to ensure that there are no shaded areas that might be more difficult to disinfect. As the object 91 passes through the detecting region 471, the disrupted region(s) 472 will change as the profile of the object 91 moves from the joined portion of 91b to the more slender profile 91a. This might be useful when detecting a hand to ensure that the entire hand has passed through the detecting region 471 up to the wrist and provide a signal to the user that they have inserted their hands far enough and that they can now be removed.

FIGS. 259-260 illustrate the ability of the sterile site apparatus 1 to use an object sensor 3c, which is contained in the housing 41s, to detect an object 91 passing through the detecting region 471. The object 91 can be large objects, such as a hand, or smaller slender objects such as catheters. Depicted in FIGS. 259-260 is an object 91 with two touching projections that join 91b and step down to a smaller profile 91a. When an object 91 passes near or through this detecting region 471, a single disrupted region 472 will result corresponding to the two touching projections on object 91. This disruption can be used as a means to control various features of the sterile site apparatus 1. For example, when an object 91 disrupts the detecting region 471, it could cause a feature to disinfect the object 91 as the object passes through the opening in the sterile site apparatus 1. If the object 91 is a hand, the object sensor 3c could detect when the hand enters the detecting region 471 and, it could verify that one or more of the fingers are touching by the number of disrupted regions 472. The control system 20 (FIG. 1) could provide a signal to the user that their fingers are touching and that the disinfection was unable to be performed.

FIGS. 261-263 illustrate the ability of the sterile site apparatus 1 to be composed of a multitude of various features and systems for disinfecting an object 91 (not shown), and be in a different location from the sterile site 52a. While FIGS. 261, 262, and 263 show these features and systems collectively, it should be noted that some features can be omitted and additional features or systems can be included. The housing 41bo is configured with an unobstructed opening 847 that leads to a passage and allows an object 91 (not shown), or multiple objects to simultaneously and freely pass through, The positively charged electrode 390b, which is part of the charged particle displacement mechanism 9 (FIG. 1), will act to attract or repel infectious agents in a manner to prevent them from coming into contact with an object 91 (not shown). It should be noted that although FIG. 263 shows a positively charged electrode 390b being used, a negatively charged electrode can be used in its place. The gas release opening 31f will release sterile gas 32 or other gas mixtures to displace infectious agents in a way that will prevent them from coming into contact with the object 91 (not shown). The shield 540b will protect the user from being exposed to EMR released at a potentially harmful trajectory. While the EMR barrier 161u, which is created by the EMR emitters 160as, will be designed to prevent EMR from being released at a potentially harmful trajectory, the safety feature of using the shield 540b will help to guarantee that operating the sterile site apparatus 1 poses minimal to no danger to the user. An ergonomic attachment 550b can be used to improve the comfort and health of the user operating the sterile site apparatus 1, and also help to mount the sterile site apparatus 1 when it is used in a different location than the sterile site 52a. For example, the sterile site apparatus 1 might be mounted to a wall, to a stand, to an entrance, a recess, or any structure where it would be useful to mount a sterile site apparatus 1. A detecting region 471b, which is created by the object sensor 3c, can be used to detect a physician's hand, small objects, such as a hemostat, and microscopic objects, such as infectious agents, traveling into or near the sterile site 52. The object sensor 3b will be used to detect objects in the ambient surroundings near the sterile site apparatus 1. The object sensor 3d will be used to detect objects that have passed through the EMR barrier 161u. The object sensor 3k, attached to the housing extension 41bp will be used to detect objects as they move through the EMR barrier 161u. The ability to detect the presence of an object near the sterile site apparatus 1 will allow certain features of the sterile site apparatus 1 to be controlled, such as activating the EMR barrier 161u only when it is needed, detecting what the object is and altering the intensity of the EMR barrier 161u. The ability to detect objects that have passed through the EMR barrier 161u will allow certain features of the sterile site apparatus 1 to be controlled, such as de-activating the EMR barrier 161u when certain features of the object 91 (not shown) have passed through. This will prolong the service life of the sterile site apparatus 1 and minimize exposure to unnecessary radiation and potentially harmful chemicals. The ability to detect objects as they move through the EMR barrier 161u can be used to ensure that the object is not passing too quickly or too slowly through the EMR barrier 161u, or to adjust the intensity of the EMR barrier 161u based on the speed that the object is travelling. The EMR barrier 161u can be used to disinfect objects that pass through the opening 847 in the sterile site apparatus 1 by using the desired wavelength(s) of EMR. The EMR barrier 161u can have a variety of functions including but not limited to disinfection. A coherent EMR barrier will be able to disinfect the entire exterior surface of an object 91 (not shown) as it passes through the opening 847. It will also be able to disinfect the exterior of objects traveling through the opening 847 even when multiple objects are simultaneously passing through the sterile site apparatus 1. Sterile site EMR 577a, which is released by separate EMR emitters 160at, will be released in the area in or near the housing extension 41*bp*, where it can perform a number of functions including but not limited to ozone generation, ozone elimination, and illumination. Fluids 8*b* will be released in the area in or near the housing extension 41*bp* by fluid release openings 26*d* to perform a variety of functions that include but are not limited to mold spore neutralization and infectious agent disinfection.

As shown in FIG. 264, which is the same as FIG. 77, the housing 41*bq* (corresponding to housing 41*d*) defines an unobstructed passage 902 configured to receive an object. That passage 902 has a proximal inlet 900 (corresponding to the plane extending across the top surface of the housing 41*d* in FIG. 77) and a distal outlet 901 (corresponding to the plane extending across the bottom surface of the housing 41*d* in FIG. 77). The emitters 160*au* (corresponding to emitters 160*d* in FIG. 77) are positioned to direct electromagnetic radiation into the passage 902 defined by the housing 41*bq* and being configured to create a substantially void free barrier 161*v* of electromagnetic radiation extending across the passage 902. The barrier 161*v* of electromagnetic radiation has a proximal extent 903 (e.g., corresponding to the uppermost limit of the beams 184 in FIG. 77), a distal extent 904 (e.g., corresponding to the lowermost limit of the beams 184 in FIG. 77), and a depth defined by the distance between the proximal extent 903 and the distal extent 904. As evident in FIG. 77 and FIG. 264, an outer perimeter of an object would not intersect the barrier 161*v* when the entire object is proximal to the proximal inlet 900 of the passage 902 (i.e., above the inlet in the embodiment shown in FIG. 77 and FIG. 264) or distal to the distal outlet 901 of the passage 902 (i.e., below the outlet in the embodiment shown in FIG. 77 and FIG. 264) and intersects the barrier 161*v* when the object passes through the proximal inlet 900 to the distal outlet 901. The barrier 161*v* therefore creates a substantially void free intersection of electromagnetic radiation with the object perimeter corresponding to the depth of the barrier 161*v* as the object passes between the proximal inlet 900 and distal outlet 901 of the passage 902.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The appended claims are thus to be understood to include what is specifically illustrated and described above, what is conceptually equivalent, what can be obviously substituted and also what essentially incorporates the essential idea of the embodiments.

What is claimed is:

1. A method for creating an infectious agent barrier for a sterile site, the method comprising the steps of:

operating an arm assembly at or near the sterile site, the arm assembly including a hollow member, moveable joints connected to the hollow member, an electromagnetic radiation barrier that is configured to emit ultraviolet radiation and is attached to the hollow member and indirectly connected to the moveable joints by way of the hollow member, and a sterile cover that covers the electromagnetic radiation barrier, the arm assembly at least partially defining an opening through which an object to be disinfected can access the sterile site; and activating the electromagnetic radiation barrier to create a field of energy across the opening that is substantially free of voids such that the electromagnetic radiation barrier inactivates infectious agents entering the sterile site; and moving the hollow member and electromagnetic radiation barrier about the movable joints and with respect to the object while the electromagnetic barrier is activated for inactivating infectious agents on the object.

2. The method of claim 1, wherein the electromagnetic radiation barrier further comprises a proximal opening and a distal opening, whereby an outer perimeter of the object does not intersect the electromagnetic radiation barrier when the entire object is either proximal to the proximal opening or distal to the distal opening.

3. The method of claim 1, further comprising extending the field of energy a pre-determined distance down a length of the object as the object passes through the opening and into the sterile site.

4. The method of claim 1, wherein the electromagnetic radiation barrier further comprises a lens, reflective surface, or minimally divergent beam for limiting the electromagnetic radiation field of energy to remain within the opening.

5. The method of claim 1, further comprising disinfecting an exterior surface of the object.

* * * * *